US008242249B2

(12) United States Patent
Ishikawa

(10) Patent No.: US 8,242,249 B2
(45) Date of Patent: Aug. 14, 2012

(54) **PRIMER AND PROBE FOR USE IN DETECTION OF *MYCOBACTERIUM KANSASII* AND METHOD FOR DETECTION OF *MYCOBACTERIUM KANSASII* USING THE SAME**

(75) Inventor: Tomokazu Ishikawa, Hyogo (JP)

(73) Assignee: Wako Pure Chemical Industries, Ltd., Osaka (JP)

( * ) Notice: Subject to any disclaimer, the term of this patent is extended or adjusted under 35 U.S.C. 154(b) by 752 days.

(21) Appl. No.: 11/920,234

(22) PCT Filed: May 11, 2006

(86) PCT No.: PCT/JP2006/309514

§ 371 (c)(1),
(2), (4) Date: Nov. 13, 2007

(87) PCT Pub. No.: WO2006/121134

PCT Pub. Date: Nov. 16, 2006

(65) Prior Publication Data

US 2009/0298057 A1 Dec. 3, 2009

(30) Foreign Application Priority Data

May 13, 2005 (JP) ................................ 2005-141153

(51) Int. Cl.

| | |
|---|---|
| ***C07H 21/02*** | (2006.01) |
| ***C07H 21/04*** | (2006.01) |
| *C12Q 1/68* | (2006.01) |
| *C12P 19/34* | (2006.01) |

(52) U.S. Cl. ...... 536/23.1; 435/6.1; 435/91.2; 536/24.3; 536/24.32; 536/24.33

(58) Field of Classification Search ........................ None
See application file for complete search history.

(56) References Cited

U.S. PATENT DOCUMENTS

| | | | |
|---|---|---|---|
| 5,500,341 | A | 3/1996 | Spears |
| 6,013,510 | A | 1/2000 | Harris et al. |
| 6,291,176 | B1 | 9/2001 | Harris et al. |

FOREIGN PATENT DOCUMENTS

| | | | |
|---|---|---|---|
| EP | 1431400 | A2 | 6/2004 |
| JP | 11-155589 | | 6/1999 |

OTHER PUBLICATIONS

Frédéric Poly et al., Identification of *Campylobacter jejuni* ATCC 43431-Specific Genes by Whole Microbial Genome Comparisons, Journal of Bacteriology, Jul. 2004, p. 4781-4795.

Böddinghaus, et al., "Detection and Identification of Mycobacteria by Amplification of rRNA", Journal of Clinical Microbiology, vol. 28, No. 8, pp. 1751-1759, (Aug. 1990).

Yang, et al., "Isolation of a DNA Probe for Identification of *Mycobacterium kansasii*, Including the Genetic Subgroup", Journal of Clinical Microbiology, vol. 31, No. 10, pp. 2769-2772, (1993).

Ross, et al., "Identification of a Genetically Distinct Subspecies of *Mycobacterium kansasii*", Journal of Clinical Microbiology, vol. 30, No. 11, pp. 2930-2933, (1992).

Huang, et al., "Identification of *Mycobacterium kansasii* by DNA Hybridization", Journal of Clinical Microbiology, vol. 29, No. 10, pp. 2125-2129, (1991).

Tortoli, et al., "Evaluation of a Commercial DNA Probe Assay for the Identification of *Mycobacterium kansasii*", Eur. J. Clin. Microbiol. Infect. Dis., vol. 13, pp. 264-267, (1994).

Poly, et al., "Identification of *Campylobacter jejuni* ATCC 43431-Specific Genes by Whole Microbial Genome Comparisons", Journal of Bacteriology, vol. 186, No. 14, pp. 4781-4795, (2004).

*Primary Examiner* — Teresa E Strzelecka

(74) *Attorney, Agent, or Firm* — Finnegan, Henderson, Farabow, Garrett & Dunner, LLP

(57) ABSTRACT

The present invention discloses an oligonucleotide which comprises a part or the entire sequence of the nucleotide sequence depicted in SEQ ID NO: 1, 2, 3 or 4, or a part or the entire sequence of a nucleotide sequence complementary to the nucleotide sequence, wherein the oligonucleotide is capable of hybridizing with the nucleotide sequence of *Mycobacterium kansasii*; a primer and a probe for use in the detection of *Mycobacterium kansasii* comprising the oligonucleotide; and a method for detecting *Mycobacterium kansasii* using the primer and/or probe.

The method for detecting *Mycobacterium kansasii* enables the detection of *M. kansasii* more rapidly and with higher accuracy compared with a conventional bacterium identification method performed by culture examination on a bacterium. Further, the method can exclude any false positive result for the diagnosis and can also detect and diagnose *M. kansasii* with higher accuracy compared with a diagnosis method performed by PCR using a conventional primer and/or probe. Still further, the method can quantify a *M. kansasii* cell.

25 Claims, 7 Drawing Sheets

[Fig.1]
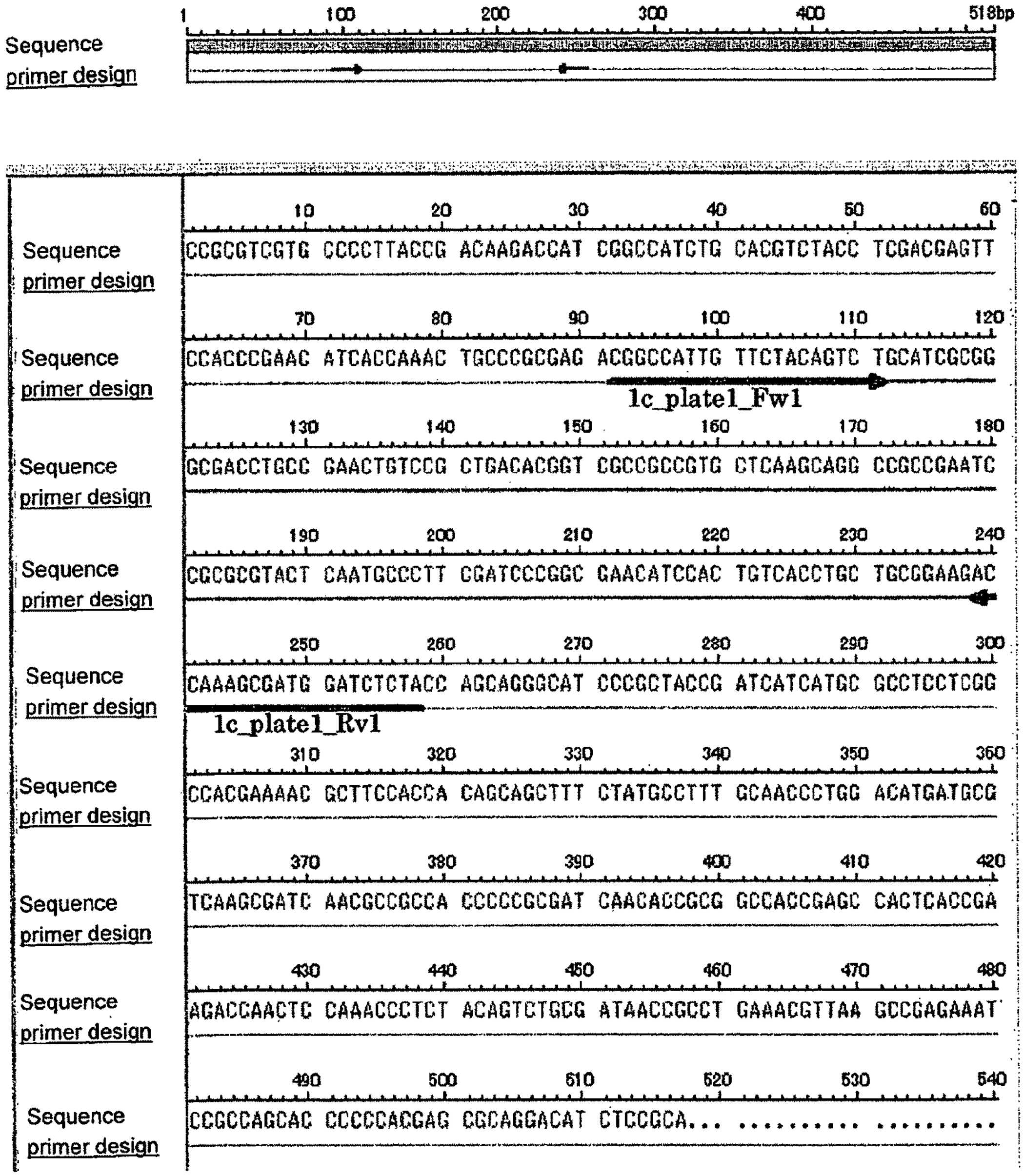

[Fig.2]
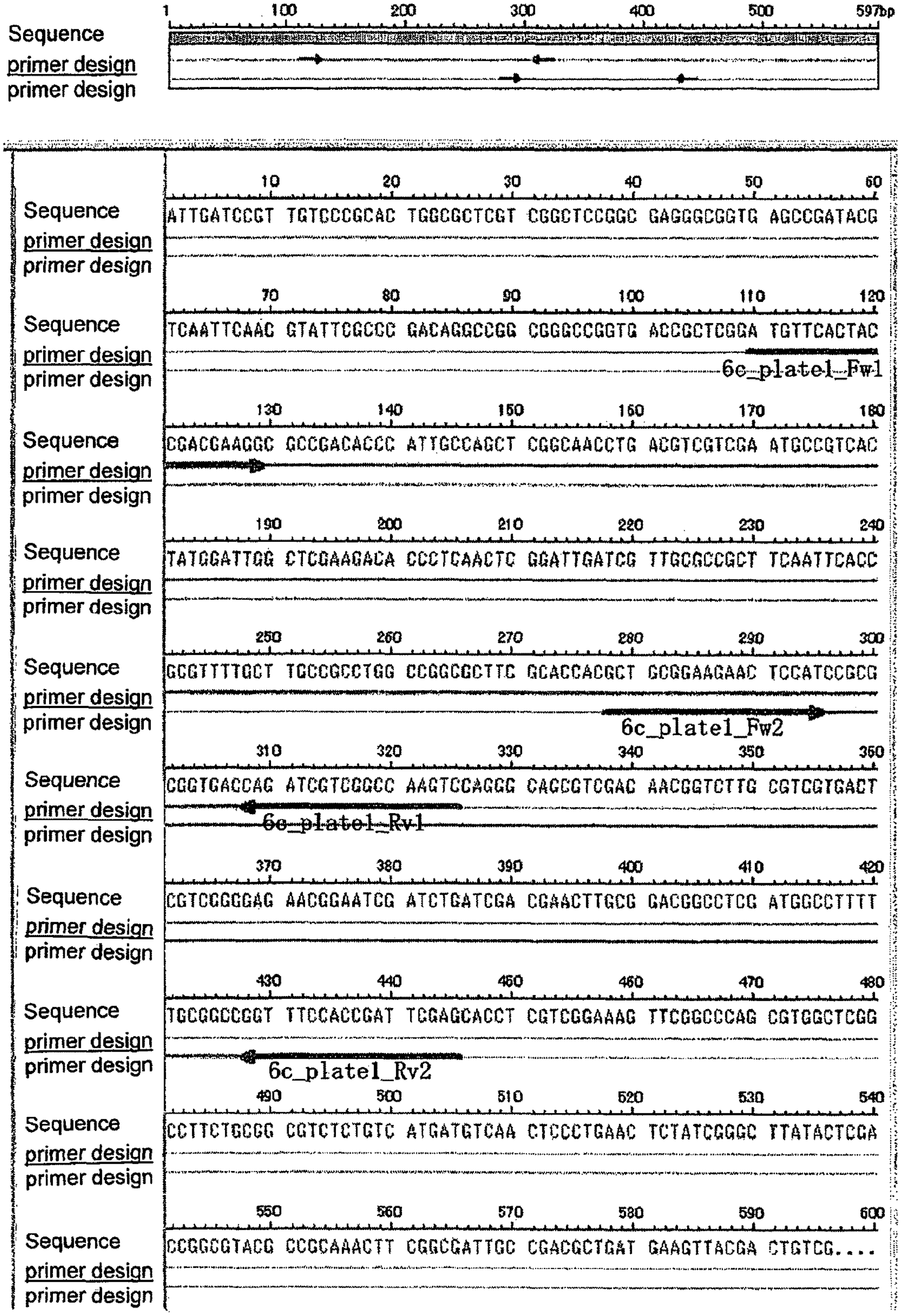

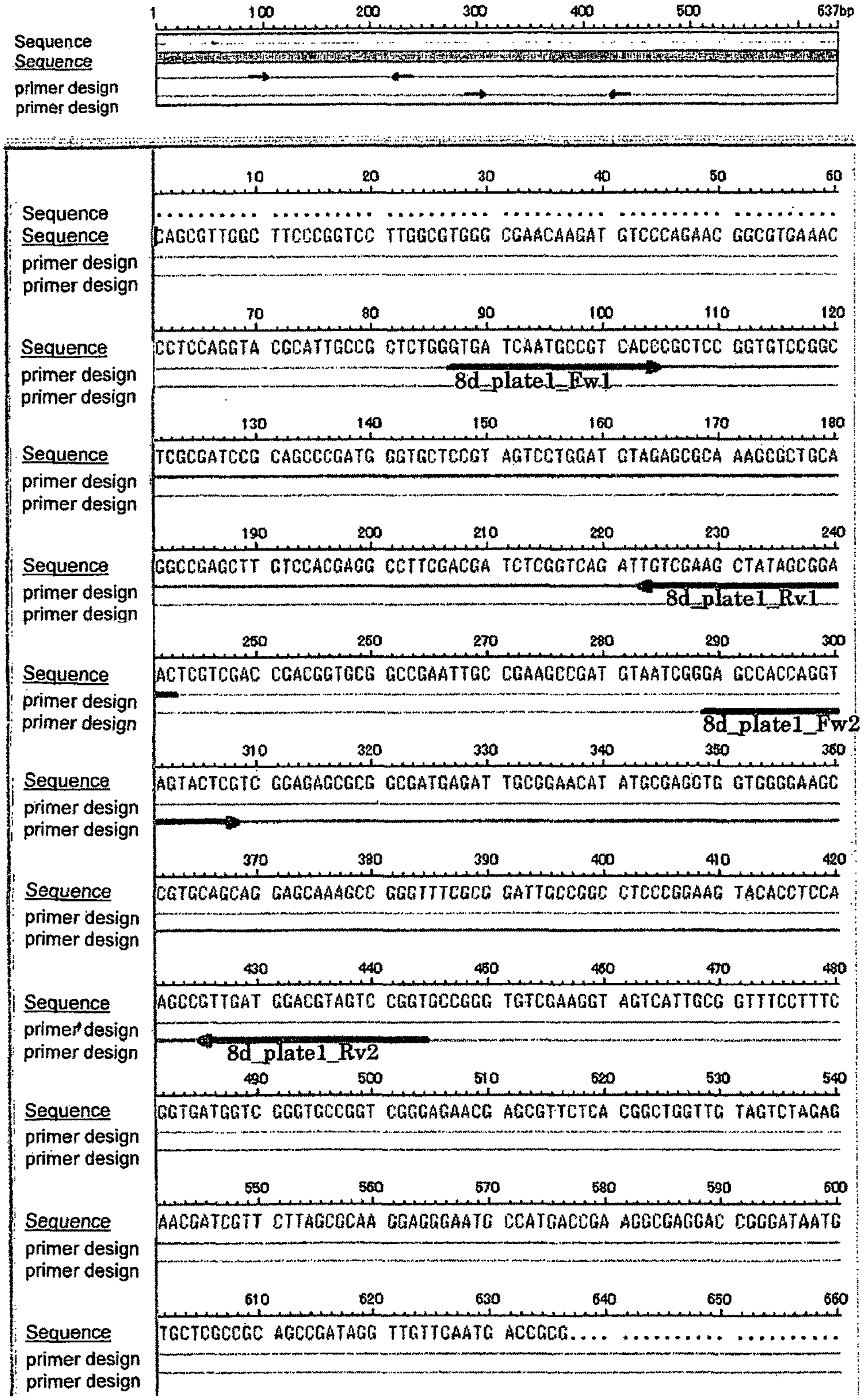

[Fig.3]

```
                   1    100      200      300      400      500    637bp
Sequence
Sequence
primer design
primer design

                   10        20        30        40        50        60
Sequence
Sequence      CAGCGTTGGC TTCCCGGTCC TTGGCGTGGG CGAACAAGAT GTCCCAGAAC GGCGTGAAAC
primer design
primer design

                   70        80        90       100       110       120
Sequence      CCTCCAGGTA CGCATTGCCG CTCTGGGTGA TCAATGCCGT CACCCGCTCC GGTGTCCGGC
primer design                                        ────8d_plate1_Fw1──────►
primer design

                  130       140       150       160       170       180
Sequence      TCGCGATCCG CAGCCCGATG GGTGCTCCGT AGTCCTGGAT GTAGAGCGCA AAGCGCTGCA
primer design
primer design

                  190       200       210       220       230       240
Sequence      GGCCGAGCTT GTCCACGAGG CCTTCGACGA TCTCGGTCAG ATTGTCGAAG CTATAGCGGA
primer design                                           ◄──────8d_plate1_Rv1
primer design

                  250       260       270       280       290       300
Sequence      ACTCGTCGAC CGACGGTGCG GCCGAATTGC CGAAGCCGAT GTAATCGGGA GCCACCAGGT
primer design
primer design                                                    ──8d_plate1_Fw2

                  310       320       330       340       350       360
Sequence      AGTACTCGTC GGAGAGCGCG GCGATGAGAT TGCGGAACAT ATGCGAGGTG GTGGGGAAGC
primer design ────►
primer design

                  370       380       390       400       410       420
Sequence      CGTGCAGCAG GAGCAAAGCC GGGTTTCGCC GATTGCCGGC CTCCCGGAAG TACACCTCCA
primer design
primer design

                  430       440       450       460       470       480
Sequence      AGCCGTTGAT GGACGTAGTC CGGTGCCGGG TGTCGAAGGT AGTCATTGCG GTTTCCTTTC
primer design
primer design ◄──────8d_plate1_Rv2

                  490       500       510       520       530       540
Sequence      GGTGATGGTC GGGTGCCGGT CGGGAGAACG AGCGTTCTCA CGGCTGGTTG TAGTCTAGAG
primer design
primer design

                  550       560       570       580       590       600
Sequence      AACGATCGTT CTTAGCGCAA GGAGGGAATG CCATGACCGA AGGCGAGGAC CGGGATAATG
primer design
primer design

                  610       620       630       640       650       660
Sequence      TGCTCGCCGC AGCCGATAGG TTGTTCAATG ACCGCG....  .........  .........
primer design
primer design
```

[Fig.4]
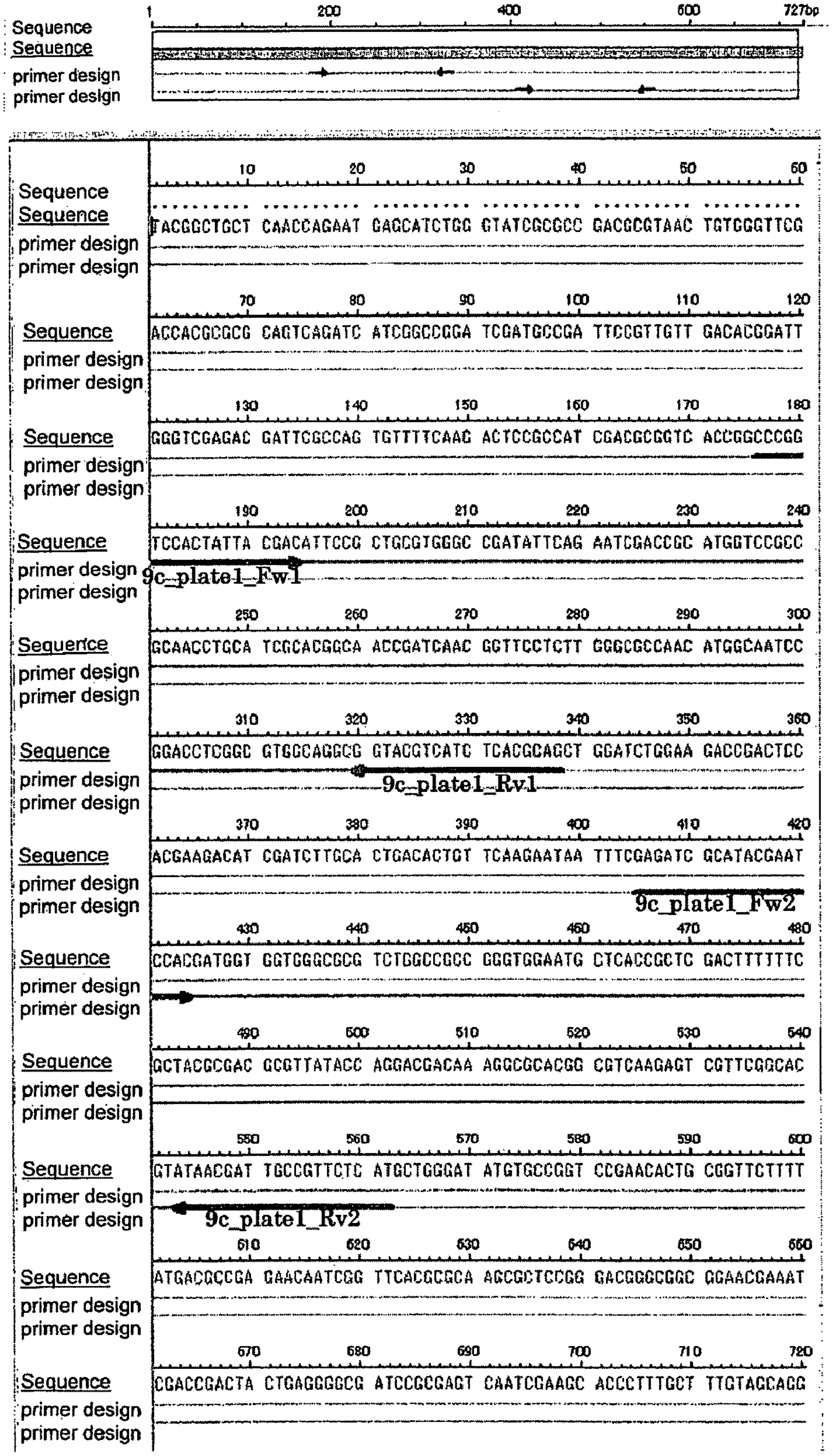

[Fig.5]
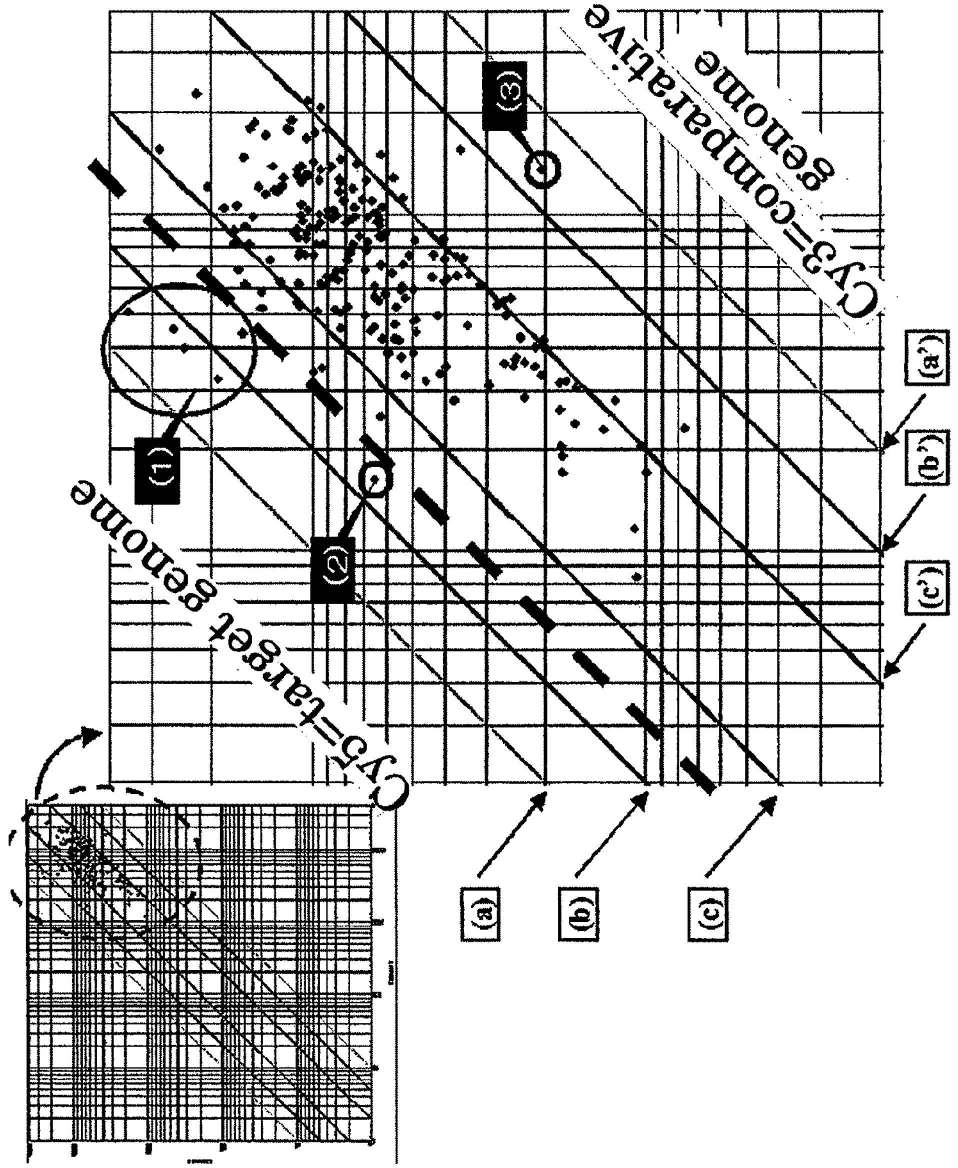

[Fig.6]
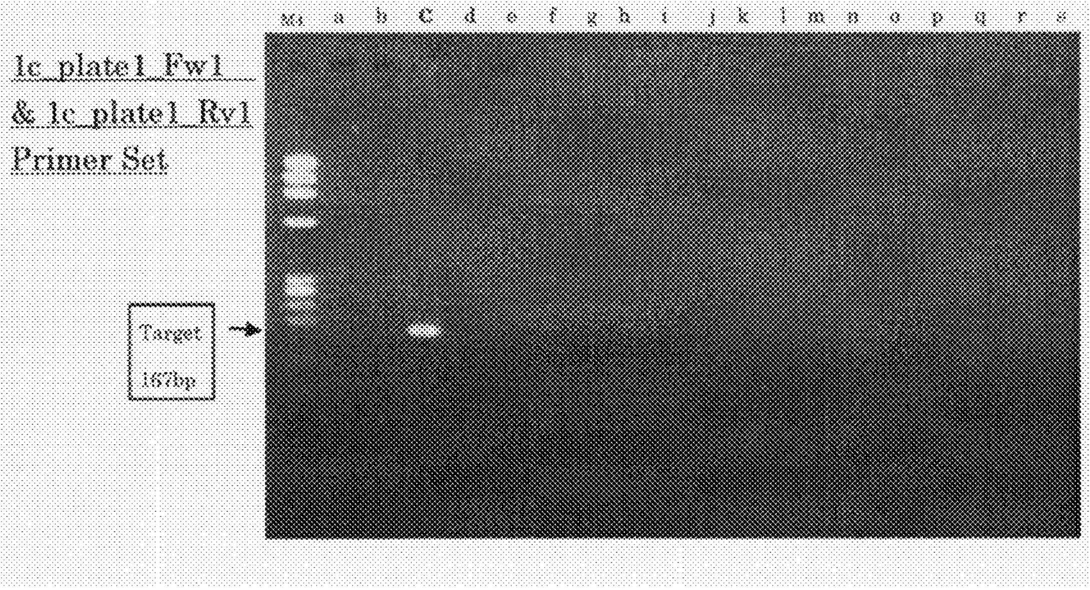

[Fig.7]
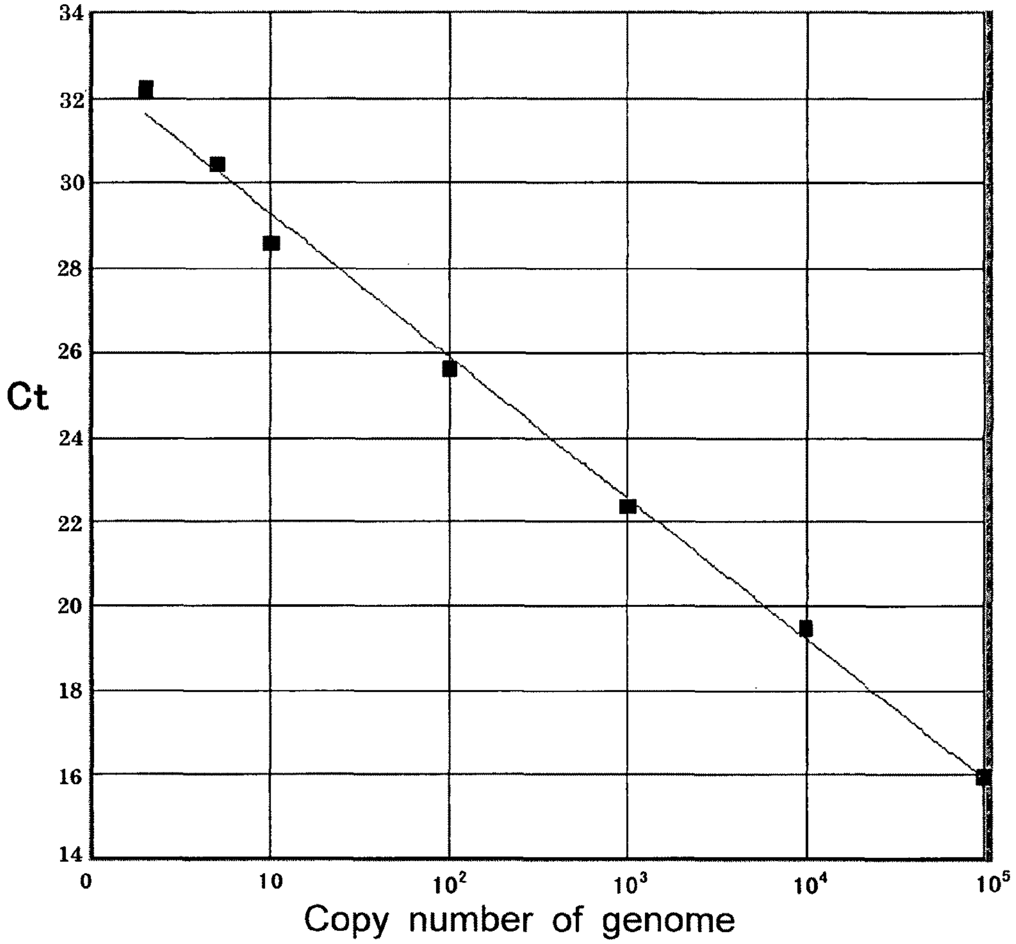

PRIMER AND PROBE FOR USE IN DETECTION OF *MYCOBACTERIUM KANSASII* AND METHOD FOR DETECTION OF *MYCOBACTERIUM KANSASII* USING THE SAME

TECHNICAL FIELD

The present invention relates to a method for detecting and/or identifying *M. kansasii* (*Mycobacterium kansasii*, hereinafter described as *M. kansasii*) through the use of amplification of nucleic acid and detection system thereof in clinical laboratory test.

BACKGROUND ART

Nontuberculous *mycobacterium* (NTM) is a gram positive bacillus having acid-fast characteristics classified into genus *Mycobacterium*, and is a sort of acid-fast bacterium other than tuberculosis complex and *Mycobacterium leprae*.

Among nontuberculous *mycobacterium*, clinically problematic bacterial strain is known to include *Mycobacterium kansasii, Mycobacterium marinum, Mycobacterium gordonae, Mycobacterium szulgai, Mycobacterium avium, Mycobacterium intracellulare, Mycobacterium xenopi, Mycobacterium fortuitum, Mycobacterium chelonei, Mycobacterium abscessus*, and so on. Particularly, the infectious diseases affected by 2 types of bacteria, *M. kansasii* and *M. avium* complex, accounts 90% or more of the total nontuberculous mycobacterium diseases.

In general, the nontuberculous *mycobacterium* is said to be harmless to a healthy subject, however, on rare occasions, it may exert infectivity to human and causes nontuberculous *mycobacterium* diseases. Particularly in the immunocompromised subjects such as AIDS-virus-infected patients, it may be a serious infection-causative agent. In the past, the nontuberculous *mycobacterium* diseases have been rare disorder, however, in recent years, the incidence of infection demonstrates upward trend, and therefore, the development of a method for discriminating tuberculosis bacterium from nontuberculous *mycobacterium* in a short period of time has been desired strongly. Moreover, from the fact that the method for detecting/diagnosing *M. avium* and *M. intracellulare* by nucleic-acid amplification has been approved for its inclusion in health insurance coverage and then spread rapidly throughout the country, its diagnostic significance is obviously great.

Since most of nontuberculous mycobacteria have a resistance to antituberucular agents, when the patient is suspected of acid-fast bacterium infection, the differential diagnosis whether the disease is tuberculosis or nontuberculous mycobacterium disease will be quite important to decide on the course of treatment. In addition, as the method for the treatment of the diseases caused by nontuberculous mycobacteria may vary for each type of bacterium, the identification of bacterial species will also be quite important. However, since nontuberculous *mycobacterium* disease has no specific clinical symptom, it is quite difficult to differentiate tuberculosis from nontuberculous mycobacterium disease by clinical observation and histopathological manifestation, moreover, to specify the species of the nontuberculous *mycobacterium*. Therefore, the diagnosis whether the disease is tuberculosis or nontuberculous *mycobacterium* disease has to be performed by identification of the infected bacterium.

In a typical diagnosis, at first, sputum smear is examined. By this test, only "positive acid-fast bacterium" can be recognized, and differentiation of tuberculosis bacterium from nontuberculous *mycobacterium* cannot be achieved. Therefore, when the sputum smear examination is positive, bacterial culture examination by isolation culture on a specified culture medium such as Ogawa's medium is carried out to differentiate tuberculosis bacterium from nontuberculous *mycobacterium*. Further, through additional biochemical examinations, species of the bacterium is identified. However, in general, growth of bacterium belonging to genus *Mycobacterium* is slow, and takes considerable time for its culture. Accordingly, in the basic procedures of conventional method including smear examination and culture examination, it takes 3 to 4 weeks only for the isolation culture of the bacterium to obtain diagnostic outcome informing whether the bacterium is tuberculosis or not. In addition, there is another problem that it requires additional 2 to 3 weeks to complete various biochemical tests for the identification of bacterial species.

In addition, identification of *M. kansasii* is also performed by biochemical tests. The principal method of identifying *M. kansasii* by biochemical tests utilizes the specific property of producing pigment when the bacterium is exposed to the light. However, since some other species belonging to genus *Mycobacterium* show the same properties as *M. kansasii* shows, the identification of *M. kansasii* by its coloring property is generally of a problem.

In recent years, technology of detecting bacteria on a genetic level has been developed. For example, a diagnostic technique utilizing nucleic acid amplification technology such as polymerase chain reaction (PCR) and the like have been studied as a useful means. This method has advantages of high sensitivity; several cells of the bacteria are enough for the detection; detection can be completed in a short time (in 4 days at the longest). However, in the usual PCR method, both live cells and dead cells are detected equally. In addition, as the judgment is made positive regardless of the size of bacterial count, and since the number of the bacterium is unknown, diagnosis of infectivity whether it is positive or not will be provided with uncertainty. In addition, since the method has a problem that due to too high sensitivity, the possibility of false positive judgment or the like tends to be made.

As to *M. kansasii*, there is a study reporting that a DNA probe (pMK1-9) was obtained from genomic library of *M. kansasii* (Non-Patent Document 1). This DNA probe (PMK1-9) can form a complemental hybrid with the DNA of *M. kansasii*, but this probe can also form a hybrid with other species of mycobacteria, and is not specific to *M. kansasii.*

Also, there is a study which paid attention to use of commercially available DNA probe (ACCU-PROBE™, Gen-Probe, San Diego, Calif.) which can hybridize specifically with pMK1-9 probe and rRNA gene of *M. kansasii* for the identification of *M. kansasii* (Non-Patent Document 2). However, in this study, it has been reported that both pMK1-9 probe and commercially available DNA probe (ACCU-PROBE™) were unable to detect considerable number of strain types of *M. kansasii.*

Further, there is another study in which the commercially available DNA probe ACCU-PROBE™) was evaluated for the detection of *M. kansasii* (Non-Patent Document 3). The researchers of this study reported that although the ACCU-PROBE™ is 100% species specific, and does not show any cross reaction with other species of *M. kansasii*, only 73% of the species of *M. kansasii* could be detected in this experiment.

There is a report describing that a DNA hybrid forming probe (p6123) specific to *M. kansasii* has been purified from a clinical isolate of *M. kansasii* (Non-Patent Document 4). The probe (p6123) was able to hybridize with all the strains of

*M. kansasii* used in this experiment including a sub-group which did not react with a DNA probe (pMK1-9) reported by Ross et al. U.S. Pat. No. 5,500,341 (Patent Document 2) has disclosed a *M. kansasii*-specific amplification primer purified from p6123 probe.

Further, B. Boddinghaus et al. have disclosed a *Mycobacterium*-specific oligonucleotide purified from 16S rRNA, which specifically proliferate and hybridize with *mycobacterium* DNA (Non-Patent Document 5).

Moreover, for example, identification of DNA region effective for detecting *M. kansasii* has also been studied (for example, Patent Document 1 and the like), however, the present situation is that the method of diagnosis specific to *M. kansasii* has not been established.

As described above, the present situation is that the establishment of a new specific method for detecting nontuberculous mycobacterium has been desired.

Patent Document 1: JP-A-11-155589;
Patent Document 2: U.S. Pat. No. 5,500,341;
Patent Document 3: JP-A-60-281;
Non-Patent Document 1: Z. H. Huang et. al., J. Clin. Microbiol., 1991, 29, p. 2125;
Non-Patent Document 2: B. C. Ross et al., J. Clin. Microbiol., 1992, 30, p. 2930;
Non-Patent Document 3: Tortoli et al., Eur. J. Clin. Microbiol. Infect. Dis., 1994, 13, p. 264;
Non-Patent Document 4: M. Yang et al., J. Clin. Microbiol., 1993, 31, p. 2769;
Non-Patent Document 5: B. Boddinghaus et al., J. Clin. Microbiol., 1990, 28, p. 1751;
Non-Patent Document 6: F. Poly et al., J. Bacteriology, 2004, 186, 14, p. 4781-4795.

DISCLOSURE OF THE INVENTION

Problems to be Solved by the Invention

The present invention was made in view of the above described situation, and an object of the present invention is to provide a new primer for detecting *M. kansasii* which can exclude any false positive result for the diagnosis; and to provide a method for detecting *M. kansasii* more simply, rapidly and with high accuracy.

Means for Solving Problems

The present invention was made for the purpose of solving the above-described problems, and comprises the following aspects:

(1) An oligonucleotide comprising a part or the entire sequence of a nucleotide sequence depicted in SEQ ID NO: 1, SEQ ID NO: 2, SEQ ID NO: 3 or SEQ ID NO: 4 (wherein A represents adenine, C represents cytosine, G represents guanine and T represents thymine, respectively; T at arbitrary position can be replaced by uracil (U); and hereinafter the same abbreviations will be used) or a part or the entire sequence of a nucleotide sequence complementary to the nucleotide sequence, wherein the oligonucleotide is capable of hybridizing with a nucleotide sequence of *M. kansasii* gene.

(2) A primer for detecting *Mycobacterium kansasii* comprising, an oligonucleotide comprising a part or the entire sequence of a nucleotide sequence depicted in SEQ ID NO: 1, SEQ ID NO: 2, SEQ ID NO: 3 or SEQ ID NO: 4, or a part or the entire sequence of a nucleotide sequence complementary to the nucleotide sequence, wherein the oligonucleotide is capable of hybridizing with a nucleotide sequence of *Mycobacterium kansasii* gene.

(3) A probe for detecting *Mycobacterium kansasii* comprising, an oligonucleotide comprising a part or the entire sequence of a nucleotide sequence depicted in SEQ ID NO: 1, SEQ ID NO: 2, SEQ ID NO: 3 or SEQ ID NO: 4, or a part or the entire sequence of a nucleotide sequence complementary to the nucleotide sequence, wherein the oligonucleotide is capable of hybridizing with a nucleotide sequence of *Mycobacterium kansasii* gene.

(4) A method for detecting *Mycobacterium kansasii* comprising;

using an oligonucleotide comprising a part or the entire sequence of a nucleotide sequence depicted in SEQ ID NO: 1, SEQ ID NO: 2, SEQ ID NO: 3 or SEQ ID NO: 4, or a part or the entire sequence of a nucleotide sequence complementary to the nucleotide sequence, wherein the oligonucleotide is capable of hybridizing with a nucleotide sequence of *Mycobacterium kansasii* as a primer and/or a probe.

(5) A kit for detecting *Mycobacterium kansasii* comprising an oligonucleotide comprising a part or the entire sequence of a nucleotide sequence depicted in SEQ ID NO: 1, SEQ ID NO: 2, SEQ ID NO: 3 or SEQ ID NO: 4, or a part or the entire sequence of a nucleotide sequence complementary to a nucleotide sequence, wherein the oligonucleotide is capable of hybridizing with the nucleotide sequence of *Mycobacterium kansasii* gene, as a primer and/or a probe.

The present inventors have conducted theoretical and experimental verification of genetic homology between species with regard to the established genes of various species including *M. kansasii* and other living organisms, and found presence of a nucleotide sequence in the nucleic acid fragments derived from *M. kansasii* obtained by the method using microarray technique, which hybridizes specifically with a particular region of the gene sequence of *M. kansasii* and may be useful for the detection of *M. kansasii*.

And so, on the basis of these findings, the present inventors have further studied intensively and obtained an oligonucleotide specific to *M. kansasii* (the nucleotide sequence depicted in SEQ ID NO: 1, SEQ ID NO: 2, SEQ ID NO: 3 or SEQ ID NO: 4), and found usefulness of these nucleotide sequences for the detection of *M. kansasii*. Based on these sequences, a primer and a probe for detecting *M. kansasii* have been developed, and using these primer and probe, a method for detecting *M. kansasii* has been established.

EFFECT OF THE INVENTION

According to the method for detecting *M. kansasii* using the primer and/or probe of the present invention, *M. kansasii* can be detected and diagnosed more rapidly and with high accuracy compared with a conventional bacterium identification method by culture examination and the like. In addition, by performing the detection using the method of the present invention, any false positive result for the diagnosis can be excluded compared with the diagnosis performed by PCR using a conventional primer and/or a probe, and as the results, *M. kansasii* can be detected and diagnosed with high accuracy. Still further, by the use of the detection method of the present invention, *M. kansasii* cell can also be quantified.

BRIEF DESCRIPTION OF THE DRAWINGS

FIG. 1 shows a nucleotide sequence of candidate clone 1, and the position where the designed primer is located is indicated by an arrow.

FIG. 2 shows a nucleotide sequence of candidate clone 2, and the position where the designed primer is located is indicated by an arrow.

FIG. 3 shows a nucleotide sequence of candidate clone 3, and the position where the designed primer is located is indicated by an arrow.

FIG. 4 shows a nucleotide sequence of candidate clone 4, and the position where the designed primer is located is indicated by an arrow.

FIG. 5 is a scatter plot produced based on the fluorescent intensity of Cy3/Cy5, obtained by use of the PCR product produced using a genome derived from *M. kansasii* in Experimental Example 1, a KATS2 sequence of *M. kansasii*, and a sequence shown as SEQ ID NO: 8 in the description of JP Application No. 2004-129272 (in the present description, shown as SEQ ID NO: 81).

FIG. 6 shows the results of electrophoresis obtained in Example 1.

In addition, letters given on each lane indicate the results when the following samples are used:

M4: molecular weight marker (Marker 4);
a: *Escherichia coli;*
b: *Mycobacterium tuberculosis;*
c: *Mycobacterium kansasii;*
d: *Mycobacterium marinum;*
e: *Mycobacterium simiae;*
f: *Mycobacterium scrofulaceum;*
g: *Mycobacterium gordonae;*
h: *Mycobacterium szulgai;*
i: *Mycobacterium avium;*
j: *Mycobacterium intracellulare;*
k: *Mycobacterium gastri;*
l: *Mycobacterium xenopi;*
m: *Mycobacterium nonchromogenicum;*
n: *Mycobacterium terrae;*
o: *Mycobacterium triviale;*
p: *Mycobacterium fortuitum;*
q: *Mycobacterium chelonei;*
r: *Mycobacterium abscessus;*
s: *Mycobacterium peregrinum.*

FIG. 7 shows the results of detection performed by the real-time PCR in Example 4, which is a standard curve drawn by plotting Ct value (Y-axis) for the copy number of genome (X-axis, logarithmic scale) of each DNA sample for PCR.

EXPLANATION OF LETTERS OR NUMERALS

In FIG. 5, each symbol indicates the following meaning:

(1): Candidate clone judged to have a high specificity for *M. kansasii;*

(2): The results obtained by use of KAS sequence of *M. kansasii* described in JP-A-11-155589;

(3): The results obtained by use of SEQ ID NO: 8 (identical with SEQ ID NO: 81 in this specification) derived from *M. tuberculosis* described in the description of JP Application No. 2004-129272.

(a): The line indicating:
Cy5/Cy3 ratio of fluorescent intensity ≧10.0;

(b): The line indicating:
Cy5/Cy3 ratio of fluorescent intensity ≧5.0;

(c): The line indicating:
Cy5/Cy3 ratio of fluorescent intensity ≧2.0;

(a'): The line indicating:
Cy3/Cy5 ratio of fluorescent intensity ≧10.0;

(b'): The line indicating:
Cy3/Cy5 ratio of fluorescent intensity ≧5.0;

(c'): The line indicating:
Cy3/Cy5 ratio of fluorescent intensity ≧2.0.

BEST MODE FOR CARRYING OUT THE INVENTION

In the present invention, *M. kansasii* gene refers to an arbitral unit of nucleotide sequence (a region) in the entire genome sequence owned by *Mycobacterium kansasii*. The entire genome sequencing of *M. kansasii* has not been completed yet.

An oligonucleotide of the present invention includes an oligonucleotide which comprises a part or the entire sequence of a nucleotide sequence depicted in SEQ ID NO: 1, SEQ ID NO: 2, SEQ ID NO: 3 or SEQ ID NO: 4 or a part or the entire sequence of a nucleotide sequence complementary to the nucleotide sequence, wherein the oligonucleotide is capable of hybridizing with a nucleotide sequence of *M. kansasii* gene (hereinafter, optionally briefly referred to as "the oligonucleotide of the present invention").

As to the size of the oligonucleotides of the present invention, an oligonucleotide having the nucleotide sequence depicted in SEQ ID NO: 1 has 517 bases; an oligonucleotide having the nucleotide sequence depicted in SEQ ID NO: 2 has 596 bases; an oligonucleotide having the nucleotide sequence depicted in SEQ ID NO: 3 has 636 bases; and an oligonucleotide having the nucleotide sequence depicted in SEQ ID NO: 4 has 726 bases.

The oligonucleotide which comprises a part or the entire sequence of the nucleotide sequence depicted in SEQ ID NO: 1, SEQ ID NO: 2, SEQ ID NO: 3 or SEQ ID NO: 4 of the present invention includes, for example, (1) an oligonucleotide which comprises a nucleotide sequence sharing homology with the oligonucleotide sequence depicted in SEQ ID NO: 1, SEQ ID NO: 2, SEQ ID NO: 3 or SEQ ID NO: 4 in about 70% or more, preferably about 80% or more, more preferably about 90% or more, yet more preferably about 95% or more, or (2) an oligonucleotide which comprises a consecutive 10 or more of bases, preferably 20 or more of bases among the sequence depicted in SEQ ID NO: 1, SEQ ID NO: 2, SEQ ID NO: 3 or SEQ ID NO: 4, or the like.

The oligonucleotide which comprises a part of the nucleotide sequence depicted in SEQ ID NO: 1, SEQ ID NO: 2, SEQ ID NO: 3 or SEQ ID NO: 4 include an oligonucleotide which comprises a part or the entire sequence of the nucleotide sequence depicted in SEQ ID NO: 5 to 79, and comprises 10 or more of consecutive bases, and the like.

A specific example of the oligonucleotide which comprises the part of the nucleotide sequence depicted in SEQ ID NO: 1 includes, for example, the oligonucleotide which comprises a sequence selected from the nucleotide sequence depicted in SEQ ID NO: 5 to 12 or SEQ ID NO: 53 to 56; a specific example of the oligonucleotide which comprises the part of the nucleotide sequence depicted in SEQ ID NO: 2 includes the oligonucleotide which comprises a sequence selected from the nucleotide sequence depicted in SEQ ID NO: 13 to 26 or SEQ ID NO: 57 to 64; a specific example of the oligonucleotide which comprises the part of the nucleotide sequence depicted in SEQ ID NO: 3 includes, for example, the oligonucleotide one which comprises a sequence selected from the nucleotide sequence depicted in SEQ ID NO: 27 to 40 or SEQ ID NO: 65 to 72; and a specific example of the oligonucleotide which comprises the part of the nucleotide sequence depicted in SEQ ID NO: 4 includes, for example, the oligonucleotide which comprises a sequence selected from the nucleotide sequence depicted in SEQ ID NO: 41 to 52 or SEQ ID NO: 73 to 79.

The oligonucleotide which comprises a part or the entire sequence of a nucleotide sequence complementary to the nucleotide sequence depicted in SEQ ID NO: 1, SEQ ID NO: 2, SEQ ID NO: 3 or SEQ ID NO: 4 of the present invention includes, for example, an oligonucleotide which comprises a part or the entire sequence of a nucleotide sequence being capable of hybridizing with the oligonucleotide which comprises the nucleotide sequence depicted in SEQ ID NO: 1, SEQ ID NO: 2, SEQ ID NO: 3 or SEQ ID NO: 4 of the present invention, and the like.

The above described oligonucleotide which comprises the part or the entire sequence of the nucleotide sequence being capable of hybridizing with the oligonucleotide which comprises the nucleotide sequence depicted in SEQ ID NO: 1, SEQ ID NO: 2, SEQ ID NO: 3 or SEQ ID NO: 4 of the present invention includes, in particular, an oligonucleotide which comprises a part or the entire sequence of the nucleotide sequence being capable of hybridizing under a high stringent condition or under a stringent condition with the oligonucleotide of the present invention which comprises the nucleotide sequence depicted in SEQ ID NO: 1, SEQ ID NO: 2, SEQ ID NO: 3 or SEQ ID NO: 4, and the like.

In this regard, "high stringent condition" means a condition that, specifically, for example, the hybridization is carried out in 50% formamide at 42 to 70° C., preferably at 60 to 70° C., and followed by washing in 0.1% sodium dodecyl sulfate (SDS) at 25 to 70° C. in 0.2 to 2×SSC.

In addition, "stringent condition" means a condition that, specifically, for example, the hybridization is carried out in 6×SSC or the hybridization solution with the equivalent salt concentration under the temperature of 50 to 70° C. for 16 hours, and then pre-washing, if needed, with 6×SSC or the solution with the equivalent salt concentration, and followed by washing with 1×SSC or the solution with the equivalent salt concentration and the like.

An oligonucleotide being capable of hybridizing with the nucleotide sequence of *M. kansasii* gene in the present invention includes an oligonucleotide which comprises a nucleotide sequence being capable of hybridizing under a high stringent condition or a stringent condition with the nucleotide sequence of *M. kansasii* gene as described above, and the like. The high stringent condition and the stringent condition are as described above.

The oligonucleotide which comprises the part of the nucleotide sequence complementary to the nucleotide sequence depicted in SEQ ID NO: 1, SEQ ID NO: 2, SEQ ID NO: 3 or SEQ ID NO: 4 includes "an oligonucleotide which comprises the part or the entire sequence of a nucleotide sequence complementary to an oligonucleotide which comprises the nucleotide sequence depicted in SEQ ID NO: 5 to 79, and 10 or more of consecutive bases".

The specific example of the oligonucleotide which comprises the part of the nucleotide sequence complementary to the nucleotide sequence depicted in SEQ ID NO: 1, SEQ ID NO: 2, SEQ ID NO: 3 or SEQ ID NO: 4 includes an oligonucleotide which comprises the nucleotide sequence complementary to the nucleotide sequence selected from the nucleotide sequence depicted in SEQ ID NO: 5 to 79.

In addition, the oligonucleotide of the present invention can be either deoxyribonucleic acid (DNA) or ribonucleic acid (RNA). In the case of ribonucleic acid, it goes without saying that thymidine residue (T) can be read as uridine (U) residue. In addition, the DNA comprising uridine residue synthesized by exchanging T at arbital position by U can be used. Also, the RNA comprising thymidine residue synthesized by exchanging U at arbitral position by T can be used. In addition, there can be deletion, insertion or replacement of one or plural number of nucleotide, or a modified nucleotide such as inosine (I).

To obtain the oligonucleotide of the present invention, the product prepared by chemical synthesis method well known per se can be used. It is, therefore, possible to obtain an oligonucleotide with constant quality easily, in large amount at low cost compared with a cloning method to obtain an oligonucleotide or a polynucleotide.

For example, using a DNA synthesizer usually used for DNA synthesis, an oligonucleotide is synthesized according to the conventional phosphoamidite method, and purified by the conventional method of the anion exchange column chromatography. And thus, an objective oligonucleotide of the present invention can be obtained.

Other means of screening an oligonucleotide which complies with the purpose of the present invention include the subtraction method as described in FEMS Microbiology Letters 166: 63-70, 1998 or Systematic and Applied Microbiology 24: 109-112, 2001. This is a methodology of concentrating a candidate sequence by subtracting nucleotide sequence which reacts with a fragment of genomic DNA derived form organism species to be differentiated.

In addition, as described in JP-A-11-155589 (Patent Document 1), an approach through preparing differential display of amplification products from the target genomic DNA and a genomic DNA derived from organism species to be differentiated, that is, the methodology by use of the arbitrarily primed polymerase chain reaction (AP-PCR) can be considered.

Further, by use of so called microarray method, the oligonucleotide of the present invention can also be obtained. That is, for example, a shotgun clone of *M. kansasii* genomic DNA is prepared, and then the purified DNA derived from the shotgun clone is arrayed onto a slide glass to form a microarray. On the side, a fluorescently labeled genomic DNA fragment of target *M. kansasii* (Label-1) is prepared. On the other hand, a fluorescently labeled genomic DNA fragment from the organism species to be differentiated (Label-2) is prepared separately and used for comparative experiment. That is, the reactivity (binding) of each Label-1 and Label-2 with the array on the microarray is assayed by competitive hybridization using Label-1 and Label-2 in the same reaction system. Hereby, this enables to select candidate sequence group which reactive more specifically with genomic DNA fragment (Label-1) from target *M. kansasii* (for example, Non-Patent Document 6 and the like), and thus the objective oligonucleotide can be selected. An example of the method of selecting oligonucleotide using microarray method of the present invention will be described in detail as follows.

(1) Preparation of Whole Genome Shotgun Library

The preparation of Whole Genome Shotgun library of *M. kansasii* is carried out by the modified method of the Whole Genome Shotgun method described by Venter et al., Science 2001 Feb. 16; 291 (5507): 1304-1351 as mentioned below.

Firstly, *M. kansasii* strain is treated by conventional procedures (for example, the fracturing treatment of bacterial body by autoclave treatment and using glass beads and the like), then extraction and purification of DNA is carried out according to the conventional procedures. The purified DNA sample obtained is subjected to DNA fragmentation treatment, for example, treatment for about 1 to 5 minutes using a nebulizer in the presence of 20% final concentration of glycerol under 5 kPa to 9 kPa. By this treatment, the objective size of 500 to 1000 bp fraction can be recovered efficiently. The fraction obtained is purified using a commercially available extraction column.

After that, the obtained fraction (DNA fragment) is incorporated into a vector DNA by ligation according to the conventional procedures to obtain a recombinant DNA (Whole Genome Shotgun library from *M. kansasii*). The vector to be used for this purpose includes, for example, in the case that the host cell for subsequent transformation is *E. Coli*, a vector such as pBS (e.g., pBSII sk+vector (Stratagene Corp.)), pQE-TRI plasmid (QIAGEN Inc.), pBluescript, pET, pGEM-3Z, pGEX and the like. Prior to ligation, the fragment is optionally blunt ended with DNA polymerase and the like.

Next, a suitable host cell is transformed to obtain a transformant using the obtained recombinant DNA. The host cell to be used for this purpose includes, for example, *E. coli*, preferably JM109, DH5α, TOP10 and the like. As a host cell, in addition to this, the competent cell having high transduction efficiency for plasmid and phage DNA can be used. For example, *E. coli* JM109 Competent Cells (Takara Bio Inc.) and the like are included.

The transformation can be carried out according to, for example, the D. M. Morrison's method (Method in Enzymology, 68, 326-331, 1979) and the like. In addition, when a commercially available competent cell is used, the transformation can be carried out according to the protocol provided in the product.

The means for the separation of transformant which has been introduced with a recombinant DNA into which the target DNA fragment has been incorporated includes, for example, a method of using properties of the vector to be used for the transduction. For example, if the vector containing ampicillin resistance gene is used, by culturing the transformant on a medium containing ampicillin and by selecting the grown clone, a library of the transformant (Whole Genome Shotgun clone of *M. kansasii* genome) which has been introduced with a recombinant DNA into which the target DNA fragment has been transducted can be obtained easily.

(2) Preparation of Microarray

The microarray is prepared by the following method.

That is, DNA is purified from the Whole Genome Shotgun clone derived from *M. kansasii* genome obtained in the above described (1) according to the conventional procedures, and then the DNA is suspended in the reaction solution for PCR and used as a sample for PCR. Using a suitable primer (it can be a commercially available primer, for example, M13 Primer M1 (Takara Bio Inc.) and M13 Primer RV (Takara Bio Inc.) and the like), the PCR is carried out according to the conventional procedure, and then the obtained PCR product is purified. After that, the PCR product is spotted on a slide glass for microarray; and is irradiated with 150 $mJ/cm^2$ of UV light to immobilize the PCR product onto the slide glass; and thus the microarray is produced.

Also, if needed, using, for example, a DNA sequence specific to tuberculosis bacterium such as *M. tuberculosis* (*Mycobacterium tuberculosis*: human type tuberculosis bacterium) and the like and a DNA sequence specific to *M. kansasii* genome and the like as a positive control, and using, for example, a DNA derived from *E. coli* and the like as a negative control, fragmentation of each DNA; ligation to vector; transformation of *E. coli*; DNA amplification by PCR; immobilization of PCR product onto a slide glass are carried out equally for each DNA, and prepared respective microarrays.

(3) Fluorescent Dye Labeling on the Target Genomic DNA

Differently, genomic DNA extracted and purified from *M. kansasii* strain and a comparative DNA (for example, a DNA derived from tuberculosis bacterium such as bovine type tuberculosis bacterium and the like) are labeled respectively with Cy3 and Cy5 by indirect labeling method using hexylamino-UTP.

The process will be explained by taking, for example, a modified indirect labeling method of a protocol published by DeRisi Laboratory (www.microarray.org) as an example. In this method, using αUTP having an amino group, and incorporating it into a molecule by enzymatic extension reaction, the αUTP-incorporated DNA chain is produced. Then, the DNA is labeled by binding fluorescent dye (succinimide body) chemically with the amino group of the DNA.

Firstly, the starting material (*M. kansasii*-derived genomic DNA and comparative genomic DNA) is denatured by heating according to the conventional procedure (a commercially available kit such as BioPrime DNA labeling system (Invitrogen Co.) con be used). In the next place, after addition of 2 μl DTT, a mixed solution of dATP/dCTP/dGTP, dTTP, Ha-dUTP and Klenow enzyme, the extension reaction is carried out at 37° C. for about 3 hours. The obtained reaction product is placed onto an ultrafiltration column and centrifuged at 14,000 rpm for about 4 minutes, and the concentrated solution is recovered in a microtube, and then dried thoroughly using a centrifugal vacuum drier and the like. After that, above dried reaction product is added with $NaHCO_3$ and mixed, and stand at room temperature for 2 to 3 minutes.

Separately, a solution of Cy3 (or Cy5) dissolved in DMSO is prepared (Cy-dye Solution Cy3, Cy-dye Solution Cy5). This Cy-dye Solution Cy3 is added to the above-described reaction product obtained by using of comparative genomic DNA, and the Cy-dye Solution Cy5 is added to the above described reaction product obtained by using *M. kansasii* genomic DNA, and each mixture is incubated (under light shielding) at 40° C. for about 60 minutes. Further, each reaction product is added with 4 M $NH_2OH$ (prepared just before use) and mixed, and is incubated (under light shielding) for about 15 minutes to obtain the labeled product for each genomic DNA. After that, the obtained labeled product is placed onto an ultrafiltration column and centrifuged at 14,000 rpm for about 4 minutes, and the concentrated solution is recovered in a microtube, and then dried thoroughly using a centrifugal vacuum drier.

The obtained labeled product of each genomic DNA in dry state is suspended and mixed in a solution with a composition of final concentrations of 0.04 M Tris-acetate (pH 8.1), 0.1 M potassium acetate, and 0.03 M magnesium acetate tetrahydrate. The suspension is heat-treated at 94° C. for 15 minutes, and the fragmentation product of each labeled genomic DNA with 100 to 300 bases is obtained (Cy3-labeled product, Cy5-labeled product).

Each Cy3-labeled product and Cy5-labeled product is placed separately onto an ultrafiltration column and centrifuged at 14,000 rpm for about 4 minutes, and each concentrated solution is recovered in a microtube, and then dried thoroughly using a centrifugal vacuum drier.

To a microtube, 40 μl of salmon sperm DNA (10 mg/ml) and 0.5 μl of a reagent solution prepared by adjusting 5 μl of formamide to make the total volume of 40 to 50 μl using ArrayHyb Hybridization buffer (SIGMA) (composition in a case when the slide glass for the microarray to be used in later is 24×55 mm) are placed, and the above obtained Cy3-labeled product and Cy5-labeled product are mixed in suspension in the same solution and incubated at 95° C. for 5 minutes to obtain a solution of Cy3Cy5 labeled product. This solution is kept at 70° C. until it is used for the microarray hybridization in the following section (4).

(4) Microarray Hybridization (DNA-DNA Hybridization on an Array)

On a microarray (DNA chip) prepared in the above-described (2), a whole solution of mixture of Cy3Cy5-labeled product prepared in the above described (3) is placed, and covered with a cover glass keeping no air bubble inside. The microarray is set on a Hybri-cassette (a hybridization cassette); placed in a Tupperware matted with a Kim Towel (Nippon Paper Crecia Co., Ltd.) wetted by distilled water and closed tightly; and reacted (under light shielding) at 65° C. for 8 hours or more to allow hybridization. After hybridization, the microarray is soaked in a 2×SSC-0.1% SDS solution together with cover glass at room temperature, and shake gently in the solution to remove the cover glass. After sequential washing with 1×SSC and 0.03% SDS solution (60° C.) for 10 minutes, 0.2×SSC solution (42° C.) for 10 minutes and 0.05×SSC solution (room temperature) for 10 minutes, the microarray is transferred quickly to a new dry rack, and dried immediately by centrifugation at 800 rpm for 5 minutes.

(5) Measurement of Fluorescent Intensity: from Signal Detection to Quantification Using a fluorescence readout scanner, 2-channel fluorescent intensities of Cy3 and Cy5 on the microarray, on which the microarray hybridization has been performed as described in above (4), are measured to obtain fluorescence detection data. The quantification of fluorescence signal is performed using commercially available DNA chip expression image analysis software, and automatic spot recognition, background calculation, and normalization of fluorescent intensity ratio can be carried out according to the operation procedure of the software.

The Cy5 labeled product used for hybridization is the labeled genome derived from *M. kansasii*, and the Cy3 labeled product is the labeled comparative genomic DNA. Therefore, when the fluorescent intensity of each Cy3 and Cy5 is measured and the fluorescent intensity of Cy5 is detected stronger, it means that the subject PCR product on the microarray hybridizes with *M. kansasii*, and is judged to have high specificity for *M. kansasii*. On the other hand, when the fluorescent intensity of Cy3 is detected stronger, it means that the subject PCR product on the microarray hybridizes with the comparative genomic DNA, and in addition, when the fluorescent intensity of Cy3 and Cy5 are detected in the same level of intensity, or any fluorescent signal of both Cy3 and Cy5 is detected, it can be judged that the specificity for *M. kansasii* is low.

It should be noted that if a positive control (for example, specific DNA fragment for *M. tuberculosis*, specific DNA fragment for *M. kansasii* and the like) and a negative control (for example, DNA fragment derived from *E. coli* and the like) are spotted on the microarray, the tendency of the fluorescent intensity obtained by measuring fluorescent intensity of Cy3Cy5 of each spot can be utilized as a standard for the evaluation of data produced in the scanning fluorescence measurement.

In addition, for the purpose of screening a candidate sequence for use in detecting *M. kansasii* specifically, based on the Cy3/Cy5 fluorescent intensity ratio (Ratio) detected on the DNA chip scatter plot is made, and analysis is carried out as follows:

In the analysis, among the positive control sequences used, the value of the Cy3/Cy5 Ratio of the DNA fragment specific to *M. kansasii* will be a useful standard value for the evaluation of specificity. That is, among the candidates which have been screened, the clones which provide significantly specific signal for *M. kansasii* (i.e. fluorescent intensity of Cy5 is strong) as the result of the analysis of Cy3/Cy5 Ratio value, and yet provide a large value of the Ratio compared with the positive control of specific spot to *M. kansasii* is selected.

Further, determination of the nucleotide sequence of the obtained candidate clone can be carried out according to the conventional procedures using equipment such as, for example, ABI PRISM310 capillary sequencer (Applied Biosystems).

A primer for the detecting *M. kansasii* in the present invention includes the primer that comprises an oligonucleotide which comprises a part or the entire sequence of the nucleotide sequence depicted in SEQ ID NO: 1, SEQ ID NO: 2, SEQ ID NO: 3 or SEQ ID NO: 4 or a part or the entire sequence of a nucleotide sequence complementary to the nucleotide sequence, wherein the oligonucleotide is capable of hybridizing with a nucleotide sequence of *M. kansasii* gene (hereinafter, optionally referred to as the primer of the present invention).

In addition, in compliance with the conditions of PCR, nucleotide hybridization and the like, the primer of the present invention can be used by selecting an appropriate length in a proper region in consideration of dissociation temperature (Tm value) and the like from the oligonucleotides which comprises a part or the entire sequence of the nucleotide sequence depicted in SEQ ID NO: 1 to 4, or a part or the entire sequence of a nucleotide sequence complementary to the nucleotide sequence. Preferably, the length of primer is 10 to 50 bases which are considered necessary base number for retaining specificity as a primer, more preferably 10 to 35 bases, yet more preferably 18 to 25 bases.

As to the method of designing primer, the primer can be designed using software commonly used for designing primer such as, for example, a web tool for primer design, Primer 3 (Whitehead Institute for Biomedical Research) and the like.

A specific example of the oligonucleotide to be used for the primer of the present invention (the oligonucleotide of the present invention) which comprises the part or the entire sequence of the nucleotide sequence depicted in SEQ ID NO: 1, SEQ ID NO: 2, SEQ ID NO: 3 or SEQ ID NO: 4, or the part or the entire sequence of the nucleotide sequence complementary to the nucleotide sequence, wherein the oligonucleotide is capable of hybridizing with the nucleotide sequence of *M. kansasii* gene is the same as described in the above explanation of the oligonucleotide of the present invention.

Specific examples of such primer include, for example, the primer that comprises an oligonucleotide which comprises a part or the entire sequence of the nucleotide sequence depicted in SEQ ID NO: 5 to 52 or a part or the entire sequence of a nucleotide sequence complementary to the nucleotide sequence, wherein the oligonucleotide is capable of hybridizing with the nucleotide sequence of *M. kansasii* gene.

A more preferable example of the primer of the present invention includes the one which comprises a sequence selected from a nucleotide sequence depicted in SEQ ID NO: 5 to 52 or the one which comprises a nucleotide sequence complementary to the nucleotide sequence selected from the nucleotide sequence depicted in SEQ ID NO: 5 to 52. Among them, a primer which comprises a sequence selected from the nucleotide sequence depicted in SEQ ID NO: 5, 6, 13 to 16, 27 to 30, and 41 to 44 or a nucleotide sequence complementary to the nucleotide sequence selected from the nucleotide sequence depicted in SEQ ID NO: 5, 6, 13 to 16, 27 to 30, and 41 to 44 is included.

It should be noted that the primer having a nucleotide sequence depicted in SEQ ID NO: 5 to 12 is designed based on the nucleotide sequence depicted in SEQ ID NO: 1. The primer having a nucleotide sequence depicted in SEQ ID NO: 13 to 26 is designed based on the nucleotide sequence depicted in SEQ ID NO: 2. The primer having a nucleotide sequence depicted in SEQ ID NO: 27 to 40 is designed based on the nucleotide sequence depicted in SEQ ID NO: 3. The primer having a nucleotide sequence depicted in SEQ ID NO: 41 to 52 is designed based on the nucleotide sequence depicted in SEQ ID NO: 4.

In FIG. 1, in the nucleotide sequence depicted in SEQ ID NO: 1, the location of the primer having nucleotide sequence depicted in SEQ ID NO: 5 and 6 is each indicated as 1c_plate1_Fw1 and 1c_plate1_Rv1 by arrow.

In FIG. 2, in the nucleotide sequence depicted in SEQ ID NO: 2, the location of the primer having nucleotide sequence depicted in SEQ ID NO: 13, 14, 15 and 16 is each indicated as 6c_plate1_Fw1, 6c_plate1_Rv1, 6c_plate1_Fw2 and 6c_plate1_Rv2 by arrow.

In FIG. 3, in the nucleotide sequence depicted in SEQ ID NO: 3, the location of the primer having nucleotide sequence depicted in SEQ ID NO: 27, 28, 29 and 30 is each indicated as 8d_plate1_Fw1, 8d_plate1_Rv1, 8d_plate1_Fw2 and 8d_plate1_Rv2 by arrow.

In FIG. 4, in the nucleotide sequence depicted in SEQ ID NO: 4, the location of the primer having nucleotide sequence depicted in SEQ ID NO: 41, 42, 43 and 44 is each indicated as 9c_plate1_Fw1, 9c_plate1_Rv1, 9c_plate1_Fw2 and 9c_plate1_Rv2 by arrow.

In addition, in the nucleotide sequence depicted in SEQ ID NO: 1, the location of the primer having the nucleotide sequence depicted in SEQ ID NO: 7 to 12 is each indicated as follows:

```
SEQ ID NO: 7  (1c_plate1_Fw3): base No. 33 to 51;
SEQ ID NO: 8  (1c_plate1_Fw4): base No. 212 to 231;
SEQ ID NO: 9  (1c_plate1_Fw5): base No. 315 to 334;
SEQ ID NO: 10 (1c_plate1_Rv3): base No. 185 to 204;
SEQ ID NO: 11 (1c_plate1_Rv4): base No. 411 to 430;
SEQ ID NO: 12 (1c_plate1_Rv5): base No. 461 to 481.
```

In the nucleotide sequence depicted in SEQ ID NO: 2, the location of the primer having the nucleotide sequence depicted in SEQ ID NO: 17 to 26 is each indicated as follows:

```
SEQ ID NO: 17 (6c_plate1_Fw3): base No. 4 to 21;
SEQ ID NO: 18 (6c_plate1_Fw4): base No. 48 to 67;
SEQ ID NO: 19 (6c_plate1_Fw5): base No. 229 to 247;
SEQ ID NO: 20 (6c_plate1_Fw6): base No. 279 to 296;
SEQ ID NO: 21 (6c_plate1_Fw7): base No. 380 to 399;
SEQ ID NO: 22 (6c_plate1_Rv3): base No. 166 to 184;
SEQ ID NO: 23 (6c_plate1_Rv4): base No. 195 to 214;
SEQ ID NO: 24 (6c_plate1_Rv5): base No. 368 to 387;
SEQ ID NO: 25 (6c_plate1_Rv6): base No. 428 to 445;
SEQ ID NO: 26 (6c_plate1_Rv7): base No. 523 to 542.
```

In the nucleotide sequence depicted in SEQ ID NO: 3, the location of the primer having the nucleotide sequence depicted in SEQ ID NO: 31 to 40 is each indicated as follows:

```
SEQ ID NO: 31 (8d_plate1_Fw3): base No. 5 to 22;
SEQ ID NO: 32 (8d_plate1_Fw4): base No. 54 to 72;
SEQ ID NO: 33 (8d_plate1_Fw5): base No. 207 to 226;
SEQ ID NO: 34 (8d_plate1_Fw6): base No. 289 to 308;
```

-continued

```
SEQ ID NO: 35 (8d_plate1_Fw7): base No. 472 to 490;
SEQ ID NO: 36 (8d_plate1_Rv3): base No. 151 to 169;
SEQ ID NO: 37 (8d_plate1_Rv4): base No. 220 to 239;
SEQ ID NO: 38 (8d_plate1_Rv5): base No. 335 to 353;
SEQ ID NO: 39 (8d_plate1_Rv6): base No. 408 to 427;
SEQ ID NO: 40 (8d_plate1_Rv7): base No. 616 to 635.
```

In the nucleotide sequence depicted in SEQ ID NO: 4, the location of the primer having the nucleotide sequence depicted in SEQ ID NO: 45 to 52 is each indicated as follows:

```
SEQ ID NO: 45 (9c_plate1_Fw3): base No. 17 to 36;
SEQ ID NO: 46 (9c_plate1_Fw4): base No. 117 to 135;
SEQ ID NO: 47 (9c_plate1_Fw5): base No. 405 to 424;
SEQ ID NO: 48 (9c_plate1_Fw6): base No. 492 to 512;
SEQ ID NO: 49 (9c_plate1_Rv3): base No. 182 to 201;
SEQ ID NO: 50 (9c_plate1_Rv4): base No. 263 to 281;
SEQ ID NO: 51 (9c_plate1_Rv5): base No. 528 to 547;
SEQ ID NO: 52 (9c_plate1_Rv6): base No. 654 to 673.
```

It should be noted that in the above description, the name of the primer denominated in the present invention is shown in parenthesis next to SEQ ID NO.

The method of obtaining the primer of the present invention is as described in the method of obtaining a nucleotide of the present invention.

In addition, the primer of the present invention can be labeled with a labeling substance.

The labeling substance to be used for labeling the primer of the present invention can be used any of the well known labeling substances such as a radioisotope, an enzyme, a fluorescent substance, a luminescent substance, biotin and the like.

For example, the radioisotope such as $^{32}P$, $^{33}P$, $^{35}S$ and the like, the enzyme such as alkaline phosphatase, horseradish peroxydase and the like, the fluorescent substance such as cyanine dye group of Cy3, Cy5 (Amersham Biosciences), fluorescein and the like, the luminescent substance such as chemoluminescent reagent including acridinium ester and the like are included.

When the primer of the present invention is labeled with radioisotope, a method of labeling by incorporation of a radioisotope-labeled nucleotide into the primer at the time when the primer is synthesized, or a method of labeling with radioisotope after the primer is synthesized or the like are included. Specifically, a frequently-used random primer method, nick-translation method, 5'-terminal labeling method using T4 polynucleotide kinase, 3'-terminal labeling method using terminal deoxynucleotidyl transferase and RNA labeling method are included.

When the primer of the present invention is labeled with an enzyme, the conventional technique in this field of direct labeling method by which the primer to be labeled is directly linked covalently with an enzyme molecule such as alkaline phosphatase, horseradish peroxidase or the like can be employed.

When the primer of the present invention is labeled with fluorescent substance, for example, the fluorescently-labeled nucleotide can be incorporated into the primer by conventional labeling technique in this field. In addition, by a method of replacing a sequence with a nucleotide having a linker arm as a member of a oligonucleotide (See, for example, Nucleic Acids Res., 1986, vol. 14, p. 6115), the nucleotide can also be labeled with the fluorescent substance. In that case, there can also be a method that a uridine having a linker arm on 5-position is synthesized chemically from a deoxyuridine by a synthetic method disclosed in JP-A-1985-500717 and then a fluorescent substance is introduced into the above-described oligonucleotide.

In the methods of labeling with a luminescent substance and with biotin, the labeling can be carried out according to the conventional technique of luminescent-labeling or biotin-labeling of nucleotide usually conducted in this field.

A probe for detecting *M. kansasii* in the present invention includes the probe that comprises an oligonucleotide which comprises a part or the entire sequence of the nucleotide sequence depicted in SEQ ID NO: 1, SEQ ID NO: 2, SEQ ID NO: 3 or SEQ ID NO: 4, or a part or the entire sequence of a nucleotide sequence complementary to the nucleotide sequence, wherein the oligonucleotide is capable of hybridizing with the nucleotide sequence of *M. kansasii* gene (hereinafter, optionally referred to as the probe of the present invention).

A specific example of the oligonucleotide to be used for the probe of the present invention (the oligonucleotide of the present invention) which comprises the part or the entire sequence of the nucleotide sequence depicted in SEQ ID NO: 1, SEQ ID NO: 2, SEQ ID NO: 3 or SEQ ID NO: 4, or the part or the entire sequence of the nucleotide sequence complementary to the nucleotide sequence, wherein the nucleotide is capable of hybridizing with the nucleotide sequence of *M. kansasii* gene is the same as described in the above explanation of the oligonucleotide of the present invention.

In compliance with the conditions of PCR, nucleotide hybridization and the like, the probe of the present invention can be used by selecting an appropriate length in a proper region in calculation of dissociation temperature (Tm value) and the like from the oligonucleotide which comprises a part or the entire sequence of the nucleotide sequence depicted in SEQ ID NO: 1 to 4, or a part or the entire sequence of a nucleotide sequence complementary to the nucleotide sequence. It is desirable to design the probe in consideration of the base number necessary for retaining specificity as a probe if the probe is intended to have sufficient specificity.

For example, the probe to be used for nucleotide hybridization method (for example, Southern hybridization and the like) includes a probe having the base length of 10 to 700 bases, preferably 100 to 600 bases and further preferably 200 to 500 bases.

In addition, for example, the probe to be used for the real-time PCR system (for example, TaqMan™ method, Molecular Beacon method and the like) includes the one having the base length of 10 to 50 bases, preferably 15 to 40 bases and further preferably 20 to 30 bases.

Specific example of such probe include, for example, the one selected from the probe that comprises an oligonucleotide which comprises a part or the entire sequence of the nucleotide sequence depicted in SEQ ID NO: 5 to 79 or a part or the entire sequence of a sequence complementary to the nucleotide sequence, wherein the oligonucleotide is capable of hybridizing with the nucleotide sequence of *M. kansasii* gene.

A preferable example of the probe of the present invention includes the one which comprises a sequence selected from the nucleotide sequence depicted in SEQ ID NO: 5 to 79. Among them, the probe which comprises a sequence selected from nucleotide sequence depicted in SEQ ID NO: 5, 6, 13 to 16, 27 to 30, 41 to 44, 53, 57 to 59, 65 to 67, 73 to 75 are preferable. Particularly, the probe which comprises a sequence selected from the nucleotide sequence depicted in SEQ ID NO: 53, 57 to 59, 65 to 67, 73 to 75 are preferable.

It should be noted that the nucleotide sequence depicted in SEQ ID NO: 53 to 79' is the one to be amplified by the PCR using the primer of the present invention. The combination of a forward primer and a reverse primer, and SEQ ID NO of the nucleotide to be amplified by the PCR using these primers are shown collectively in Table 1. The table shows that, for example, the nucleotide sequence depicted in SEQ ID NO: 53 is a sequence which is amplified by the PCR using an oligonucleotide with nucleotide sequence depicted in SEQ ID NO: 5 as a forward primer and an oligonucleotide with nucleotide sequence depicted in SEQ ID NO: 6 as a reverse primer.

TABLE 1

| Forward primer | Reverse primer | Amplified sequence |
|---|---|---|
| 5 | 6 | 53 |
| 7 | 10 | 54 |
| 8 | 11 | 55 |
| 9 | 12 | 56 |
| 13 | 14 | 57 |
| 15 | 16 | 58 |
| 13 | 16 | 59 |
| 17 | 22 | 60 |
| 18 | 23 | 61 |
| 19 | 24 | 62 |
| 20 | 25 | 63 |
| 21 | 26 | 64 |
| 27 | 28 | 65 |
| 29 | 30 | 66 |
| 27 | 30 | 67 |
| 31 | 36 | 68 |
| 32 | 37 | 69 |
| 33 | 38 | 70 |
| 34 | 39 | 71 |
| 35 | 40 | 72 |
| 41 | 42 | 73 |
| 43 | 44 | 74 |
| 41 | 44 | 75 |
| 45 | 49 | 76 |
| 46 | 50 | 77 |
| 47 | 51 | 78 |
| 48 | 52 | 79 |

The method of obtaining the probe of the present invention is as described in the method of obtaining a nucleotide of the present invention.

The probe of the present invention can be labeled with a labeling substance.

The labeling substance to be used for labeling the probe of the present invention can be used any of the well known labeling substances such as radioisotope and enzyme, fluorescent substance, luminescent substance, biotin and the like.

A specific example of the labeling substance and the labeling method to be used for labeling the probe of the present invention are as described in the explanation of labeling method of the primer of the present invention.

The labeled probe to be used in the real-time PCR method as described later includes the probe of the present invention labeled with a labeling substance usually used in the real-time detection method. For example, the labeled probe of the present invention in which the 5'-terminal is labeled with a reporter fluorescent substance (carboxyfluorescein (FAM), hexachlorofluorescein (HEX), tetrachlorofluorescein (TET) and the like) and the 3'-terminal is labeled with a quencher dye (for example, a fluorescent substance such as carboxytetramethylrhodamine (TAMRA), nonfluorescent substance such as Black Hole Quencher dye (BHQ) and 4-((4-(dimethylamino) phenyl)azo)benzoic acid (DABCYL) is included.

The sample to be used for detecting *M. kansasii* involved in the present invention includes clinical specimen such as sputum, blood, pharyngeal mucosa, gastric juice, bronchial washing fluid, transbronchial specimen, puncture fluid such as pleural effusion and pus. In addition, the sample can be cultured bacterial body isolated from a specimen, nucleic acid isolated and purified from such bacterial body, or nucleic acid amplified by a nucleic acid amplification detection system and the like.

To extract and purify DNA from the above-described samples, the extraction and purification can be carried out according to the conventional procedures usually used for the extraction of acid-fast bacterium (tuberculosis bacterium) DNA from a material specimen.

In the case when the bacterial body is used as a sample, for example, the method of disrupting membrane structure of tuberculosis bacterium by treating the bacterial body with protein denaturing agent, for example, surface activating agent such as SDS, guanidine thiocyanate (GTC) and the like and the method of physical disruption of the bacterial body using glass beads and the like are included.

In the case when the expectorated sputum is used as a sample, in compliance with the recommendation from Center for Disease Control and Prevention (CDC), homogenization of the specimen material can be carried out, as pretreatment, by NALC (N-acetyl-L-cysteine)-NaOH method (Kent P T, Kubica G P, Pubric Health Mycobacteriology, A Guide for the Level III Laboratory, U.S. Department of Health and Human Services, Public Health Service, Center for Disease Control, Atlanta, U.S.A., 1985, p. 31-55).

After that, by the general method for the preparation of DNA (phenol-chloroform extraction method, ethanol precipitation method and the like, as described in Rapid and simple method for purification of nucleic acids, J. Clin. Microbiol., 1990, March; 28(3), 495-503, Boom R, Sol C J, Salimans M M, Jansen C L, Wertheim-van Dillen P M, van der Noordaa J), extraction and purification of DNA can be carried out.

Taking the case that the cultured bacterial body isolated from specimen is used as a sample as an example, colonies on the Ogawa's medium is recovered; suspended in sterile distilled water; centrifuged to collect bacterial body; the bacterial body is resuspended in distilled water and autoclaved; after disruption treatment (physical disruption using glass beads and the like), the disrupted bacterial body is further centrifuged to recover supernatant fluid. The DNA can be extracted and purified from the obtained supernatant fluid. As to the extraction of DNA, as various kits are commercially available, such kit can be utilized for this purpose, or the extraction can be carried out according to the conventional procedures in this field (for example, the phenol-chloroform extraction method, a method of precipitation using ethanol, propanol and the like). For example, using an ion-exchange resin type DNA extraction and purification kit Genomic-tip (QIAGEN GmbH) and the like, the extraction and purification of the DNA can be performed.

The detection method of *M. kansasii* involved in the present invention includes, for example:

(A) A method using an oligonucleotide (the oligonucleotide of the present invention) which comprises a part or the entire sequence of the nucleotide sequence depicted in SEQ ID NO: 1, SEQ ID NO: 2, SEQ ID NO: 3 or SEQ ID NO: 4, or a part or the entire sequence of a nucleotide sequence complementary to the nucleotide sequence, wherein the oligonucleotide is capable of hybridizing with the nucleotide sequence of *Mycobacterium kansasii* gene;

(B) A method using a labeled oligonucleotide of the present invention as a labeled probe. Each method will be explained below.

(A) A Method Using the Oligonucleotide of the Present Invention as a Primer

As the method (A), "a method in which, the nucleic acid amplification reaction is performed using the primer of the present invention, and using a nucleic acid in a sample as a template, and the obtained primer extension product is detected" is included. Specifically, for example, a method in which, using the primer of the present invention, the primer is hybridized with a nucleic acid in the sample, then the nucleic acid amplification by DNA polymerase and the like [for example, PCR; Patent Document 3, LAMP (Loop-mediated Isothermal Amplification) method (Tsugunori Notomi et al., Nucleic Acid Res., 28, e63, 2000), ICAN (Isothermal and Chimeric primer-initiated Amplification of Nucleic acids) method (Clinical Pathology, 51(11), 1061-1067, 2003, November), LCR (ligase chain reaction) method (JP-A-4-211399), SDA (strand displacement amplification) method (JP-A-8-19394)] is carried out to achieve primer extension is included. And, by this method, the sequence of the specific region of the nucleotide sequence of *M. kansasii* gene can be amplified, and thus *M. kansasii* can be detected by measuring the obtained primer extension product.

The specific example of the primer of the present invention to be used in the PCR is as described above.

Preferably, a forward primer includes an oligonucleotide which comprises a part or the entire sequence of the nucleotide sequence depicted in SEQ ID NO: 5, 7 to 9, 13, 15, 17 to 21, 27, 29, 31 to 35, 41, 43, 45 to 48 or a part or the entire sequence of a nucleotide sequence complementary to the nucleotide sequence, wherein the oligonucleotide is capable of hybridizing with the nucleotide sequence of *M. kansasii* gene, and a reverse primer includes an oligonucleotide which comprises a part or the entire sequence of the nucleotide sequence depicted in SEQ ID NO: 6, 10 to 12, 14, 16, 22 to 26, 28, 30, 36 to 40, 42, 44, 49 to 52 or a part or the entire sequence of a nucleotide sequence complementary to the nucleotide sequence, wherein the oligonucleotide is capable of hybridizing with the nucleotide sequence of *M. kansasii* gene More preferably, the forward primer includes the one which comprises a sequence selected from the nucleotide sequence depicted in SEQ ID NO: 5, 7 to 9, 13, 15, 17 to 21, 27, 29, 31 to 35, 41, 43, 45 to 48, and the reverse primer includes the one which comprises a sequence selected from the nucleotide sequence depicted in SEQ ID NO: 5, 10 to 12, 14, 16, 22 to 26, 28, 30, 36 to 40, 42, 44, 49 to 52.

Still preferably, the forward primer includes the one which comprises a sequence selected from the nucleotide sequence depicted in SEQ ID NO: 5, 13, 15, 27, 29, 41, 43, and the reverse primer includes the one which comprises a sequence selected from the nucleotide sequence depicted in SEQ ID NO: 6, 14, 16, 28, 30, 42, 44.

The preferable combination of the forward primer and the reverse primer includes the combination as described above in Table 1.

Among them, a particularly preferable combination of the forward primer and the reverse primer includes:

(1) A combination in which the forward primer is an oligonucleotide comprising the nucleotide sequence depicted in SEQ ID NO: 5 and the reverse primer is an oligonucleotide comprising the nucleotide sequence depicted in SEQ ID NO: 6;

(2) A combination in which the forward primer is an oligonucleotide comprising the nucleotide sequence depicted in SEQ ID NO: 13 and the reverse primer is an oligonucleotide comprising the nucleotide sequence depicted in SEQ ID NO: 14;

(3) A combination in which the forward primer is an oligonucleotide comprising the nucleotide sequence depicted in SEQ ID NO: 15 and the reverse primer is an oligonucleotide comprising the nucleotide sequence depicted in SEQ ID NO: 16;

(4) A combination in which the forward primer is an oligonucleotide comprising the nucleotide sequence depicted in SEQ ID NO: 13 and the reverse primer is an oligonucleotide comprising the nucleotide sequence depicted in SEQ ID NO: 16;

(5) A combination in which the forward primer is an oligonucleotide comprising the nucleotide sequence depicted in SEQ ID NO: 27 and the reverse primer is an oligonucleotide comprising the nucleotide sequence depicted in SEQ ID NO: 28;

(6) A combination in which the forward primer is an oligonucleotide comprising the nucleotide sequence depicted in SEQ ID NO: 29 and the reverse primer is an oligonucleotide comprising the nucleotide sequence depicted in SEQ ID NO: 30;

(7) A combination in which the forward primer is an oligonucleotide comprising the nucleotide sequence depicted in SEQ ID NO: 27 and the reverse primer is an oligonucleotide comprising the nucleotide sequence depicted in SEQ ID NO: 30;

(8) A combination in which the forward primer is an oligonucleotide comprising the nucleotide sequence depicted in SEQ ID NO: 41 and the reverse primer is an oligonucleotide comprising the nucleotide sequence depicted in SEQ ID NO: 42;

(9) A combination in which the forward primer is an oligonucleotide comprising the nucleotide sequence depicted in SEQ ID NO: 43 and the reverse primer is an oligonucleotide comprising the nucleotide sequence depicted in SEQ ID NO: 44;

(10) A combination in which the forward primer is an oligonucleotide comprising the nucleotide sequence depicted in SEQ ID NO: 41 and the reverse primer is an oligonucleotide comprising the nucleotide sequence depicted in SEQ ID NO: 44.

Conditions, operation method and the like of the PCR by using the above-described primer can be in accordance with the conventional routine procedures usually used in this field.

A method of determining the primer extension product includes, (A-1) a method in which the determination is performed based on the results of electrophoresis of the primer extension product obtained by the polymerase chain reaction, (A-2) a method in which the determination is performed by the real-time PCR method, and (A-3) a method in which the determination is performed by measuring the signal derived from the primer extension product obtained by the polymerase chain reaction using a labeled primer.

Each method will be explained in the followings.

(A-1) A Method in which the Determination is Performed Based on the Results of Electrophoresis of the Primer Extension Product Obtained by the Polymerase Chain Reaction This method includes, for example, "a method for detecting *M. kansasii* which comprises the following process:

(i) performing PCR using as a primer an oligonucleotide comprising a part or the entire sequence of the nucleotide sequence depicted in SEQ ID NO: 1, SEQ ID NO: 2, SEQ ID NO: 3 or SEQ ID NO: 4, or a part or the entire sequence of a nucleotide sequence complementary to the nucleotide sequence, wherein the oligonucleotide is capable of hybridizing with the nucleotide sequence of *M. kansasii* gene (the primer of the present invention), and using a nucleic acid in the sample as a template is carried out;

(ii) performing electrophoresis of the primer extension product obtained in above (i), and detecting *M. kansasii* on the basis of the obtained result".

A method for detecting *M. kansasii* from the results of electrophoresis includes, for example, (A-1-1) a method in which the determination is made by confirming a fraction of the primer extension product having objective size (number of base pair), (A-1-2) a method in which the determination is made by hybridization using a labeled probe, and the like.

Conditions, operation method and the like of the electrophoresis can be worked out according to the conventional procedures usually performed in this field.

(A-1-1) A Method in which the Determination is Made by Confirming a Fraction of the Primer Extension Product with Intended Number of Base Pair As to the above described method in which the determination is made by confirming a fraction of the primer extension product having objective size (number of base pair), for example, at first the PCR is carried out, then the obtained primer extension product is subjected to the electrophoresis. Size (number of base pair) of the amplification product is estimated in advance from both the forward primer and the reverse primer to be used for the PCR, and based on that, the confirmation of whether or not the obtained fraction of electrophoresis corresponds to the estimated size of the amplification product can be carried out by the conventional procedures. A detection method based on the characteristic size of the amplification product measured, for example, by such a way that the type of nucleic acid is visualized by staining with ethidium bromide and the like, is included.

A specific determination method according to the method of (A-1-1) includes, for example, the following methods:

(1) A method in which, after performing PCR using an oligonucleotide comprising the nucleotide sequence depicted in SEQ ID NO: 5 as a forward primer and an oligonucleotide comprising the nucleotide sequence depicted in SEQ ID NO: 6 as a reverse primer, the obtained primer extension product is subjected to electrophoresis, and the one in which a fraction of 167 base pairs or a fraction of an oligonucleotide comprising the nucleotide sequence depicted in SEQ ID NO: 56 is confirmed is determined to be positive.

(2) A method in which, after performing PCR using an oligonucleotide comprising the nucleotide sequence depicted in SEQ ID NO: 7 as a forward primer and an oligonucleotide comprising the nucleotide sequence depicted in SEQ ID NO: 10 as a reverse primer, the obtained primer extension product is subjected to electrophoresis, and the one in which a fraction of an oligonucleotide comprising the nucleotide sequence depicted in SEQ ID NO: 54 is confirmed is determined to be positive.

(3) A method in which, after performing PCR using an oligonucleotide comprising the nucleotide sequence depicted in SEQ ID NO: 8 as a forward primer and an oligonucleotide comprising the nucleotide sequence depicted in SEQ ID NO: 11 as a reverse primer, the obtained primer extension product is subjected to electrophoresis, and the one in which a fraction of an oligonucleotide comprising the nucleotide sequence depicted in SEQ ID NO: 55 is confirmed is determined to be positive.

(4) A method in which, after performing PCR using an oligonucleotide comprising the nucleotide sequence depicted in SEQ ID NO: 9 as a forward primer and an oligonucleotide comprising the nucleotide sequence depicted in SEQ ID NO: 12 as a reverse primer, the obtained primer extension product is subjected to electrophoresis, and the one in which a fraction of an oligonucleotide comprising the nucleotide sequence depicted in SEQ ID NO: 56 is confirmed is determined to be positive.

(5) A method in which, after performing PCR using an oligonucleotide comprising the nucleotide sequence depicted in SEQ ID NO: 13 as a forward primer and an oligonucleotide comprising the nucleotide sequence depicted in SEQ ID NO: 14 as a reverse primer, the obtained primer extension product is subjected to electrophoresis, and the one in which a fraction of 216 base pair or a fraction of an oligonucleotide comprising the nucleotide sequence depicted in SEQ ID NO: 57 is confirmed is determined to be positive.

(6) A method in which, after performing PCR using an oligonucleotide comprising the nucleotide sequence depicted in SEQ ID NO: 15 as a forward primer and an oligonucleotide comprising the nucleotide sequence depicted in SEQ ID NO: 16 as a reverse primer, the obtained primer extension product is subjected to electrophoresis, and the one in which a fraction of 168 base pair or a fraction of an oligonucleotide comprising the nucleotide sequence depicted in SEQ ID NO: 58 is confirmed is determined to be positive.

(7) A method in which, after performing PCR using an oligonucleotide comprising the nucleotide sequence depicted in SEQ ID NO: 13 as a forward primer and an oligonucleotide comprising the nucleotide sequence depicted in SEQ ID NO: 16 as a reverse primer, the obtained primer extension product is subjected to electrophoresis, and the one in which a fraction of 336 base pair or a fraction of an oligonucleotide comprising the nucleotide sequence depicted in SEQ ID NO: 59 is confirmed is determined to be positive.

(8) A method in which, after performing PCR using an oligonucleotide comprising the nucleotide sequence depicted in SEQ ID NO: 17 as a forward primer and an oligonucleotide comprising the nucleotide sequence depicted in SEQ ID NO: 22 as a reverse primer, the obtained primer extension product is subjected to electrophoresis, and the one in which a fraction of an oligonucleotide comprising the nucleotide sequence depicted in SEQ ID NO: 60 is confirmed is determined to be positive.

(9) A method in which, after performing PCR using an oligonucleotide comprising the nucleotide sequence depicted in SEQ ID NO: 18 as a forward primer and an oligonucleotide comprising the nucleotide sequence depicted in SEQ ID NO: 23 as a reverse primer, the obtained primer extension product is subjected to electrophoresis, and the one in which a fraction of an oligonucleotide comprising the nucleotide sequence depicted in SEQ ID NO: 61 is confirmed is determined to be positive.

(10) A method in which, after performing PCR using an oligonucleotide comprising the nucleotide sequence depicted in SEQ ID NO: 19 as a forward primer and an oligonucleotide comprising the nucleotide sequence depicted in SEQ ID NO: 24 as a reverse primer, the obtained primer extension product is subjected to electrophoresis, and the one in which a fraction of an oligonucleotide comprising the nucleotide sequence depicted in SEQ ID NO: 62 is confirmed is determined to be positive.

(11) A method in which, after performing PCR using an oligonucleotide comprising the nucleotide sequence depicted in SEQ ID NO: 20 as a forward primer and an oligonucleotide comprising the nucleotide sequence depicted in SEQ ID NO: 25 as a reverse primer, the obtained primer extension product is subjected to electrophoresis, and the one in which a fraction of an oligonucleotide comprising the nucleotide sequence depicted in SEQ ID NO: 63 is confirmed is determined to be positive.

(12) A method in which, after performing PCR using an oligonucleotide comprising the nucleotide sequence depicted in SEQ ID NO: 21 as a forward primer and an oligonucleotide comprising the nucleotide sequence depicted in SEQ ID NO: 26 as a reverse primer, the obtained primer extension product is subjected to electrophoresis, and the one in which a fraction of an oligonucleotide comprising the nucleotide sequence depicted in SEQ ID NO: 64 is confirmed is determined to be positive.

(13) A method in which, after performing PCR using an oligonucleotide comprising the nucleotide sequence depicted in SEQ ID NO: 27 as a forward primer and an oligonucleotide comprising the nucleotide sequence depicted in SEQ ID NO: 28 as a reverse primer, the obtained primer extension product is subjected to electrophoresis, and the one in which a fraction of 156 base pair or a fraction of an oligonucleotide comprising the nucleotide sequence depicted in SEQ ID NO: 65 is confirmed is determined to be positive.

(14) A method in which, after performing PCR using an oligonucleotide comprising the nucleotide sequence depicted in SEQ ID NO: 29 as a forward primer and an oligonucleotide comprising the nucleotide sequence depicted in SEQ ID NO: 30 as a reverse primer, the obtained primer extension product is subjected to electrophoresis, and the one in which a fraction of 156 base pair or a fraction of an oligonucleotide comprising the nucleotide sequence depicted in SEQ ID NO: 66 is confirmed is determined to be positive.

(15) A method in which, after performing PCR using an oligonucleotide comprising the nucleotide sequence depicted in SEQ ID NO: 27 as a forward primer and an oligonucleotide comprising the nucleotide sequence depicted in SEQ ID NO: 30 as a reverse primer, the obtained primer extension product is subjected to electrophoresis, and the one in which a fraction of 358 base pair or a fraction of an oligonucleotide comprising the nucleotide sequence depicted in SEQ ID NO: 67 is confirmed is determined to be positive.

(16) A method in which, after performing PCR using an oligonucleotide comprising the nucleotide sequence depicted in SEQ ID NO: 31 as a forward primer and an oligonucleotide comprising the nucleotide sequence depicted in SEQ ID NO: 36 as a reverse primer, the obtained primer extension product is subjected to electrophoresis, and the one in which a fraction of an oligonucleotide comprising the nucleotide sequence depicted in SEQ ID NO: 68 is confirmed is determined to be positive.

(17) A method in which, after performing PCR using an oligonucleotide comprising the nucleotide sequence depicted in SEQ ID NO: 32 as a forward primer and an oligonucleotide comprising the nucleotide sequence depicted in SEQ ID NO: 37 as a reverse primer, the obtained primer extension product is subjected to electrophoresis, and the one in which a fraction of an oligonucleotide comprising the nucleotide sequence depicted in SEQ ID NO: 69 is confirmed is determined to be positive.

(18) A method in which, after performing PCR using an oligonucleotide comprising the nucleotide sequence depicted in SEQ ID NO: 33 as a forward primer and an oligonucleotide comprising the nucleotide sequence depicted in SEQ ID NO: 38 as a reverse primer, the obtained primer extension product is subjected to electrophoresis, and the one in which a fraction of an oligonucleotide comprising the nucleotide sequence depicted in SEQ ID NO: 70 is confirmed is determined to be positive.

(19) A method in which, after performing PCR using an oligonucleotide comprising the nucleotide sequence depicted in SEQ ID NO: 34 as a forward primer and an oligonucleotide comprising the nucleotide sequence depicted in SEQ ID NO: 39 as a reverse primer, the obtained primer extension product is subjected to electrophoresis, and the one in which a fraction of an oligonucleotide comprising the nucleotide sequence depicted in SEQ ID NO: 71 is confirmed is determined to be positive.

(20) A method in which, after performing PCR using an oligonucleotide comprising the nucleotide sequence depicted in SEQ ID NO: 35 as a forward primer and an oligonucleotide comprising the nucleotide sequence depicted in SEQ ID NO: 40 as a reverse primer, the obtained primer extension product is subjected to electrophoresis, and the one in which a fraction of an oligonucleotide comprising the nucleotide sequence depicted in SEQ ID NO: 72 is confirmed is determined to be positive.

(21) A method in which, after performing PCR using an oligonucleotide comprising the nucleotide sequence depicted in SEQ ID NO: 41 as a forward primer and an oligonucleotide comprising the nucleotide sequence depicted in SEQ ID NO: 42 as a reverse primer, the obtained primer extension product is subjected to electrophoresis, and the one in which a fraction of 163 base pair or a fraction of an oligonucleotide comprising the nucleotide sequence depicted in SEQ ID NO: 73 is confirmed is determined to be positive.

(22) A method in which, after performing PCR using an oligonucleotide comprising the nucleotide sequence depicted in SEQ ID NO: 43 as a forward primer and an oligonucleotide comprising the nucleotide sequence depicted in SEQ ID NO: 44 as a reverse primer, the obtained primer extension product is subjected to electrophoresis, and the one in which a fraction of 158 base pair or a fraction of an oligonucleotide comprising the nucleotide sequence depicted in SEQ ID NO: 74 is confirmed is determined to be positive.

(23) A method in which, after performing PCR using an oligonucleotide comprising the nucleotide sequence depicted in SEQ ID NO: 41 as a forward primer and an oligonucleotide comprising the nucleotide sequence depicted in SEQ ID NO: 44 as a reverse primer, the obtained primer extension product is subjected to electrophoresis, and the one in which a fraction of 387 base pair or a fraction of an oligonucleotide comprising the nucleotide sequence depicted in SEQ ID NO: 75 is confirmed is determined to be positive.

(24) A method in which, after performing PCR using an oligonucleotide comprising the nucleotide sequence depicted in SEQ ID NO: 45 as a forward primer and an oligonucleotide comprising the nucleotide sequence depicted in SEQ ID NO: 49 as a reverse primer, the obtained primer extension product is subjected to electrophoresis, and the one in which a fraction of an oligonucleotide comprising the nucleotide sequence depicted in SEQ ID NO: 76 is confirmed is determined to be positive.

(25) A method in which, after performing PCR using an oligonucleotide comprising the nucleotide sequence depicted in SEQ ID NO: 46 as a forward primer and an oligonucleotide comprising the nucleotide sequence depicted in SEQ ID NO: 50 as a reverse primer, the obtained primer extension product is subjected to electrophoresis, and the one in which a fraction of an oligonucleotide comprising the nucleotide sequence depicted in SEQ ID NO: 77 is confirmed is determined to be positive.

(26) A method in which, after performing PCR using an oligonucleotide comprising the nucleotide sequence depicted in SEQ ID NO: 47 as a forward primer and an oligonucleotide comprising the nucleotide sequence depicted in SEQ ID NO: 51 as a reverse primer, the obtained primer extension product is subjected to electrophoresis, and the one in which a fraction of an oligonucleotide comprising the nucleotide sequence depicted in SEQ ID NO: 78 is confirmed is determined to be positive.

(27) A method in which, after performing PCR using an oligonucleotide comprising the nucleotide sequence depicted in SEQ ID NO: 48 as a forward primer and an oligonucleotide comprising the nucleotide sequence depicted in SEQ ID NO: 52 as a reverse primer, the obtained primer extension product is subjected to electrophoresis, and the one in which a fraction of an oligonucleotide comprising the nucleotide sequence depicted in SEQ ID NO: 79 is confirmed is determined to be positive.

Among those described above, the methods of (1), (5) to (7), (13) to (15), (21) to (23) are preferable.

(A-1-2) A Method in which the Determination is Made by Hybridization Using a Labeled Probe A method in which the determination is made by hybridization using a labeled probe includes, for example, a method in which, after electrophoresis, the obtained electrophoretic fraction is subjected to hybridization with a labeled probe prepared by labeling a probe of the present invention with a labeling substance, and the one which has been confirmed the presence of a fraction hybridized with the aforementioned labeled probe by detecting the signal derived form the aforementioned labeled probe is determined to be positive.

Specific examples of the probe to be used and the labeling substance of the probe and a labeling method of the probe are as described above.

A specific determination method according to the method of (A-1-2) includes, for example, the following methods:

(1) A method in which, after performing the PCR using an oligonucleotide comprising the nucleotide sequence depicted in SEQ ID NO: 5 as a forward primer and an oligonucleotide comprising the nucleotide sequence depicted in SEQ ID NO: 6 as a reverse primer, the obtained primer extension product is subjected to electrophoresis, and then an electrophoretic fraction obtained is tested for hybridization with a labeled probe prepared by labeling an oligonucleotide which comprises a part or the entire sequence of the nucleotide sequence depicted in SEQ ID NO: 53 with a labeling substance, and the one which is confirmed the presence of a fraction hybridized with aforementioned labeled probe by detecting the signal derived from the aforementioned labeled probe is determined to be positive.

(2) A method in which, after performing PCR using an oligonucleotide comprising the nucleotide sequence depicted in SEQ ID NO: 7 as a forward primer and an oligonucleotide comprising the nucleotide sequence depicted in SEQ ID NO: 10 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 54 with a labeling substance is examined, and the one which is confirmed the presence of a fraction hybridized with aforementioned labeled probe by detecting the signal derived from the aforementioned labeled probe is determined to be positive.

(3) A method in which, after performing PCR using an oligonucleotide comprising the nucleotide sequence depicted in SEQ ID NO: 8 as a forward primer and an oligonucleotide comprising the nucleotide sequence depicted in SEQ ID NO: 11 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 55 with a labeling substance is examined, and the one which is confirmed the presence of a fraction hybridized with aforementioned labeled probe by detecting the signal derived from the aforementioned labeled probe is determined to be positive.

(4) A method in which, after performing PCR using an oligonucleotide comprising the nucleotide sequence depicted in SEQ ID NO: 9 as a forward primer and an oligonucleotide comprising the nucleotide sequence depicted in SEQ ID NO: 12 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 56 with a labeling substance is examined, and the one which is confirmed the presence of a fraction hybridized with aforementioned labeled probe by detecting the signal derived from the aforementioned labeled probe is determined to be positive.

(5) A method in which, after performing PCR using an oligonucleotide comprising the nucleotide sequence depicted in SEQ ID NO: 13 as a forward primer and an oligonucleotide comprising the nucleotide sequence depicted in SEQ ID NO: 14 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 57 with a labeling substance is examined, and the one which is confirmed the presence of a fraction hybridized with aforementioned labeled probe by detecting the signal derived from the aforementioned labeled probe is determined to be positive.

(6) A method in which, after performing PCR using an oligonucleotide comprising the nucleotide sequence depicted in SEQ ID NO: 15 as a forward primer and an oligonucleotide comprising the nucleotide sequence depicted in SEQ ID NO: 16 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 58 with a labeling substance is examined, and the one which is confirmed the presence of a fraction hybridized with aforementioned labeled probe by detecting the signal derived from the aforementioned labeled probe is determined to be positive.

(7) A method in which, after performing PCR using an oligonucleotide comprising the nucleotide sequence depicted in SEQ ID NO: 13 as a forward primer and an oligonucleotide comprising the nucleotide sequence depicted in SEQ ID NO: 16 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 59 with a labeling substance is examined, and the one which is confirmed the presence of a fraction hybridized with aforementioned labeled probe by detecting the signal derived from the aforementioned labeled probe is determined to be positive.

(8) A method in which, after performing PCR using an oligonucleotide comprising the nucleotide sequence depicted in SEQ ID NO: 17 as a forward primer and an oligonucleotide comprising the nucleotide sequence depicted in SEQ ID NO: 22 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 60 with a labeling substance is examined, and the one which is confirmed the presence of a fraction hybridized with aforementioned labeled probe by detecting the signal derived from the aforementioned labeled probe is determined to be positive.

(9) A method in which, after performing PCR using an oligonucleotide comprising the nucleotide sequence depicted in SEQ ID NO: 18 as a forward primer and an oligonucleotide comprising the nucleotide sequence depicted in SEQ ID NO: 23 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 61 with a labeling substance is examined, and the one which is confirmed the presence of a fraction hybridized with aforementioned labeled probe by detecting the signal derived from the aforementioned labeled probe is determined to be positive.

(10) A method in which, after performing PCR using an oligonucleotide comprising the nucleotide sequence depicted in SEQ ID NO: 19 as a forward primer and an oligonucleotide comprising the nucleotide sequence depicted in SEQ ID NO: 24 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 62 with a labeling substance is examined, and the one which is confirmed the presence of a fraction hybridized with aforementioned labeled probe by detecting the signal derived from the aforementioned labeled probe is determined to be positive.

(11) A method in which, after performing PCR using an oligonucleotide comprising the nucleotide sequence depicted in SEQ ID NO: 20 as a forward primer and an oligonucleotide comprising the nucleotide sequence depicted in SEQ ID NO: 25 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 63 with a labeling substance is examined, and the one which is confirmed the presence of a fraction hybridized with aforementioned labeled probe by detecting the signal derived from the aforementioned labeled probe is determined to be positive.

(12) A method in which, after performing PCR using an oligonucleotide comprising the nucleotide sequence depicted in SEQ ID NO: 21 as a forward primer and an oligonucleotide comprising the nucleotide sequence depicted in SEQ ID NO: 26 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 64 with a labeling substance is examined, and the one which is confirmed the presence of a fraction hybridized with aforementioned labeled probe by detecting the signal derived from the aforementioned labeled probe is determined to be positive.

(13) A method in which, after performing PCR using an oligonucleotide comprising the nucleotide sequence depicted in SEQ ID NO: 27 as a forward primer and an oligonucleotide comprising the nucleotide sequence depicted in SEQ ID NO: 28 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 65 with a labeling substance is examined, and the one which is confirmed the presence of a fraction hybridized with aforementioned labeled probe by detecting the signal derived from the aforementioned labeled probe is determined to be positive.

(14) A method in which, after performing PCR using an oligonucleotide comprising the nucleotide sequence depicted in SEQ ID NO: 29 as a forward primer and an oligonucleotide comprising the nucleotide sequence depicted in SEQ ID NO: 30 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 66 with a labeling substance is examined, and the one which is confirmed the presence of a fraction hybridized with aforementioned labeled probe by detecting the signal derived from the aforementioned labeled probe is determined to be positive.

(15) A method in which, after performing PCR using an oligonucleotide comprising the nucleotide sequence depicted in SEQ ID NO: 27 as a forward primer and an oligonucleotide comprising the nucleotide sequence depicted in SEQ ID NO: 30 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 67 with a labeling substance is examined, and the one which is confirmed the presence of a fraction hybridized with aforementioned labeled probe by detecting the signal derived from the aforementioned labeled probe is determined to be positive.

(16) A method in which, after performing PCR using an oligonucleotide comprising the nucleotide sequence depicted in SEQ ID NO: 31 as a forward primer and an oligonucleotide comprising the nucleotide sequence depicted in SEQ ID NO: 36 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 68 with a labeling substance is examined, and the one which is confirmed the presence of a fraction hybridized with aforementioned labeled probe by detecting the signal derived from the aforementioned labeled probe is determined to be positive.

(17) A method in which, after performing PCR using an oligonucleotide comprising the nucleotide sequence depicted in SEQ ID NO: 32 as a forward primer and an oligonucleotide comprising the nucleotide sequence depicted in SEQ ID NO: 37 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 69 with a labeling substance is examined, and the one which is confirmed the presence of a fraction hybridized with aforementioned labeled probe by detecting the signal derived from the aforementioned labeled probe is determined to be positive.

(18) A method in which, after performing PCR using an oligonucleotide comprising the nucleotide sequence depicted in SEQ ID NO: 33 as a forward primer and an oligonucleotide comprising the nucleotide sequence depicted in SEQ ID NO: 38 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 70 with a labeling substance is examined, and the one which is confirmed the presence of a fraction hybridized with aforementioned labeled probe by detecting the signal derived from the aforementioned labeled probe is determined to be positive.

(19) A method in which, after performing PCR using an oligonucleotide comprising the nucleotide sequence depicted in SEQ ID NO: 34 as a forward primer and an oligonucleotide comprising the nucleotide sequence depicted in SEQ ID NO: 39 as a reverse primer, the obtained primer extension product is subjected to electrophoresis; and then hybridization with a labeled probe prepared by labeling an oligonucleotide which comprises a part or the entire sequence of the nucleotide sequence depicted in SEQ ID NO: 71 with a labeling substance is examined, and the one which is confirmed the presence of a fraction hybridized with aforementioned labeled probe by detecting the signal derived from the aforementioned labeled probe is determined to be positive.

(20) A method in which, after performing PCR using an oligonucleotide comprising the nucleotide sequence depicted in SEQ ID NO: 35 as a forward primer and an oligonucleotide comprising the nucleotide sequence depicted in SEQ ID NO: 40 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 72 with a labeling substance is examined, and the one which is confirmed the presence of a fraction hybridized with aforementioned labeled probe by detecting the signal derived from the aforementioned labeled probe is determined to be positive.

(21) A method in which, after performing PCR using an oligonucleotide comprising the nucleotide sequence depicted in SEQ ID NO: 41 as a forward primer and an oligonucleotide comprising the nucleotide sequence depicted in SEQ ID NO: 42 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 73 with a labeling substance is examined, and the one which is confirmed the presence of a fraction hybridized with aforementioned labeled probe by detecting the signal derived from the aforementioned labeled probe is determined to be positive.

(22) A method in which, after performing PCR using an oligonucleotide comprising the nucleotide sequence depicted in SEQ ID NO: 43 as a forward primer and an oligonucleotide comprising the nucleotide sequence depicted in SEQ ID NO: 44 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 74 with a labeling substance is examined, and the one which is confirmed the presence of a fraction hybridized with aforementioned labeled probe by detecting the signal derived from the aforementioned labeled probe is determined to be positive.

(23) A method in which, after performing PCR using an oligonucleotide comprising the nucleotide sequence depicted in SEQ ID NO: 41 as a forward primer and an oligonucleotide comprising the nucleotide sequence depicted in SEQ ID NO: 44 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 75 with a labeling substance is examined, and the one which is confirmed the presence of a fraction hybridized with aforementioned labeled probe by detecting the signal derived from the aforementioned labeled probe is determined to be positive.

(24) A method in which, after performing PCR using an oligonucleotide comprising the nucleotide sequence depicted in SEQ ID NO: 45 as a forward primer and an oligonucleotide comprising the nucleotide sequence depicted in SEQ ID NO: 49 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 76 with a labeling substance is examined, and the one which is confirmed the presence of a fraction hybridized with aforementioned labeled probe by detecting the signal derived from the aforementioned labeled probe is determined to be positive.

(25) A method in which, after performing PCR using an oligonucleotide comprising the nucleotide sequence depicted in SEQ ID NO: 46 as a forward primer and an oligonucleotide comprising the nucleotide sequence depicted in SEQ ID NO: 50 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 77 with a labeling substance is examined, and the one which is confirmed the presence of a fraction hybridized with aforementioned labeled probe by detecting the signal derived from the aforementioned labeled probe is determined to be positive.

(26) A method in which, after performing PCR using an oligonucleotide comprising the nucleotide sequence depicted in SEQ ID NO: 47 as a forward primer and an oligonucleotide comprising the nucleotide sequence depicted in SEQ ID NO: 51 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 78 with a labeling substance is examined, and the one which is confirmed the presence of a fraction hybridized with aforementioned labeled probe by detecting the signal derived from the aforementioned labeled probe is determined to be positive.

(27) A method in which, after performing PCR using an oligonucleotide comprising the nucleotide sequence depicted in SEQ ID NO: 48 as a forward primer and an oligonucleotide comprising the nucleotide sequence depicted in SEQ ID NO: 52 as a reverse primer, the obtained primer extension product is subjected to electrophoresis, and then hybridization with a labeled probe prepared by labeling an oligonucleotide which comprises a part or the entire sequence of the nucleotide sequence depicted in SEQ ID NO: 79 with a labeling substance is examined, and the one which is confirmed the presence of a fraction hybridized with aforementioned labeled probe by detecting the signal derived from the aforementioned labeled probe is determined to be positive.

Among those described above, the methods of (1), (5) to (7), (13) to (15), (21) to (23) are preferable.

Taking, for example, a case that *M. kansasii* is detected by the method (the method of above (1) of (A-1-1)) in which, after performing PCR using an oligonucleotide comprising the nucleotide sequence depicted in SEQ ID NO: 5 as a forward primer and an oligonucleotide comprising the nucleotide sequence depicted in SEQ ID NO: 6 as a reverse primer and followed by electrophoresis, the primer extension product having objective number of base pair is confirmed as an example, the detailed method for detecting *M. kansasii* involved in the present invention is as follows:

Firstly, according to the above described method, the purified DNA sample is prepared from a specimen to be tested for the presence of *M. kansasii*. Separately, by the method described above, an oligonucleotide comprising the nucleotide sequence depicted in SEQ ID NO: 5 (hereinafter, represented as 1c_plate1_Fw1) and an oligonucleotide comprising the nucleotide sequence depicted in SEQ ID NO: 6 (hereinafter, represented as 1c_plate1_Rv1) are synthesized from the nucleotide of in the present invention by phosphoamidite method using a DNA synthesizer.

A 10 mM Tris-HCl buffer (pH 8.9) containing 1c_plate1_Fw1 and 1c_plate1_Rv1, 1.0 to 4.0 mM $MgCl_2$, 80 mM KCl, 500 μg/ml BSA, 0.1% sodium cholate, 0.005 to 0.2% polyoxyethylene octylphenyl ether, each 0.1 to 0.6 mM of dATP, dCTP, dGTP and dTTP, and 10 to 80 unit/ml of Taq DNA polymerase is prepared and used as a reaction solution for PCR.

The purified DNA is added to the reaction solution for PCR, and using this solution as a sample for PCR, 20 to 40 cycles of the PCR is carried out by the DNA Thermal Cycler. The reaction solution after PCR is subjected to a 1.5% agarose gel electrophoresis. In the next place, after staining the gel with ethidium bromide, the fluorescent signal generated by UV ray is detected. Also, the molecular weight marker is electrophoresed in the same time in parallel with the reaction solution, and the length of the detected DNA fragment is calculated by comparing the relative mobility. In the PCR using the 1c_plate1_Fw1 as a forward primer and the 1c_plate1_Rv1 as a reverse primer, it is anticipated that the DNA fragment with 167 base pair (SEQ ID NO: 53) in the nucleotide sequence of *M. kansasii* will be replicated. Consequently, the one which is confirmed the presence of fluorescent band of 167 base pair can be determined to be positive.

(A-2) A Method by Real-Time PCR

In the method for detecting *M. kansasii* of the present invention, the real-time amplification system (see, for example, U.S. Pat. Nos. 5,210,015 and 5,538,848) can also be utilized.

An example of the detection system by the real-time amplification system includes, for example, the real-time PCR detection system.

Various real-time PCR detection methods, for example, TaqMan™ real-time PCR method (see, for example, U.S. Pat. No. 5,538,848), MGB Eclipse Probe System method (see, for example, U.S. Pat. No. 5,801,155), Molecular Beacons Probe Technology method (see, for example, U.S. Pat. No. 5,925,517), LUX Fluorogenic Primer method (Invitrogen Corporation), Quenching probe-PCR (QP) method (see, for example, U.S. Pat. No. 6,492,121) and the like can be utilized for the method for detecting *M. kansasii* of the present invention.

More specifically, by the real-time PCR method using a probe in which the 5'-terminal is labeled, for example, with a fluorescent dye (reporter) such as FAM and the 3'-terminal is labeled, for example, with a quencher dye such as TAMRA (see, for example, U.S. Pat. No. 5,538,848), a minute quantity of target DNA can be detected with high sensitivity and quantitatively.

That is, using an oligonucleotide which comprises a part or the entire sequence of the nucleotide sequence depicted in SEQ ID NO: 1, SEQ ID NO: 2, SEQ ID NO: 3 or SEQ ID NO: 4, or a part or the entire sequence of a nucleotide sequence complementary to the nucleotide sequence, wherein the oligonucleotide is capable of hybridizing with the nucleotide sequence of *M. kansasii* gene as a primer (the primer of the present invention), and using a labeled oligonucleotide which is labeled with a reporter fluorescent dye on the 5'-terminal and with quencher dye on the 3'-terminal as a labeled probe, and which comprises a part or the entire sequence of the nucleotide sequence depicted in SEQ ID NO: 1, SEQ ID NO: 2, SEQ ID NO: 3 or SEQ ID NO: 4, or a part or the entire sequence of a nucleotide sequence complementary to the nucleotide sequence, wherein the oligonucleotide is capable of hybridizing with the nucleotide sequence of *M. kansasii* gene (the oligonucleotide of the present invention), the PCR is carried out for the nucleic acid in a sample as a template, and then the fluorescent signal released from aforementioned labeled probe is detected.

The principle of the above described real-time PCR is as follows.

That is, an oligonucleotide which is labeled with a fluorescent dye (reporter) on the 5'-terminal and with a quencher dye on the 3'-terminal, and is capable of hybridizing with a particular region of the objective gene is utilized. The reporter fluorescence of the aforementioned probe is suppressed by the quencher dye in the ordinary condition. Under the state that the fluorescent probe is hybridized completely with the objective gene, the PCR is performed from outside of the hybrid using DNA polymerase. In accordance with the progress of the extension reaction by DNA polymerase, the 5'-terminal of the fluorescent probe is hydrolyzed by its exonuclease activity to release the fluorescent dye and generate fluorescence. In the real-time PCR method, by monitoring this fluorescent signal in real time, the initial quantity of template DNA can be quantified correctly.

The probe to be used for the labeled probe which is labeled with a fluorescent dye (reporter) on the 5'-terminal and with a quencher dye on the 3'-terminal and is used for the real-time PCR detection system of the present invention can be the above described probe of the present invention. Practically, a probe having a nucleotide sequence of amplification product obtained from the real-time PCR by the combination of forward primer and reverse primer, or a probe having a nucleotide sequence designed further from the above sequence can be used. For example, the probe to be used when the real-time PCR is carried out using the primers of SEQ ID NO: 5 and SEQ ID NO: 6 includes a nucleotide having an expected amplified nucleotide sequence of SEQ ID NO: 53 by the real-time PCR, or an oligonucleotide having a sequence designed from the nucleotide sequence of SEQ ID NO: 53 (for example, SEQ ID NO: 80).

In addition, the reporter fluorescent substance to be used for labeling the 5'-terminal includes FAM, HEX, TET, Cy5, VIC and the like, however, among them, FAM is preferable. The quencher dye to be used for labeling the 3'-terminal includes a fluorescent substance such as TAMRA and a non-fluorescent substance such as BHQ (e.g., BHQ2) and DABCYL, however, among them, TAMRA is preferable.

The forward primer and the reverse primer to be used for the real-time PCR detection system involved in the present invention include the ones used in the above-described PCR, and the specific examples of preferable primer and preferable combination are also as described above.

The other deoxyribonucleoside triphosphate (dATP, DCTP, dGTP, dTTP), the reagent such as DNA polymerase and the like to be used for the real-time PCR detection system can be the same as used in the usual real-time PCR, and the procedure of the real-time PCR, except for using the primer and the probe of the present invention, can be carried out according to the common protocol of the real-time PCR.

An example of the method for detecting *M. kansasii* by the real-time PCR detection system of the present invention is explained as follows.

Firstly, according to the method described above, a purified DNA sample is obtained from a specimen to be tested for *M. kansasii*. Separately, the oligonucleotides having the nucleotide sequence depicted in SEQ ID NO: 5 (1c_plate1_Fw1) and SEQ ID NO: 6 (1c_plate1_Rv1) are synthesized by the phosphoamidite method using a DNA synthesizer.

In addition, from the nucleotide sequence depicted in SEQ ID No: 53 to be amplified by the PCR using 1c_plate1_Fw1 and 1c_plate1_Rv1 as primers, a sequence to be used as a probe (e.g., SEQ ID No: 80) is designed, and an oligonucleotide of this sequence is synthesized. The 5'-terminal of this oligonucleotide is labeled with a reporter dye of FAM, and 3'-terminal is labeled with a reporter quencher of TAMRA by the conventional procedures, and thus a fluorescence labeled probe is obtained.

Using the above prepared 1c_plate1_Fw1 as a forward primer and the 1c_plate1_Rv1 as a reverse primer, the real-time PCR is carried out, for example, as follows.

That is, a 10 mM Tris-HCl buffer (pH 8.9) containing each 1 μM of primer 1c_plate1_Fw1 and primer 1c_plate1_Rv1, 100 to 1000 nM fluorescence-labeled probe, 1.0 to 4.0 mM $MgCl_2$, 80 mM KCl, 500 μg/ml BSA, 0.1% sodium cholate, 0.005 to 0.2% TritonX-100, each 0.2 mM of dATP, dCTP, dGTP and dTTP, and 10 to 80 unit/ml of Taq DNA polymerase is prepared and used as a reaction solution. To 20 μl of the reaction solution 1 ng of purified DNA sample is added and used as a sample for PCR. This sample for PCR is placed in each well of a 96-well reaction plate, and the real-time PCR is carried out using appropriate real-time PCR detection equipment and the like. The reaction is repeated 30 to 50 cycles, and at every cycle, the fluorescent intensity of the reporter dye is measured.

In the determination of *M. kansasii*, when the fluorescent signal of the reporter dye is observed, the sample can be determined to be *M. kansasii* positive.

In addition, in the real-time PCR method, as a standard curve can be made up, the number of genomic DNA (copy number) of *M. kansasii* in the sample can be determined. In addition, as this number is proportional to the number of *M. kansasii* cell, the number of *M. kansasii* cell in the sample can also be determined. The preparation of the standard curve can be carried out according to the conventional procedure commonly performed in the real-time PCR method. For example, using *M. kansasii* genomic DNA sample of known copy number as a standard, a dilution series of concentration (copy number) of the DNA sample for PCR is prepared. In the next place, using each of the dilution series of the DNA sample for PCR, the real-time PCR is carried out according to the above described method, and the fluorescent intensity of the reporter dye is measured. For each of the dilution series of the DNA sample for PCR, the measured value of the fluorescent intensity (Rn, y-axis) is plotted for each cycle number of PCR (x-axis) to make up an amplification curve. After that, an Rn part where the fluorescent intensity amplifies exponentially is selected, and a threshold line (Th) is drawn. The crossing point of the Th with an amplification curve of each DNA sample for PCR is defined as threshold cycle (Ct). After that, the Ct value (y-axis) is plotted for the logarithmic value of the copy number of each used DNA sample for PCR (x-axis), and an approximated curve obtained for each Ct can be used as a standard curve.

For the quantitative determination of the number of the genomic DNA (copy number) of *M. kansasii* in the sample, at first, the DNA is isolated and purified from the specimen to be tested for *M. kansasii*, and the real-time PCR of the obtained DNA sample is carried out, and an amplification curve is made up by the same manner. The Ct value at the point of crossing the Th drawn at the time of preparing the standard curve by the obtained amplification curve is obtained. By fitting the Ct value to the standard curve, the quantity (copy number) of genomic DNA of *M. kansasii* in the sample can be obtained.

In addition, the present invention can be applied in the nucleic acid amplification step with a detection method using RNA transcription product. For example, NASBA (nucleic acid sequence based amplification) method (JP Patent No. 2650159), 3SR (self-sustained sequence replication) method (JP-B-7-114718), TAS (transcription based amplification system) method (JP-A-2-500565: International publication no. WO 88/10315), TMA (transcription mediated amplification) method (JP-A-11-46778) and the like are included. Among them, the constant temperature nucleic acid amplification methods utilizing a concerted mode of action of reverse transcriptase and RNA polymerase (a reaction condition which allows the reverse transcriptase and the RNA polymerase act as concertedly) is suitable for the automation of the determination system.

(A-3) A Method in which the Determination is Performed by Measuring the Signal Derived from the Primer Extension Product Obtained by the Polymerase Chain Reaction Using a Labeled Primer In this method, such a method is included in which, using a labeled primer prepared by labeling the primer of the present invention according to the above described method, the PCR is carried out for the nucleic acid in the sample as a template, and then the signal derived from the obtained primer extension product is measured, and when the signal derived form the primer is detected in the obtained primer extension product, the sample is determined to be *M. kansasii* positive. The forward primer and the reverse primer to be used in this method include the ones used in the above described PCR method, and the specific examples of preferable primer and preferable combination are also as described above.

In the case of the above-described method, after PCR is carried out; free labeled primer is removed; the signal derived from the primer extension product is measured; and when the signal is detected, the sample can be determined to be *M. kansasii* positive.

In the method of removing free labeled primer, such a method is included in which after the primer extension product in the reaction mixture obtained by the PCR is precipitated by the conventional procedure of nucleic acid precipitation (ethanol precipitation method, a precipitation method using isopropanol and the like), the supernatant solution containing nonprecipitating free labeled primer is removed and the like.

In addition, a method of separating the primer extension product from free labeled primer in the reaction mixture obtained by PCR by treating with gel chromatography under suitable conditions or by electrophoresis under suitable conditions is also included.

(B) A Method Using the Labeled Oligonucleotide of the Present Invention as a Labeled Probe Further, in the method for detecting *M. kansasii* of the present invention, an oligonucleotide which comprises a part or the entire sequence of the nucleotide sequence depicted in SEQ ID NO: 1, SEQ ID NO: 2, SEQ ID NO: 3 or SEQ ID NO: 4, or a part or the entire sequence of a nucleotide sequence complementary to the nucleotide sequence, wherein the oligonucleotide is capable of hybridizing with the nucleotide sequence of *M. kansasii* gene (the oligonucleotide of the present invention) is labeled with a labeling substance, and using this labeled oligonucleotide as a labeled probe, the aforementioned labeled probe is allowed to hybridize with the nucleic acid in the sample, and after removal of the free labeled probe, the signal derived from the hybridized complex is detected.

Specifically, the method includes, for example:

(B-1) a detection method in which using the oligonucleotide of the present invention immobilized on the solid carrier as a trapping probe, hybridization with nucleic acid in the sample is carried out to immobilize the nucleic acid derived from *M. kansasii* on the solid phase (see, for example, JP-A-62-265999);

(B-2) a method of so called "sandwich assay" in which using the trapping probe of (B-1) and the labeled probe prepared by labeling the probe of the present invention, hybridization with nucleic acid in the sample is carried out to form a complex of the trapping probe and the nucleic acid from *M. kansasii* and the labeled probe, then the signal derived from the labeled probe is determined (see, for example, JP-A-58-40099); and (B-3) a method in which using the biotin-labeled probe of the present invention, hybridization with nucleic acid in the sample is carried out, and then the nucleic acid derived from *M. kansasii* in the sample is trapped by avidin immobilized carrier, and the like.

It should be noted that as the reagent used for the method for detecting *M. kansasii* of the present invention, the reagent usually used in this field, for example, buffering agent, stabilizer, preservatives and the like which neither inhibit the stability of the coexisting reagent and the like nor inhibit PCR and hybridization reaction can be used. In addition, the concentration of the reagent can be selected as appropriate from the range of concentration usually used in this field.

Specific example of buffer solution includes all the buffer solutions usually used for performing PCR and hybridization reaction in this field, for example, Tris buffer, phosphate buffer, veronal buffer, borate buffer, good buffer and the like; and the pH of the buffer solution is not particularly limited, but generally a range between pH 5 to pH 9 is preferable.

In addition, if need arises, the nucleic acid synthetase (DNA polymerase, RNA polymerase, reverse transcriptase and the like), the substrate corresponding to the enzyme (dNTP, rNTP and the like), and additionally, the double strand intercalator (ethidium bromide, SYBR™ Green and the like), and alternatively, the signal detection substance such as FAM and TAMRA can be used.

A kit for detecting *M. kansasii* involved in the present invention includes "a kit for detecting *M. kansasii* comprising an oligonucleotide comprising a part or the entire sequence of the nucleotide sequence depicted in SEQ ID NO: 1, SEQ ID NO: 2, SEQ ID NO: 3 or SEQ ID NO: 4, or a part or the entire sequence of a nucleotide sequence complementary to the nucleotide sequence, wherein the oligonucleotide is capable of hybridizing with the nucleotide sequence of *M. kansasii* gene as a primer (the primer of the present invention) and/or a probe (the probe of the present invention)". The primer can be the one which is labeled with a labeling substance. The specific example of the labeling substance is as described above.

The kit comprising the primer of the present invention also comprises a composition containing a pair of forward primer and reverse primer. Preferable embodiments are as follows:

(1) A kit comprising a forward primer of an oligonucleotide which comprises a part or the entire sequence of the nucleotide sequence depicted in SEQ ID NO: 5, or a part or the entire sequence of a nucleotide sequence complementary to the nucleotide sequence, wherein the oligonucleotide is, capable of hybridizing with the nucleotide sequence of *M. kansasii* gene; and a reverse primer of an oligonucleotide which comprises a part or the entire sequence of the nucleotide sequence depicted in SEQ ID NO: 6 or a part or the entire sequence of a nucleotide sequence complementary to the nucleotide sequence and is capable of hybridizing with the nucleotide sequence of *M. kansasii* gene as the constituent reagent.

(2) A kit comprising a forward primer of an oligonucleotide which comprises a part or the entire sequence of the nucleotide sequence depicted in SEQ ID NO: 13, or a part or the entire sequence of a nucleotide sequence complementary to the nucleotide sequence, wherein the oligonucleotide is capable of hybridizing with the nucleotide sequence of *M. kansasii* gene; and a reverse primer of an oligonucleotide which comprises a part or the entire sequence of the nucleotide sequence depicted in SEQ ID NO: 14, or a part or the entire sequence of a nucleotide sequence complementary to the nucleotide sequence and is capable of hybridizing with the nucleotide sequence of *M. kansasii* gene as the constituent reagent.

(3) A kit comprising a forward primer of an oligonucleotide which comprises a part or the entire sequence of the nucleotide sequence depicted in SEQ ID NO: 15, or a part or the entire sequence of a nucleotide sequence complementary to the nucleotide sequence, wherein the oligonucleotide is capable of hybridizing with the nucleotide sequence of *M. kansasii* gene; and a reverse primer of an oligonucleotide which comprises a part or the entire sequence of the nucleotide sequence depicted in SEQ ID NO: 16, or a part or the entire sequence of a nucleotide sequence complementary to the nucleotide sequence and is capable of hybridizing with the nucleotide sequence of *M. kansasii* gene as the constituent reagent.

(4) A kit comprising a forward primer of an oligonucleotide which comprises a part or the entire sequence of the nucleotide sequence depicted in SEQ ID NO: 13, or a part or the entire sequence of a nucleotide sequence complementary to the nucleotide sequence, wherein the oligonucleotide is capable of hybridizing with the nucleotide sequence of *M. kansasii* gene; and a reverse primer of an oligonucleotide which comprises a part or the entire sequence of the nucleotide sequence depicted in SEQ ID NO: 16, or a part or the entire sequence of a nucleotide sequence complementary to the nucleotide sequence and is capable of hybridizing with the nucleotide sequence of *M. kansasii* gene as the constituent reagent.

(5) A kit comprising a forward primer of an oligonucleotide which comprises a part or the entire sequence of the nucleotide sequence depicted in SEQ ID NO: 27, or a part or the entire sequence of a nucleotide sequence complementary to the nucleotide sequence, wherein the oligonucleotide is capable of hybridizing with the nucleotide sequence of M kansasii gene; and a reverse primer of an oligonucleotide which comprises a part or the entire sequence of the nucleotide sequence depicted in SEQ ID NO: 28, or a part or the entire sequence of a nucleotide sequence complementary to the nucleotide sequence and is capable of hybridizing with the nucleotide sequence of *M. kansasii* gene as the constituent reagent.

(6) A kit comprising a forward primer of an oligonucleotide which comprises a part or the entire sequence of the nucleotide sequence depicted in SEQ ID NO: 29, or a part or the entire sequence of a nucleotide sequence complementary to the nucleotide sequence, wherein the oligonucleotide is capable of hybridizing with the nucleotide sequence of *M. kansasii* gene; and a reverse primer of an oligonucleotide which comprises a part or the entire sequence of the nucleotide sequence depicted in SEQ ID NO: 30, or a part or the entire sequence of a nucleotide sequence complementary to the nucleotide sequence and is capable of hybridizing with the nucleotide sequence of *M. kansasii* gene as the constituent reagent.

(7) A kit comprising a forward primer of an oligonucleotide which comprises a part or the entire sequence of the nucleotide sequence depicted in SEQ ID NO: 27, or a part or the entire sequence of a nucleotide sequence complementary to the nucleotide sequence, wherein the oligonucleotide is capable of hybridizing with the nucleotide sequence of *M. kansasii* gene; and a reverse primer of an oligonucleotide which comprises a part or the entire sequence of the nucleotide sequence depicted in SEQ ID NO: 30, or a part or the entire sequence of a nucleotide sequence complementary to the nucleotide sequence and is capable of hybridizing with the nucleotide sequence of *M. kansasii* gene as the constituent reagent.

(8) A kit comprising a forward primer of an oligonucleotide which comprises a part or the entire sequence of the nucleotide sequence depicted in SEQ ID NO: 41, or a part or the entire sequence of a nucleotide sequence complementary to the nucleotide sequence, wherein the oligonucleotide is capable of hybridizing with the nucleotide sequence of *M. kansasii* gene; and a reverse primer of an oligonucleotide which comprises a part or the entire sequence of the nucleotide sequence depicted in SEQ ID NO: 42, or a part or the entire sequence of a nucleotide sequence complementary to the nucleotide sequence and is capable of hybridizing with the nucleotide sequence of *M. kansasii* gene as the constituent reagent.

(9) A kit comprising a forward primer of an oligonucleotide which comprises a part or the entire sequence of the nucleotide sequence depicted in SEQ ID NO: 43, or a part or the entire sequence of a nucleotide sequence complementary to the nucleotide sequence, wherein the oligonucleotide is capable of hybridizing with the nucleotide sequence of *M. kansasii* gene; and a reverse primer of an oligonucleotide which comprises a part or the entire sequence of the nucleotide sequence depicted in SEQ ID NO: 44, or a part or the entire sequence of a nucleotide sequence complementary to the nucleotide sequence and is capable of hybridizing with the nucleotide sequence of *M. kansasii* gene as the constituent reagent.

(10) A kit comprising a forward primer of an oligonucleotide which comprises a part or the entire sequence of the nucleotide sequence depicted in SEQ ID NO: 41, or a part or the entire sequence of a nucleotide sequence complementary to the nucleotide sequence, wherein the oligonucleotide is capable of hybridizing with the nucleotide sequence of *M. kansasii* gene; and a reverse primer of an oligonucleotide which comprises a part or the entire sequence of the nucleotide sequence depicted in SEQ ID NO: 44, or a part or the entire sequence of a nucleotide sequence complementary to the nucleotide sequence and is capable of hybridizing with the nucleotide sequence of *M. kansasii* gene as the constituent reagent.

In the above-described kit, further, the oligonucleotide of the present invention labeled with a labeling substance can be contained as a labeled probe.

Furthermore, "a kit for detecting *M. kansasii* comprising the oligonucleotide of the present invention as a probe" is included. The aforementioned probe can be the one labeled with a labeling substance.

The preferable embodiments and the specific examples of the constituent reagent composing these kits are as described above.

It should be noted that the kit for detecting M, kansasii of the present invention can comprise, for example, buffering agent, stabilizer, preservatives and the like which neither inhibit the stability of the coexisting reagent and the like nor inhibit the PCR and the hybridization reaction. In addition, the concentrations of the reagents can be selected as appropriate from the range of concentration usually used in this field.

The specific example of buffer solution includes all the buffer solutions usually used for performing the PCR and the hybridization reaction in this field, for example, Tris buffer, phosphate buffer, veronal buffer, borate buffer, good buffer and the like, and the pH is not particularly limited, but generally a range between pH 5 to pH 9 is preferable.

In addition, if need arises, the nucleic acid synthetase (DNA polymerase, RNA polymerase, reverse transcriptase and the like), the substrate corresponding to the enzyme (dNTP, rNTP and the like), and additionally, the double strand intercalator (ethidium bromide, SYBR™ Green and the like), and alternatively, the signal detection substance such as FAM and TAMRA can be included.

Hereinafter, the present invention will be further explained in detail by referring to the following Examples, but the scope of the present invention should not be limited thereto.

It should be noted that all bacteria used in Examples are clinical isolates, and their bacterial strain has already been differentiated by the colony morphology and the conventional various biochemical tests on the cultured bacterium.

EXAMPLES

Experimental Example 1

Selection of Clone Derived from *M. kansasii* Genome (1) Preparation of DNA Sample Firstly, colonies of *M. kansasii* (*Mycobacterium kansasii*) cultured on the Ogawa's medium are collected and suspended in purified water and autoclaved (at 120° C. under 2 atmospheres for 20 minutes), and by way of disruption treatment (physical disruption using 2 mm diameter of glass beads) followed by centrifugation, the supernatant solution was obtained. From the supernatant solution obtained, extraction and purification of DNA was carried out using an ion-exchange resin type DNA extraction and purification kit, Genomic-tip (manufactured by QIAGEN GmbH), and obtained genomic DNA derived from *M. kansasii.*

The purified DNA obtained was adjusted to give final concentration of 400 ng/μl (in 10 mM Tris-HCl buffer, pH 8.9), and used as a DNA sample.

Separately, using a specific sequence of KATS2 for *M. kansasii* as described in JP-A-11-155589 and a specific sequence of *M. tuberculosis* (*Mycobacterium tuberculosis*: human type tuberculosis bacterium) designated as SEQ ID NO: 8 in the description of JP-A-2004-129272 (in the present description, shown as SEQ ID NO: 81) as positive control, and using purified DNA derived from *E. coli* prepared according to the conventional procedure of extraction and purification of *E. coli* DNA as a negative control, DNA samples were prepared in the same manner as described above, and used similarly for the following treatment.

(2) Preparation of Whole Genome Shotgun Library

Using a 24 μg of the DNA sample obtained in (1) above as a material, the Whole Genome Shotgun library was made up by the following method (a modified Whole Genome Shotgun method, modified from the method described in Venter et al., Science 2001 Feb. 16; 291 (5507): 1304-1351).

The DNA sample was treated using a nebulizer (manufactured by Invitrogen) in the presence of 20% final concentration of glycerol under the pressure of 5 kPa to 9 kPa for about 10 minutes to fractionate the DNA, and the fraction with objective size of 500 to 1,000 bp was recovered efficiently. The fraction obtained was purified using an extraction column (manufactured by QIAGEN GmbH).

In the next place, using the DNA Blunting Kit manufactured by Takara Bio Inc. and through the use of 5'→3' polymerase activity and 3'→5' exonuclease activity of T4 DNA Polymerase, the terminal of obtained DNA was blunted. This blunt-ended DNA was subjected to ligation reaction with the blunt-ended pBSII sk+vector (Stratagene), and a recombinant DNA of the pBSII sk+vector ($amp^r$) incorporated with the DNA fragment was prepared.

Transformation of *E. coli* JM109 Competent Cells (Takara Bio Inc.) was carried out using the recombinant DNA obtained above according to a protocol of the product. The transformant obtained above was cultured in a plate on LB-agarose medium containing 100 μg/ml ampicillin, 0.2 mM IPTG and 40 μg/ml X-Gal, and white colonies were picked up, and thus a library of transformant (Whole Genome Shotgun clone of *M. kansasii* genome) which has been introduced with the recombinant DNA incorporated with the objective DNA fragment was obtained.

(3) Preparation of Microarray

Using the Whole Genome Shotgun clone of *M. kansasii* genome obtained in (2) above, the PCR was carried out by the following method, and the probe material for fixing on a slide glass was prepared.

A 10 mM Tris-HCl buffer solution (pH 8.9) containing 1 μM each of M13 Primer M1 (Takara Bio Inc.) and M13 Primer RV (Takara Bio Inc.), 1.5 mM $MgCl_2$, 80 mM KCl, 500 μg/ml BSA, 0.1% sodium cholate, 0.1% Triton X-100 (product name of polyoxyethylene octylphenyl ether, Rohm and Haas Co.), 0.2 mM each of dATP, dCTP, dGTP and dTTP, and 40 unit/ml of Taq DNA polymerase (Nippon Gene Co.) was prepared and used as a reaction solution for PCR.

The DNA was purified from the Whole Genome Shotgun clone of *M. kansasii* genome obtained in (1) above according to the conventional procedure, and added to suspend in 20 μl of the reaction solution for PCR; and using this suspension as a sample for PCR (act as a template), 30 cycles of PCR was carried out under the following conditions using the DNA Thermal Cycler (DNA Engine PTC200; MJ Research Inc.).

The reaction conditions of the PCR:

Heat denaturation: 94° C. for 0.5 minutes;

Annealing: 55° C. for 1 minute;

Polymerization reaction: 75° C. for 0.5 minutes.

The obtained PCR product was purified, and then mixed with an immobilization buffer (final concentration: 3×SSC).

Using a typing instrument (GTMAS Stamp II; Nippon Laser & Electronics); the final concentration of the PCR product to be spotted was adjusted to give 300 ng/μl; the humidity in the instrument was set to 55%; the PCR product obtained was spotted (the spot diameter: 150 to 250 μm) on a slide glass (CMT GAPS-II; Corning Inc.). The spot-completed slide glass was transferred to a UV cross linker (UV Stratalinker 1800; Stratagene Co.), and was irradiated with 150 mJ/cm$^2$ of UV light to fix the PCR product (the objective DNA) on the slide glass, and thus the microarray was prepared.

(4) Fluorescent Labeling of the Target Genomic DNA and Microarray Hybridization i) Fluorescent Labeling of the Target Genomic DNA Firstly, using BioPrime DNA labeling system (Invitrogen Co.), 2 μg of each genomic DNA derived from *M. kansasii* (ATCC 12478) and a comparative genomic DNA (bovine type tuberculosis bacterium, ATCC 19274) were each mixed with 20 μl of random primer solution contained in the product, and heat denaturation treatment was carried out (95° C. for 5 minutes).

After that, to each heat treated mixture, 2 μl of 0.1 M DTT, 2 μl of the mixed solution of dATP/dCTP/dGTP (each 5 mM), 0.8 μl of 2.5 mM dTTP, 1.6 μl of 5 mM Ha-dUTP and 1 μl of Klenow enzyme (40 U/μl) were added and adjusted to give the final volume 50 μl with sterile deionized water, and then the extension reaction was carried out at 37° C. for 3 hours. An ultrafiltration column Microcon YM-30 (Millipore Co.) was set to the attached 1.5 ml tube, and then the above-described reaction product was placed on the column and centrifuged at 14,000 rpm for 4 minutes. The concentrated solution was recovered in a microtube and dried thoroughly using a centrifugal vacuum drier (CentriVap concentrator; Labconco Co.).

The dried reaction product obtained was added with 10 μl of 50 mM $NaHCO_3$ and mixed, then left at room temperature for 2 to 3 minutes.

Separately, 1 mg of each Cy3 (Amersham Biosciences) and Cy5 (Amersham Biosciences) was dissolved separately in 105 μt of DMSO. A 10 μL of the Cy-dye Solution Cy3 was added to the above reaction product obtained using comparative genome (bovine type tuberculosis bacterium) and 10 μl of the Cy-dye Solution Cy5 was added to the above reaction product obtained using *M. kansasii* genome, and each reaction mixture was incubated (under light shielding) at 40° C. for 60 minutes.

Further, each above reaction product was added with 10 μl of 4 M $NH_2OH$ (prepared just before use) and mixed, and is incubated (under light shielding) for 15 minutes to obtain the respective labeled product, namely, Cy3 labeled comparative genomic DNA (bovine type tuberculosis bacterium) and Cy5 labeled *M. kansasii* genomic DNA were obtained.

An ultrafiltration column Microcon YM-30 (Millipore Co.) was set to the attached 1.5 ml tube, and then the above obtained labeled product of genomic DNA was placed on the column and centrifuged at 14,000 rpm for 4 minutes. The concentrated solution was recovered in a microtube and dried thoroughly using a centrifugal vacuum drier (CentriVap concentrator; Labconco Co.).

ii) Fragmentation Process of Labeled Product

To the labeled product of genomic DNA in dry state obtained in i) of (4) above, a 40 μl of a solution with a composition of final concentrations of 0.04 M Tris-acetate (pH 8.1), 0.1 M potassium acetate, and 0.03 M magnesium acetate tetrahydrate was added and mixed in suspension. The suspension is heat-treated at 94° C. for 15 minutes, and the fragmentation product of each labeled genomic DNA with 100 to 300 bases was obtained.

The labeling efficiency (base/dye) was checked using BcaBEST DNA Polymerase (Takara Bio Inc.) and rBst DNA Polymerase (EPICENTRE Biotechnologies), and confirmed that one molecule of dye was incorporated into about 20 bases of the comparative (bovine type tuberculosis bacterium) genomic DNA, and one molecule of dye was incorporated into about 10 bases of the *M. kansasii* genomic DNA.

Each solution of Cy3-labeled product and Cy5-labeled product was placed separately onto an ultrafiltration column Microcon YM-30 (Millipore Co.) and centrifuged at 14,000 rpm for 4 minutes, and each concentrated solution is recovered in a microtube, and then dried thoroughly using a centrifugal vacuum drier (CentriVap concentrator; Labconco Co.). In the next place, to a microtube, the following reagents (in the case when the slide glass for the microarray to be used later is 24×55 mm) were added, and the above obtained Cy3-labeled product and Cy5-labeled product were mixed in suspension in the same solution.

ArrayHyb Hybridization buffer (SIGMA); 40 μl
salmon sperm DNA (10 mg/ml); 0.5 μl
formamide; 5 μl
Total 40 to 50 μl After mixing in suspension, the mixture was incubated at 95° C. for 5 minutes, and kept at 70° C. until use for hybridization.

iii) Microarray Hybridization

On a microarray (DNA chip) prepared in the above-described (3), the whole solution of mixture of Cy3-labeled product and Cy5-labeled product obtained in the above-described ii) of (4) was placed, and covered with a cover glass keeping no air bubble remained inside. The microarray was set on a Hybri-cassette; placed in a Tupperware matted with a Kim Towel (Nippon Paper Crecia Co., Ltd.) wetted with distilled water and closed tightly; and reacted (under light shielding) at 65° C. for 8 hours or more to allow hybridization. After hybridization, the microarray was soaked in a 2×SSC-0.1% SDS solution together with cover glass at room temperature, and shook gently in the solution to remove the cover glass. After sequential washing with 1×SSC and 0.03% SDS solution (60° C.) for 10 minutes, 0.2×SSC solution (42° C.) for 10 minutes and 0.05×SSC solution (room temperature) for 10 minutes, the microarray was transferred quickly to a new dry rack, and dried immediately by centrifugation at 800 rpm for 5 minutes.

(5) Measurement of Fluorescent Intensity: from Signal Detection to Quantification Using a fluorescence readout scanner (Protein Array Scanner; Nippon Laser & Electronics), the fluorescent intensity on the microarray obtained in above iii) of (4) was measured, and obtained fluorescence detection data on 2 channel fluorescent intensity of Cy3 and Cy5. The quantification of fluorescent signal was performed using the DNASIS™-Array (DNA chip expression image analysis software; Hitachi Software Engineering Co.), and according to the operation procedure of the software, automatic spot recognition, background calculation, and normalization of fluorescent intensity ratio were carried out. In addition, by establishing a threshold limit line of reliability, and avoiding the value lower than this line, the reliable normalized fluorescent intensity ratio was obtained.

It should be noted that the positive control (the specific DNA fragment for *M. tuberculosis* and the fragment of KATS2 sequence of *M. kansasii*) and the negative control (the DNA fragment derived from *E. coli*) had been spotted on the microarray.

In addition, for the purpose of screening a candidate sequence of use in detecting *M. kansasii* specifically, based on the Cy3/Cy5 fluorescent intensity ratio (Ratio) detected on the DNA chip, the scatter plot analysis was carried out. The results are shown in FIG. 5.

By way of comparison, the KATS2 sequence of *M. kansasii* described in JP-A-1999-155589 and the sequence depicted in SEQ ID NO: 8 (SEQ ID NO: 81 in this specification) derived from *M. tuberculosis* described in the description of JP-A-2004-129272 were treated in the same way, and the fluorescent intensity of Cy3 and Cy5 were determined. The results are shown collectively in FIG. 5.

In FIG. 5, the entire scatter plot and the enlarged view of a part where spots are concentrated (encircled by dotted line) are shown. The scatter plot is shown on a double logarithmic chart, as a plot of the fluorescent intensity of Cy5 on the vertical axis for the fluorescent intensity of Cy3 on the horizontal axis. In FIG. 5, the spots other than (2) and (3) show the results when the PCR product on each microarray was used; the spot encircled as (2) shows the results when the KAS sequence of *M. kansasii* described in JP-A-11-155589 was used; and the spot encircled as (3) shows the results when the nucleotide sequence depicted in SEQ ID NO: 8 (SEQ ID NO: 81 in this specification) derived from *M. tuberculosis* described in the description of JP Application No. 2004-129272 was used.

In addition, each line on FIG. 5 has the following meaning.

(a): The line indicating:

Cy5/Cy3 ratio of fluorescent intensity ≧10.

(b): The line indicating:

Cy5/Cy3 ratio of fluorescent intensity ≧5.0;

(c): The line indicating:

Cy5/Cy3 ratio of fluorescent intensity ≧2.0;

(a'): The line indicating:

Cy3/Cy5 ratio of fluorescent intensity ≧10.0;

(b'): The line indicating:

Cy3/Cy5 ratio of fluorescent intensity ≧5.0;

(c'): The line indicating:

Cy3/Cy5 ratio of fluorescent intensity ≧2.0.

That is, the spot locating at upper position than the line (a) indicates that the fluorescent intensity of Cy5 is 10 times or more greater compared with that of Cy3; the spot locating at upper position than the line (b) indicates that the fluorescent intensity of Cy5 is 5 to 10 times greater compared with that of Cy3; and the spot locating at upper position than the line (c) indicates that the fluorescent intensity of Cy5 is 2 to 5 times greater compared with that of Cy3. In addition, the spot locating at lower position than the line (a') indicates that the fluorescent intensity of Cy3 is 10 times or more great compared with that of Cy5; the spot locating at lower position than the line (b') indicates that the fluorescent intensity of Cy3 is 5 to 10 times greater compared with that of Cy5; and the spot locating at lower position than the line (c') indicates that the fluorescent intensity of Cy3 is 2 to 5 times greater compared with that of Cy5.

As is clear from FIG. 5, the spot (3) locating in between the line (b') and the line (a') indicates that the fluorescent intensity of Cy3 is 5 to 10 times greater compared with that of Cy5, and this spot can be recognized as being hybridized with the genomic DNA of bovine type M. *tuberculosis*. On the other hand, the spot (2) locating in between the line (c) and the line (b) indicates that the fluorescent intensity of Cy5 is 2 to 5 times greater compared with that of Cy3, and this spot can be recognized as being hybridized with the genomic DNA of *M. kansasii*.

It should be noted that in the case when the genomic DNA of *E. coli* is used as a control, the fluorescent intensity ratio of Cy5/Cy3 was around 1, and the spot on the scatter plot was locating at a very low position, and therefore the spot is not shown in FIG. 5.

Here, in FIG. 5, among the screen-detected PCR product of microarray, the 8 spots encircled as (1) (it seems that only 5 spots exist, but actually 8 spots exist because some spots are overlapped) were detected greater fluorescent intensity of Cy5 than (2), and from the fact described above the specificity of (1) for *M. kansasii* was judged as higher than that of (2) (the KATS2 sequence of *M. kansasii* described in JP-A-11-155589). Thus, these 8 clones were selected as the candidate clone.

(6) Determination of Nucleotide Sequence of the Candidate Clone

The nucleotide sequence of the 8 candidate clones selected in the above (5) was carried out by the method described below.

That is, using the Big Dye Terminator kit (Applied Biosystems), the sequence analysis was carried out by the following procedures according to the protocol of the product.

The candidate DNA (the candidate clone); 2 μl (100 ng)

M13 Primer M1; 1 μl (5 pmol)

Premix; 8 μl

To the above mixture, sterile deionized water was added to make the total volume 20 μl, and then 30 cycles of the sequencing reaction under the following reaction conditions were carried out using the DNA Thermal Cycler (DNA Engine PTC200, MJ Research Inc.):

96° C. for 2 min.→(96° C. for 10 sec.→50° C. for 5 sec.→60° C. for 4 min.)x25→4° C.

The sequencing reaction product obtained was purified using a gel filtration column (QIAGEN GmbH), and then using a sequencer (BaseStation, MJ Research Inc.) the sequence mapping of all the candidate sequence was carried out according to the operation manual provided for the sequencer.

The data obtained were searched from the data base (NCBI Blast) and found that all of the 8 candidate clones were unregistered new sequences on the data base. This can supposedly be attributed to the fact that *M. kansasii* is an organism species with undeciphered genome sequence.

Example 1

Evaluation of the Specificity of the Candidate Clone for *M. kansasii*

The 8 candidate clones obtained in Experimental Example 1 were evaluated by performing agarose gel electrophoresis detection experiment in combination with the PCR amplification system for their availability for the *M. kansasii* specific detection system using nucleic acid amplification detection system.

(1) The Synthesis of the Primer for PCR

Firstly, based on the result of sequence analysis of the candidate clone 1, the primer sequence for the PCR amplification detection was designed using a web tool for primer design, Primer 3 (Whitehead Institute for Biomedical Research). Using the designed "CGGCCATTGTTCTACAGTCT" (SEQ ID NO: 5; hereinafter referred to as 1c_plate1_Fw1) and "TAGAGATCCATCGCTTTGGT" (SEQ ID NO: 6; hereinafter referred to as 1c_plate1_Rv1), the PCR was carried out as described below. The designed oligonucleotide was synthesized by the phosphoamidite method using the ABI 392 DNA synthesizer (Applied Biosystems Inc.). The synthetic procedures were performed in accordance with the manual provided by ABI, and the deprotection of various types of oligonucleotide was performed by heating the ammonia solution of oligonucleotide at 55° C. for overnight. In the next place, the synthesized oligonucleotide was purified by the anion-exchange column chromatography using the Pharmacia FPLC.

It should be noted that the nucleotide sequence obtained from the result of sequence analysis of the candidate clone 1 is the sequence depicted in SEQ ID NO: 1.

(2) Preparation of Sample

Using the following bacteria, the extraction and purification of DNA were carried out by the method described below, and DNA samples were obtained. All bacteria used were clinical isolates, and their bacterial strain had already been differentiated by the colony morphology and the conventional various biochemical tests on the cultured bacterium.

a: *Escherichia coli;*
b: *Mycobacterium tuberculosis;*
c: *Mycobacterium kansasii;*
d: *Mycobacterium marinum;*
e: *Mycobacterium simiae;*
f: *Mycobacterium scrofulaceum;*
g: *Mycobacterium gordonae;*
h: *Mycobacterium szulgai;*
i: *Mycobacterium avium;*
j: *Mycobacterium intracellulare;*
k: *Mycobacterium gastri;*
l: *Mycobacterium xenopi;*
m: *Mycobacterium nonchromogenicum;*
n: *Mycobacterium terrae;*
o: *Mycobacterium triviale;*
p: *Mycobacterium fortuitum;*
q: *Mycobacterium chelonei;*
r: *Mycobacterium abscessus;*
s: *Mycobacterium peregrinum.*

Firstly, as to the genus *Mycobacterium* bacteria, colonies grown on the Ogawa's medium were collected and suspended in purified water and autoclaved (at 120° C. under 2 atmospheres for 20 minutes), and by way of disruption treatment (physical disruption using 2 mm diameter of glass beads) followed by centrifugation, the supernatant solution was obtained. From the supernatant solution obtained, the extraction and purification of DNA were carried out using an ion-exchange resin type DNA extraction and purification kit Genomic-tip (QIAGEN GmbH). As to *E. coli*, according to the conventional procedure of *E. coli* DNA extraction method, extraction and purification of DNA were carried out.

The purified DNA obtained was adjusted to give final concentration of 1 ng/μl (10 mM Tris-HCl buffer, pH 8.9), and used as a DNA sample.

(3) PCR

The PCR was carried out as follows using the primer sequences of 1c_plate1_Fw1 and 1c_plate1_Rv1 which were designed and synthesized by the above described method based on the nucleotide sequence (SEQ ID NO: 1) of the candidate clone. It should be noted that, the locating position of each primer on the nucleotide sequence of the candidate clone 1 was as shown in FIG. 1.

A 10 mM Tris-HCl buffer solution (pH 8.9) containing 1 μM each of the primer 1c_plate1_Fw1 and the primer 1c_plate1_Rv1, 1.5 mM $MgCl_2$, 80 mM KCl, 500 μg/ml BSA, 0.1% sodium cholate, 0.1% Triton X-100 (product name of polyoxyethylene octylphenyl ether; Rohm and Haas Co.), 0.2 mM each of dATP, dCTP, dGTP and dTTP, and 40 unit/ml of Taq DNA polymerase (Nippon Gene Co.) was prepared and used as a reaction solution for PCR.

A 20 μl of the reaction solution for PCR was added with 1 ng of the DNA sample, and using this solution as a sample for PCR, 30 cycles of PCR were carried out under the following condition using the DNA Thermal Cycler (DNA Engine PTC200; MJ Research Inc.).

The reaction conditions of the PCR:
Heat denaturation: 94° C. for 0.5 minutes;
Annealing: 55° C. for 1 minute;
Polymerization reaction: 75° C. for 0.5 minutes.

(4) Electrophoresis

A 5 μl of the reaction solution obtained after the PCR in (3) above was electrophoresed on a 1.5% agarose gel. Conditions of the electrophoresis were constant voltage of 100 V for 30 minutes. The operating procedure and other conditions were in accordance with the general method described in Bio Experiment Illustrated, vol. 2, p 53-63, by Hiroki Nakayama (Shujunsha Co., Ltd.). In the next place, after staining the gel with ethidium bromide, the UV-light induced fluorescent signal was detected using a UV sample photographic device FAS-III System (Toyobo Co., Ltd.). Also, the molecular weight marker was electrophoresed simultaneously in parallel with the reaction solution, and thereby, the length of the detected DNA fragment was calculated by comparing the relative mobility. In this regard, the X174/HaeIII digest (Marker 4; Nippon Gene Co., Ltd.) was used as the molecular weight marker.

The obtained results of electrophoresis are shown in FIG. 6.

In FIG. 6, letters given on each lane indicates the results when the following samples were used:

M4: molecular weight marker (Marker 4);
a: *Escherichia coli;*
b: *Mycobacterium tuberculosis;*
c: *Mycobacterium kansasii;*
d: *Mycobacterium marinum;*
e: *Mycobacterium simiae;*
f: *Mycobacterium scrofulaceum;*
g: *Mycobacterium gordonae;*
h: *Mycobacterium szulgai;*
i: *Mycobacterium avium;*
j: *Mycobacterium intracellulare;*
k: *Mycobacterium gastri;*
l: *Mycobacterium xenopi;*
m: *Mycobacterium nonchromogenicum;*
n: *Mycobacterium terrae;*
o: *Mycobacterium triviale;*
p: *Mycobacterium fortuitum;*
q: *Mycobacterium chelonei;*
r: *Mycobacterium abscessus;*
s: *Mycobacterium* peregrinum.

By the PCR using forward primer 1c_plate1_Fw1 and reverse primer 1c_plate1_Rv1, DNA fragment with 167 base pair (SEQ ID NO: 53) in the candidate sequence 1 which is locating in the *M. kansasii* genome was expected to be replicated. Therefore, the one of which the fluorescent band of 167 base pair was confirmed was determined to be positive.

As is clear from the results shown in FIG. 6, in the PCR performed using the primer 1c_plate1_Fw1 and the primer 1c_plate1_Rv1 of the present invention, only when *M. kansasii* was used as a sample (c), the fluorescent band of 167 base pair was confirmed, and the sample could be determined to be positive. Contrary to this, when the other *Mycobacterium* bacteria and the bacterium belonging to other genus such as *E. coli* were used as a sample (a, b, d-s), the corresponding fluorescent band was not confirmed, and all the sample could be determined to be negative.

From the results obtained above, it can be proved that the candidate clone 1 is an oligonucleotide which comprises the nucleotide sequence specific to *M. kansasii* and by performing the PCR using the primer designed based on this sequence, *M. kansasii* can be detected specifically. In addition, as the detection by nucleic acid amplification such as PCR can be expected to be highly sensitive, isolation of bacterium is not necessary and the clinical specimen can be used directly for the detection. In consequence, the detection of *M. kansasii*, which used to take several weeks by the conventional method in which the bacterial cultivation is necessary before detection is carried out, can be finished within a day at the longest.

Example 2

Detection of *M. kansasii* using the primer of the present invention 1

As to the candidate clone 2 obtained in (6) of Experimental Example 1, based on the nucleotide sequence thereof, 6c_plate1_Fw1 (SEQ ID NO: 13) as a forward primer and 6c_plate1_Rv1(SEQ ID NO: 14) as a reverse primer were designed and synthesized by the same method as described in (1) of Example 1. Using the same samples and reagents, and by the same method as described in (2) to (4) of Example 1, the PCR and the electrophoresis were carried out.

In addition, the nucleotide sequence of the candidate clone 2 obtained from the result of sequence analysis was the one depicted in SEQ ID NO: 2, and the location of each designed primer on the nucleotide sequence of the candidate clone 2 was as shown in FIG. 2.

By the PCR using forward primer 6c_plate1_Fw1 and reverse primer 6c_plate1_Rv1, DNA fragment with 216 base pair (SEQ ID NO: 57) in the candidate sequence 2 which is locating in the *M. kansasii* genome was expected to be replicated. Therefore, the one of which the fluorescent band of 216 base pair was confirmed was determined to be positive.

In consequence, only when *M. kansasii* was used as a sample (c), the fluorescent band of 216 base pair was confirmed, and the sample could be determined to be positive. Contrary to this, when the other *Mycobacterium* bacteria and the bacterium belonging to other genus such as *E. coli* were used as a sample (a, b, d-s), the corresponding fluorescent band was not confirmed, and all the sample could be determined to be negative.

From the results obtained above, it can be proved that the candidate clone 2 is also an oligonucleotide which comprises the nucleotide sequence specific to *M. kansasii* and by performing the PCR using the primer designed according to this sequence, *M. kansasii* can be detected specifically.

Example 3

Detection of *M. kansasii* Using the Primer of the Present Invention 2

As to the candidate clone 3 to 8 obtained in (6) of Experimental Example 1, based on the nucleotide sequence thereof, the primer was designed and synthesized by the same method as described in (1) of Example 1. Using the same samples and reagents, and by the same method as described in (2) to (4) of Example 1 except for using the synthesized primers, the PCR and the electrophoresis were carried out.

In consequence, taking the specificity for *M. kansasii* into consideration, the candidate sequences 3 and 4 have high specificity for *M. kansasii*, and were found to have efficacy for the determination.

In addition, the nucleotide sequence of the candidate clone 3 obtained from the result of sequence analysis was the one depicted in SEQ ID NO: 3, and the location of each designed primer on the nucleotide sequence of the candidate clone 3 was as shown in FIG. 3.

Also, the nucleotide sequence of the candidate clone 4 obtained from the result of sequence analysis was the one depicted in SEQ ID NO: 4, and the location of each designed primer on the nucleotide sequence of the candidate clone 4 was as shown in FIG. 4.

Example 4

Detection of *M. kansasii* by the Real-Time PCR System (1) Synthesis of the PCR Primer for the Detection of *M. kansasii*

Using the same equipment and by the same procedure as described in (1) of Example 1, the oligonucleotides of 1c_plate1_Fw1 (SEQ ID NO: 5) and 1c_plate1_Rv1 (SEQ ID NO: 6) were synthesized.

(2) Preparation of the Probe for the Detection of *M. kansasii*

From the nucleotide sequence depicted in SEQ ID No: 53 (167 base pair) to be amplified by the PCR using 1c_plate1_Fw1 and 1c_plate1_Rv1 as primers, a sequence to be used as a probe "ACTCAATGCCCTTCGATCCCGGC-GAAC" was designed, and an oligonucleotide comprising this sequence was synthesized (hereinafter, referred to as KAN1c_F1R1_FAMTAM; SEQ ID No: 80). The 5'-terminal of this oligonucleotide was labeled with a reporter dye of FAM and the 3'-terminal was labeled with a reporter quencher of TAMRA, and thus a labeled oligonucleotide probe (TaqMan™ Fluorescent Probe; Applied Biosystems Japan) was obtained.

(3) Preparation of the DNA Sample for PCR

Absorbance of the DNA sample prepared from *M. kansasii* specimen in (1) of Experimental Example 1 was measured to determine the quantity of the DNA in the sample. The quantity of the DNA (copy number of the genome) in the sample was determined by comparing the obtained quantity of DNA with the known quantity of the genomic DNA of *M. kansasii*. A $10^8$ copy/μl of the genomic DNA was obtained.

In the next place, the dilution series of the DNA sample of $10^5$, $10^4$, $10^3$, $10^2$, 10, 5 and 2 copy/μl was prepared using 10 mM Tris-HCl buffer, pH 8.9, and used as a DNA sample for PCR.

(4) Real-Time PCR

Using the 1c_plate1_Fw1 prepared in the above described (1) as the forward primer and the 1c_plate1_Rv1 prepared in the above described (1) as the reverse primer, the real-time PCR was carried out as follows.

That is, a 10 mM Tris-HCl buffer solution (pH 8.9) containing 1 μM each of the primer 1c_plate1_Fw1 and the primer 1c_plate1_Rv1, 195 nM of the fluorescence labeled probe KAN1c_F1R1_FAMTAM prepared in the above (2), 1.5 mM $MgCl_2$, 80 mM KCl, 500 μg/ml BSA, 0.1% sodium cholate, 0.1% Triton X-100 (product name of polyoxyethylene octylphenyl ether; Rohm and Haas Co.), 0.2 mM each of dATP, dCTP, dGTP and dTTP, and 40 unit/ml of Taq DNA polymerase (Nippon Gene Co.) was prepared and used as a reaction solution.

To 20 μl of the reaction solution 1 μl of each dilution series of DNA sample was added and used as a sample for PCR. This sample for PCR was placed in each well of a 96-well reaction plate (MicroAmp Optical 96-well Reaction Plate; Applied Biosystems Japan Ltd.), and the real-time PCR was carried out using a dedicated thermal cycler/detector for the TaqMan™ PCR (ABI 7500, Applied Biosystems Japan Ltd.). The reaction was repeated 50 cycles of a reaction cycle composed of heating at 95° C. for 10 minutes, followed by heating at 95° C. for 15 seconds and 60° C. for 1 minute, and in every cycle, the fluorescent intensity of reporter dye was measured. In addition, the fluorescent intensity was measured and digitalized using the thermal cycler and using the provided function of digitalizing the relative fluorescent intensity ratio of every one of 96-well reaction plate.

(5) Results

From the data obtained, a standard curve was made up according to the conventional procedure commonly performed in the real-time PCR method.

That is, as for each of the DNA sample for PCR, the fluorescent intensity of reporter dye (Rn, y-axis) was plotted for each cycle number of PCR (x-axis) to make up an amplification curve. After that, an Rn part where the fluorescent intensity amplifies exponentially was selected, and a threshold line (Th) was drawn. The crossing point of the Th with the fluorescent intensity of each DNA sample for PCR was defined as threshold cycle (Ct). After that, the Ct value (y-axis) was plotted for the copy number of the genome of each used DNA sample for PCR (x-axis), and an approximated curve obtained for each Ct was used as a standard curve. The standard curve obtained was shown in FIG. 7.

$$y=-3.348x+32.61$$

$$R^2=0.995$$

From the fact that the fluorescent signal was detected by PCR as described above, it is confirmed that *M. kansasii* can be detected by conducting the real-time PCR, using the oligonucleotide of the present invention for the PCR as a primer, and by designing a labeled probe based on the sequence of the region to be amplified.

In addition, it was also confirmed that since the standard curve can be made up, the quantitative determination of *M. kansasii* is possible by the real-time PCR using the primer and the probe of the present invention. Further, it can be understood from FIG. 7 that the real-time PCR method using the primer and the probe of the present invention can detect *M. kansasii* even under the condition that only 2 copies of the genomic DNA of *M. kansasii* is present as the initial quantity.

Furthermore, when the real-time PCR method is utilized, since the fluorescent intensity is monitored in real time, the quantitative determination of initial quantity of the template DNA can be performed more accurately, and the method is considered to be effective for detecting *M. kansasii.*

Industrial Applicability

The method for detecting *Mycobacterium kansasii* using the primer and/or probe of the present invention enables the detection of *M. kansasii* more rapidly and with higher accuracy compared with a conventional bacterium identification method performed by culture examination on a bacterium. Further, the method for detecting *M. kansasii* of the present invention can exclude any false positive result for the diagnosis and can also detect and diagnose *M. kansasii* with higher accuracy compared with a diagnosis method performed by PCR using a conventional primer and/or probe. Still further, the method for detecting *M. kansasii* of the present invention can quantify the *M. kansasii* cell.

What is claimed is:

1. An isolated or purified oligonucleotide designed from a nucleotide sequence consisting of SEQ ID NO: 1, SEQ ID NO: 2, SEQ ID NO: 3, or SEQ ID NO: 4, or from the full complement of the nucleotide sequence consisting of SEQ ID NO: 1, SEQ ID NO: 2, SEQ ID NO: 3, or SEQ ID NO: 4;

wherein the oligonucleotide comprises 15 contiguous bases of the nucleotide sequence consisting of SEQ ID NO: 1, SEQ ID NO: 2, SEQ ID NO: 3, or SEQ ID NO: 4, or 15 contiguous bases of the full complement of the sequence consisting of SEQ ID NO: 1, SEQ ID NO: 2, SEQ ID NO: 3, or SEQ ID NO:4; and wherein the oligonucleotide is capable of hybridizing with nucleotide sequence of *Mycobacterium kansasii* gene.

2. The oligonucleotide according to claim 1, wherein the oligonucleotide designed from the nucleotide sequence consisting of SEQ ID NO: 1, SEQ ID NO: 2, SEQ ID NO: 3, or SEQ ID NO: 4 comprises one of the sequences SEQ ID NOS: 5 to 79, and the oligonucleotide designed from the full complement of the nucleotide sequence consisting of SEQ ID NO: 1, SEQ ID NO: 2, SEQ ID NO: 3, or SEQ ID NO: 4 comprises the full complement of one of the sequences SEQ ID NOS: 5 to 79.

3. The oligonucleotide according to claim 1, wherein the oligonucleotide designed from the nucleotide sequence consisting of SEQ ID NO: 1 comprises one of the sequences SEQ ID NOS: 5 to 12 or SEQ ID NOS: 53 to 56, and the oligonucleotide designed from the full complement of the nucleotide sequence consisting of SEQ ID NO: 1 comprises the full complement of one of the sequences SEQ ID NOS: 5 to 12 or SEQ ID NOS: 53 to 56.

4. The oligonucleotide according to claim 1, wherein the oligonucleotide designed from the nucleotide sequence consisting of SEQ ID NO: 2 comprises one of the sequences SEQ ID NOS: 13 to 26 or SEQ ID NOS: 57 to 64, and the oligonucleotide designed from the full complement of the nucleotide sequence consisting of SEQ ID NO: 2 comprises the full complement of one of the sequences SEQ ID NOS: 13 to 26 or SEQ ID NOS: 57 to 64.

5. The oligonucleotide according to claim 1, wherein the oligonucleotide designed from the nucleotide sequence consisting of SEQ ID NO: 3 comprises one of the sequences SEQ ID NOS: 27 to 40 or SEQ ID NOS: 65 to 72, and the oligonucleotide designed from the full complement of the nucleotide sequence consisting of SEQ ID NO: 3 comprises the full complement of one of the sequences SEQ ID NOS: 27 to 40 or SEQ ID NOS: 65 to 72.

6. The oligonucleotide according to claim 1, wherein the oligonucleotide designed from the nucleotide sequence consisting of SEQ ID NO: 4 comprises one of the sequences SEQ ID NOS: 41 to 52 or SEQ ID NOS: 73 to 79, and the oligonucleotide designed from the full complement of the nucleotide sequence consisting of SEQ ID NO: 4 comprises the full complement of one of the sequences SEQ ID NOS: 41 to 52 or SEQ ID NOS: 73 to 79.

7. A primer for detecting *Mycobacterium kansasii* comprising:

an oligonucleotide designed from a nucleotide sequence consisting of SEQ ID NO: 1, SEQ ID NO: 2, SEQ ID NO: 3, or SEQ ID NO: 4, or from the full complement of the nucleotide sequence consisting of SEQ ID NO: 1, SEQ ID NO: 2, SEQ ID NO: 3, or SEQ ID NO: 4;

wherein the oligonucleotide consists of 18 to 25 bases, wherein the 18 to 25 bases are contiguous bases of the nucleotide sequence consisting of SEQ ID NO: 1, SEQ ID NO: 2, SEQ ID NO: 3, or SEQ ID NO: 4, or contiguous bases of the full complement of the sequence consisting of SEQ ID NO: 1, SEQ ID NO: 2, SEQ ID: 3, or SEQ ID NO: 4;

wherein the oligonucleotide is capable of hybridizing with a nucleotide sequence of *Mycobacterium kansasii* gene; and wherein the oligonucleotide is optionally labeled with a labeling substance.

8. The primer according to claim 7, wherein the oligonucleotide designed from the nucleotide sequence consisting of SEQ ID NO: 1, SEQ ID NO: 2, SEQ ID NO: 3, or SEQ ID NO: 4 comprises one of the sequences SEQ ID NOS: 5 to 52, and the oligonucleotide designed from the full complement of the nucleic acid sequence consisting of SEQ ID NO: 1, SEQ ID NO: 2, SEQ ID NO: 3, or SEQ ID NO: 4 comprises the full complement of one of the sequences SEQ ID NOS: 5 to 52.

9. The primer according to claim 7, wherein the oligonucleotide designed from the nucleotide sequence consisting of SEQ ID NO: 1 comprises one of the sequences SEQ ID NOS: 5 to 12, and the oligonucleotide designed from the full complement of the nucleotide sequence consisting of SEQ ID NO: 1 comprises the full complement of one of the sequences SEQ ID NOS: 5 to 12.

10. The primer according to claim 7, wherein the oligonucleotide designed from the nucleotide sequence consisting of SEQ ID NO: 2 comprises the one of the sequences SEQ ID NOS: 13 to 26, and the oligonucleotide designed from the full complement of the nucleotide sequence consisting of SEQ ID NO: 2 comprises the full complement of one of the sequences SEQ ID NOS: 13 to 26.

11. The primer according to claim 7, wherein the oligonucleotide designed from the nucleotide sequence consisting of SEQ ID NO: 3 comprises one of the sequences SEQ ID NOS: 27 to 40, and the oligonucleotide designed from the full complement of the nucleotide sequence consisting of SEQ ID NO: 3 comprises the full complement of one of the sequences SEQ ID NOS: 27 to 40.

12. The primer according to claim 7, wherein the oligonucleotide designed from the nucleotide sequence consisting of SEQ ID NO: 4 comprises one of the sequences SEQ ID NOS: 41 to 52, and the oligonucleotide designed from the full complement of the nucleotide sequence consisting of SEQ ID NO: 4 comprises the full complement of one of the sequences SEQ ID NOS: 41 to 52.

13. A probe for detecting *Mycobacterium kansasii* comprising:

an oligonucleotide designed from a nucleotide sequence consisting of SEQ ID NO: 1, SEQ ID NO: 2, SEQ ID NO: 3, or SEQ ID NO: 4, or from the full complement of the nucleotide sequence consisting of SEQ ID NO: 1, SEQ ID NO: 2, SEQ ID NO: 3, or SEQ ID NO: 4;

wherein the oligonucleotide consists of the nucleotide sequence SEQ ID NO: 1, SEQ ID NO: 2, SEQ ID NO: 3, or SEQ ID NO: 4, or the full complement of the nucleotide sequence SEQ ID NO: 1, SEQ ID NO: 2, SEQ ID NO: 3, or SEQ ID NO: 4; or 15 to 40 or 100 to 600 contiguous bases of the nucleotide sequence consisting of SEQ ID NO: 1, SEQ ID NO: 2, SEQ ID: 3, or SEQ ID NO: 4, or 15 to 40 or 100 to 600 contiguous bases of the full complement of the sequence consisting of SEQ ID NO: 1, SEQ ID NO: 2, SEQ ID: 3, or SEQ ID NO: 4;

wherein the oligonucleotide is capable of hybridizing with a nucleotide sequence of *Mycobacterium kansasii* gene; and wherein the oligonucleotide is optionally labeled with a labeling substance.

14. The probe according to claim 13, wherein the oligonucleotide designed from the nucleotide sequence consisting of SEQ ID NO: 1, SEQ ID NO: 2, SEQ ID NO: 3, or SEQ ID NO: 4 comprises one of the sequences SEQ ID NOS: 5 to 80, and the oligonucleotide designed from the full complement of the nucleotide sequence consisting of SEQ ID NO: 1, SEQ ID NO: 2, SEQ ID NO: 3, or SEQ ID NO: 4 comprises the full complement of one of the sequences SEQ ID NOS: 5 to 80.

15. The probe according to claim 13, wherein the labeling substance is selected from a radioisotope, an enzyme, a fluorescent substance, a luminescent substance, or biotin.

16. The probe according to claim 13, wherein the probe is labeled with a reporter fluorescent dye and a quencher dye.

17. The probe according to claim 16, wherein the 5'-terminal is labeled with the reporter fluorescent dye and the 3'-terminal is labeled with the quencher dye.

18. A kit for detecting *Mycobacterium kansasii* comprising at least one of a primer, a primer pair, or a probe;

wherein the primer comprises a first oligonucleotide designed from a nucleotide sequence consisting of SEQ ID NO: 1, SEQ ID NO: 2, SEQ ID NO: 3, or SEQ ID NO: 4, or from the full complement of the nucleotide sequence consisting of SEQ ID NO: 1, SEQ ID NO: 2, SEQ ID NO: 3, or SEQ ID NO: 4, wherein the first oligonucleotide consists of 18 to 25 bases, wherein the 18 to 25 bases are contiguous bases of the nucleotide sequence consisting of SEQ ID NO: 1, SEQ ID NO: 2, SEQ ID: 3, or SEQ ID NO: 4, or contiguous bases of the full complement of the sequence consisting of SEQ ID NO: 1, SEQ ID NO: 2, SEQ ID: 3, or SEQ ID NO: 4, and wherein the first oligonucleotide is capable of hybridizing with a nucleotide sequence of *Mycobacterium kansasii* gene, and wherein the first oligonucleotide is optionally labeled with a labeling substance;

wherein the primer pair comprises two of the first oligonucleotides that act as a forward primer and a reverse primer, respectively, in a nucleic acid amplification reaction; and wherein the probe comprises a second oligonucleotide designed from a nucleotide sequence consisting of SEQ ID NO: 1, SEQ ID NO: 2, SEQ ID NO: 3, or SEQ ID NO: 4, or from the full complement of the nucleotide sequence consisting of SEQ ID NO: 1, SEQ ID NO: 2, SEQ ID NO: 3, or SEQ ID NO: 4, wherein the second oligonucleotide consists of the nucleotide sequence SEQ ID NO: 1, SEQ ID NO: 2, SEQ ID NO: 3, or SEQ ID NO: 4, or the full complement of the nucleotide sequence SEQ ID NO: 1, SEQ ID NO: 2, SEQ ID NO: 3, or SEQ ID NO:4; or 15 to 40 bases or 100 to 600 bases, wherein the 15 to 40 bases or 100 to 600 bases are contiguous bases of the nucleotide sequence consisting of SEQ ID NO: 1, SEQ ID NO: 2, SEQ ID: 3, or SEQ ID NO: 4, or contiguous bases of the full complement of the sequence consisting of SEQ ID NO: 1, SEQ ID NO: 2, SEQ ID: 3, or SEQ ID NO: 4, and wherein the second oligonucleotide is capable of hybridizing with a nucleotide sequence of *Mycobacterium kansasii* gene, and wherein the second oligonucleotide is optionally labeled with a labeling substance.

19. The kit according to claim 18, wherein the kit comprises at least one probe and at least one of the primer or the primer pair.

20. The kit according to claim 18, wherein the primer comprising the first oligonucleotide designed from the nucleotide sequence consisting of SEQ ID NO: 1, SEQ ID NO: 2, SEQ ID NO: 3, or SEQ ID NO: 4 comprises one of the sequences SEQ ID NOS: 5 to 52, and the primer comprising the first oligonucleotide designed from the full complement of the nucleotide sequence consisting of SEQ ID NO: 1, SEQ ID NO: 2, SEQ ID NO: 3, or SEQ ID NO: 4 comprises the full complement of one of the sequences SEQ ID NOS: 5 to 52; and wherein the probe comprising the second oligonucleotide designed from the nucleotide sequence consisting of SEQ ID NO: 1, SEQ ID NO: 2, SEQ ID NO: 3, or SEQ ID NO: 4 comprises one of the sequences SEQ ID NOS: 5 to 80, and the probe comprising the second oligonucleotide designed from the full complement of the nucleotide sequence consisting of SEQ ID NO: 1, SEQ ID NO: 2, SEQ ID NO: 3 or SEQ ID NO: 4 comprises the full complement of one of the sequences SEQ ID NOS: 5 to 80.

21. The kit according to claim 18, wherein the labeling substance is selected from a radioisotope, an enzyme, a fluorescent substance, a luminescent substance, or biotin.

22. The kit according to claim 18, wherein the probe is labeled with a reporter fluorescent dye and a quencher dye.

23. The kit according to claim 22, wherein the probe 5'-terminal is labeled with the reporter fluorescent dye and the 3'-terminal is labeled with the quencher dye.

24. The oligonucleotide according to claim 1, wherein the oligonucleotide is obtained from a DNA synthesizer, a microarray method, or an arbitrarily-primed polymerase chain reaction.

25. The oligonucleotide according to claim 1, wherein the oligonucleotide is obtained from a DNA synthesizer using a phosphoramidite method.

* * * * *

SEQUENCE LISTING

```
<160> NUMBER OF SEQ ID NOS: 81

<210> SEQ ID NO 1
<211> LENGTH: 517
<212> TYPE: DNA
<213> ORGANISM: Mycobacterium kansasii

<400> SEQUENCE: 1

ccgcgtcgtg ccccttaccg acaagaccat cggccatctg cacgtctacc tcgacgagtt      60

ccacccgaac atcaccaaac tgcccgcgag acggccattg ttctacagtc tgcatcgcgg     120

gcgacctgcc gaactgtccg ctgacacggt cgccgccgtg ctcaagcagg ccgccgaatc     180

cgcgcgtact caatgccctt cgatcccggc gaacatccac tgtcacctgc tgcggaagac     240

caaagcgatg gatctctacc agcagggcat cccgctaccg atcatcatgc gcctcctcgg     300

ccacgaaaac gcttccacca cagcagcttt ctatgccttt gcaaccctgg acatgatgcg     360

tcaagcgatc aacgccgcca cccccgcgat caacaccgcg gccaccgagc cactcaccga     420

agaccaactc caaaccctct acagtctgcg ataaccgcct gaaacgttaa gccgagaaat     480

ccgccagcac cccccacgag cgcaggacat ctccgca                              517


<210> SEQ ID NO 2
<211> LENGTH: 596
<212> TYPE: DNA
<213> ORGANISM: Mycobacterium kansasii

<400> SEQUENCE: 2

attgatccgt tgtcccgcac tggcgctcgt cggctccggc gagggcggtg agccgatacg      60

tcaattcaac gtattcgccc gacaggccgg cgggccggtg accgctcgga tgttcactac     120

cgacgaaggc gccgacaccc attgccagct cggcaacctg acgtcgtcga atgccgtcac     180

tatggattgg ctcgaagaca ccctcaactc ggattgatcg ttgcgccgct tcaattcacc     240
```

gcgttttgct tgccgcctgg ccggcgcttc gcaccacgct gcggaagaac tccatccgcg 300
cggtgaccag atcgtcggcc aagtccaggg cagcgtcgac aacggtcttg cgtcgtgact 360
cgtcggggag aacggaatcg atctgatcga cgaacttgcg gacggcctcg atggcctttt 420
tgcggccggt ttccaccgat tcgagcacct cgtcggaaag ttcggcccag cgtggctcgg 480
ccttctgcgg cgtctctgtc atgatgtcaa ctccctgaac tctatcgggc ttatactcga 540
ccggcgtacg ccgcaaactt cggcgattgc cgacgctgat gaagttacga ctgtcg 596

<210> SEQ ID NO 3
<211> LENGTH: 636
<212> TYPE: DNA
<213> ORGANISM: Mycobacterium kansasii

<400> SEQUENCE: 3
cagcgttggc ttcccggtcc ttggcgtggg cgaacaagat gtcccagaac ggcgtgaaac 60
cctccaggta cgcattgccg ctctgggtga tcaatgccgt cacccgctcc ggtgtccggc 120
tcgcgatccg cagcccgatg ggtgctccgt agtcctggat gtagagcgca aagcgctgca 180
ggccgagctt gtccacgagg ccttcgacga tctcggtcag attgtcgaag ctatagcgga 240
actcgtcgac cgacggtgcg gccgaattgc cgaagccgat gtaatcggga gccaccaggt 300
agtactcgtc ggagagcgcg gcgatgagat tgcggaacat atgcgagctg gtggggaagc 360
cgtgcagcag gagcaaagcc gggtttcgcg gattgccggc ctcccggaag tacacctcca 420
agccgttgat ggacgtagtc cggtgccggg tgtcgaaggt agtcattgcg gtttcctttc 480
ggtgatggtc gggtgccggt cgggagaacg agcgttctca cggctggttg tagtctagag 540
aacgatcgtt cttagcgcaa ggagggaatg ccatgaccga aggcgaggac cgggataatg 600
tgctcgccgc agccgatagg ttgttcaatg accgcg 636

<210> SEQ ID NO 4
<211> LENGTH: 726
<212> TYPE: DNA
<213> ORGANISM: Mycobacterium kansasii

<400> SEQUENCE: 4
tacggctgct caaccagaat gagcatctgg gtatcgcgcc gacgcgtaac tgtgggttcg 60
accacgcgcg cagtcagatc atcggccgga tcgatgccga ttccgttgtt gacacggatt 120
gggtcgagac gattcgccag tgttttcaag actccgccat cgacgcggtc accggcccgg 180
tccactatta cgacattccg ctgcgtgggc cgatattcag aatcgaccgc atggtccgcc 240
gcaacctgca tcgcacggca accgatcaac ggttcctctt gggcgccaac atggcaatcc 300
ggacctcggc gtggcaggcg gtacgtcatc tcacgcagct ggatctggaa gaccgactcc 360
acgaagacat cgatcttgca ctgacactgt tcaagaataa tttcgagatc gcatacgaat 420
ccacgatggt ggtgggcgcg tctggccgcc gggtggaatg ctcaccgctc gacttttttc 480
gctacgcgac gcgttatacc aggacgacaa aggcgcacgg cgtcaagagt cgttcggcac 540
gtataacgat tgccgttctc atgctgggat atgtgccggt ccgaacactg cggttctttt 600
atgacgccga gaacaatcgg ttcacgcgca agcgctccgg gacgggcggc ggaacgaaat 660
cgaccgacta ctgaggggcg atccgcgagt caatcgaagc accctttgct ttgtagcagg 720
gacaac 726

<210> SEQ ID NO 5
<211> LENGTH: 20

<212> TYPE: DNA
<213> ORGANISM: Artificial Sequence
<220> FEATURE:
<223> OTHER INFORMATION: oligonucleotide primer

<400> SEQUENCE: 5
cggccattgt tctacagtct 20

<210> SEQ ID NO 6
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 6
tagagatcca tcgctttggt 20

<210> SEQ ID NO 7
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 7
gccatctgca cgtctacct 19

<210> SEQ ID NO 8
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 8
aacatccact gtcacctgct 20

<210> SEQ ID NO 9
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 9
ccaccacagc agctttctat 20

<210> SEQ ID NO 10
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 10
atcgaagggc attgagtacg 20

<210> SEQ ID NO 11
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 11
gagttggtct tcggtgagtg 20

<210> SEQ ID NO 12
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 12
gatttctcgg cttaacgttt c 21

<210> SEQ ID NO 13
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 13
atgttcacta ccgacgaagg 20

<210> SEQ ID NO 14
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 14
gacttggccg acgatctg 18

<210> SEQ ID NO 15
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 15
gctgcggaag aactccat 18

<210> SEQ ID NO 16
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 16
ctcgaatcgg tggaaacc 18

<210> SEQ ID NO 17
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 17
gatccgttgt cccgcact 18

<210> SEQ ID NO 18
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 18
gtgagccgat acgtcaattc 20

<210> SEQ ID NO 19
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 19
cttcaattca ccgcgtttt 19

<210> SEQ ID NO 20
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 20
ctgcggaaga actccatc 18

<210> SEQ ID NO 21
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 21
gatctgatcg acgaacttgc 20

<210> SEQ ID NO 22
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 22
catagtgacg gcattcgac 19

<210> SEQ ID NO 23
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 23
atccgagttg agggtgtctt 20

<210> SEQ ID NO 24
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 24
atcagatcga ttccgttctc 20

<210> SEQ ID NO 25
<211> LENGTH: 18

-continued

<212> TYPE: DNA
<213> ORGANISM: Artificial Sequence
<220> FEATURE:
<223> OTHER INFORMATION: oligonucleotide primer

<400> SEQUENCE: 25
ctcgaatcgg tggaaacc 18

<210> SEQ ID NO 26
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 26
ggtcgagtat aagcccgata 20

<210> SEQ ID NO 27
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 27
gtgatcaatg ccgtcacc 18

<210> SEQ ID NO 28
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 28
gttccgctat agcttcgaca 20

<210> SEQ ID NO 29
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 29
gagccaccag gtagtactcg 20

<210> SEQ ID NO 30
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 30
accggactac gtccatcaac 20

<210> SEQ ID NO 31
<211> LENGTH: 18
<212> TYPE: DNA
<213> ORGANISM: Artificial Sequence
<220> FEATURE:
<223> OTHER INFORMATION: oligonucleotide primer

<400> SEQUENCE: 31
gttggcttcc cggtcctt 18

-continued

<210> SEQ ID NO 32
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 32
gtgaaaccct ccaggtacg 19

<210> SEQ ID NO 33
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 33
acgatctcgg tcagattgtc 20

<210> SEQ ID NO 34
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 34
gagccaccag gtagtactcg 20

<210> SEQ ID NO 35
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 35
tttcctttcg gtgatggtc 19

<210> SEQ ID NO 36
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 36
gcgctctaca tccaggact 19

<210> SEQ ID NO 37
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 37
ccgctatagc ttcgacaatc 20

<210> SEQ ID NO 38
<211> LENGTH: 19
<212> TYPE: DNA
<213> ORGANISM: Artificial Sequence
<220> FEATURE:
<223> OTHER INFORMATION: oligonucleotide primer -continued

<400> SEQUENCE: 38
caccagctcg catatgttc 19

<210> SEQ ID NO 39
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 39
aacggcttgg aggtgtactt 20

<210> SEQ ID NO 40
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 40
gcggtcattg aacaacctat 20

<210> SEQ ID NO 41
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 41
cccggtccac tattacgac 19

<210> SEQ ID NO 42
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 42
ctgcgtgaga tgacgtacc 19

<210> SEQ ID NO 43
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 43
gagatcgcat acgaatccac 20

<210> SEQ ID NO 44
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 44
atgagaacgg caatcgttat 20

<210> SEQ ID NO 45
<211> LENGTH: 20

<212> TYPE: DNA
<213> ORGANISM: Artificial Sequence
<220> FEATURE:
<223> OTHER INFORMATION: oligonucleotide primer

<400> SEQUENCE: 45
gaatgagcat ctgggtatcg 20

<210> SEQ ID NO 46
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 46
gattgggtcg agacgattc 19

<210> SEQ ID NO 47
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 47
gagatcgcat acgaatccac 20

<210> SEQ ID NO 48
<211> LENGTH: 21
<212> TYPE: DNA
<213> ORGANISM: Artificial Sequence
<220> FEATURE:
<223> OTHER INFORMATION: oligonucleotide primer

<400> SEQUENCE: 48
cgttatacca ggacgacaaa g 21

<210> SEQ ID NO 49
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 49
gcggaatgtc gtaatagtgg 20

<210> SEQ ID NO 50
<211> LENGTH: 19
<212> TYPE: DNA
<213> ORGANISM: Artificial Sequence
<220> FEATURE:
<223> OTHER INFORMATION: oligonucleotide primer

<400> SEQUENCE: 50
caagaggaac cgttgatcg 19

<210> SEQ ID NO 51
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 51
gttatacgtg ccgaacgact 20

-continued

<210> SEQ ID NO 52
<211> LENGTH: 20
<212> TYPE: DNA
<213> ORGANISM: Artificial Sequence
<220> FEATURE:
<223> OTHER INFORMATION: oligonucleotide primer

<400> SEQUENCE: 52
cagtagtcgg tcgatttcgt 20

<210> SEQ ID NO 53
<211> LENGTH: 167
<212> TYPE: DNA
<213> ORGANISM: Artificial Sequence
<220> FEATURE:
<223> OTHER INFORMATION: oligonucleotide probe

<400> SEQUENCE: 53
cggccattgt tctacagtct gcatcgcggg cgacctgccg aactgtccgc tgacacggtc 60
gccgccgtgc tcaagcaggc cgccgaatcc gcgcgtactc aatgcccttc gatcccggcg 120
aacatccact gtcacctgct gcggaagacc aaagcgatgg atctcta 167

<210> SEQ ID NO 54
<211> LENGTH: 172
<212> TYPE: DNA
<213> ORGANISM: Artificial Sequence
<220> FEATURE:
<223> OTHER INFORMATION: oligonucleotide probe

<400> SEQUENCE: 54
gccatctgca cgtctacctc gacgagttcc acccgaacat caccaaactg cccgcgagac 60
ggccattgtt ctacagtctg catcgcgggc gacctgccga actgtccgct gacacggtcg 120
ccgccgtgct caagcaggcc gccgaatccg cgcgtactca atgcccttcg at 172

<210> SEQ ID NO 55
<211> LENGTH: 219
<212> TYPE: DNA
<213> ORGANISM: Artificial Sequence
<220> FEATURE:
<223> OTHER INFORMATION: oligonucleotide probe

<400> SEQUENCE: 55
aacatccact gtcacctgct gcggaagacc aaagcgatgg atctctacca gcagggcatc 60
ccgctaccga tcatcatgcg cctcctcggc cacgaaaacg cttccaccac agcagctttc 120
tatgcctttg caaccctgga catgatgcgt caagcgatca acgccgccac ccccgcgatc 180
aacaccgcgg ccaccgagcc actcaccgaa gaccaactc 219

<210> SEQ ID NO 56
<211> LENGTH: 167
<212> TYPE: DNA
<213> ORGANISM: Artificial Sequence
<220> FEATURE:
<223> OTHER INFORMATION: oligonucleotide probe

<400> SEQUENCE: 56
ccaccacagc agctttctat gcctttgcaa ccctggacat gatgcgtcaa gcgatcaacg 60
ccgccacccc cgcgatcaac accgcggcca ccgagccact caccgaagac caactccaaa 120
ccctctacag tctgcgataa ccgcctgaaa cgttaagccg agaaatc 167

-continued

<210> SEQ ID NO 57
<211> LENGTH: 216
<212> TYPE: DNA
<213> ORGANISM: Artificial Sequence
<220> FEATURE:
<223> OTHER INFORMATION: oligonucleotide probe

<400> SEQUENCE: 57
atgttcacta ccgacgaagg cgccgacacc cattgccagc tcggcaacct gacgtcgtcg 60
aatgccgtca ctatggattg gctcgaagac accctcaact cggattgatc gttgcgccgc 120
ttcaattcac cgcgttttgc ttgccgcctg gccggcgctt cgcaccacgc tgcggaagaa 180
ctccatccgc gcggtgacca gatcgtcggc caagtc 216

<210> SEQ ID NO 58
<211> LENGTH: 168
<212> TYPE: DNA
<213> ORGANISM: Artificial Sequence
<220> FEATURE:
<223> OTHER INFORMATION: oligonucleotide probe

<400> SEQUENCE: 58
gctgcggaag aactccatcc gcgcggtgac cagatcgtcg gccaagtcca gggcagcgtc 60
gacaacggtc ttgcgtcgtg actcgtcggg gagaacggaa tcgatctgat cgacgaactt 120
gcggacggcc tcgatggcct tttgcggcc ggtttccacc gattcgag 168

<210> SEQ ID NO 59
<211> LENGTH: 336
<212> TYPE: DNA
<213> ORGANISM: Artificial Sequence
<220> FEATURE:
<223> OTHER INFORMATION: oligonucleotide probe

<400> SEQUENCE: 59
atgttcacta ccgacgaagg cgccgacacc cattgccagc tcggcaacct gacgtcgtcg 60
aatgccgtca ctatggattg gctcgaagac accctcaact cggattgatc gttgcgccgc 120
ttcaattcac cgcgttttgc ttgccgcctg gccggcgctt cgcaccacgc tgcggaagaa 180
ctccatccgc gcggtgacca gatcgtcggc caagtccagg gcagcgtcga caacggtctt 240
gcgtcgtgac tcgtcgggga gaacggaatc gatctgatcg acgaacttgc ggacggcctc 300
gatggccttt ttgcggccgg tttccaccga ttcgag 336

<210> SEQ ID NO 60
<211> LENGTH: 181
<212> TYPE: DNA
<213> ORGANISM: Artificial Sequence
<220> FEATURE:
<223> OTHER INFORMATION: oligonucleotide probe

<400> SEQUENCE: 60
gatccgttgt cccgcactgg cgctcgtcgg ctccggcgag ggcggtgagc cgatacgtca 60
attcaacgta ttcgcccgac aggccggcgg gccggtgacc gctcggatgt tcactaccga 120
cgaaggcgcc gacacccatt gccagctcgg caacctgacg tcgtcgaatg ccgtcactat 180
g 181

<210> SEQ ID NO 61
<211> LENGTH: 167
<212> TYPE: DNA
<213> ORGANISM: Artificial Sequence
<220> FEATURE:
<223> OTHER INFORMATION: oligonucleotide probe

<400> SEQUENCE: 61
gtgagccgat acgtcaattc aacgtattcg cccgacaggc cggcgggccg gtgaccgctc 60
ggatgttcac taccgacgaa ggcgccgaca cccattgcca gctcggcaac ctgacgtcgt 120
cgaatgccgt cactatggat tggctcgaag acaccctcaa ctcggat 167

<210> SEQ ID NO 62
<211> LENGTH: 159
<212> TYPE: DNA
<213> ORGANISM: Artificial Sequence
<220> FEATURE:
<223> OTHER INFORMATION: oligonucleotide probe

<400> SEQUENCE: 62
cttcaattca ccgcgttttg cttgccgcct ggccggcgct tcgcaccacg ctgcggaaga 60
actccatccg cgcggtgacc agatcgtcgg ccaagtccag ggcagcgtcg acaacggtct 120
tgcgtcgtga ctcgtcgggg agaacggaat cgatctgat 159

<210> SEQ ID NO 63
<211> LENGTH: 167
<212> TYPE: DNA
<213> ORGANISM: Artificial Sequence
<220> FEATURE:
<223> OTHER INFORMATION: oligonucleotide probe

<400> SEQUENCE: 63
ctgcggaaga actccatccg cgcggtgacc agatcgtcgg ccaagtccag ggcagcgtcg 60
acaacggtct tgcgtcgtga ctcgtcgggg agaacggaat cgatctgatc gacgaacttg 120
cggacggcct cgatggcctt tttgcggccg gtttccaccg attcgag 167

<210> SEQ ID NO 64
<211> LENGTH: 163
<212> TYPE: DNA
<213> ORGANISM: Artificial Sequence
<220> FEATURE:
<223> OTHER INFORMATION: oligonucleotide probe

<400> SEQUENCE: 64
gatctgatcg acgaacttgc ggacggcctc gatggccttt ttgcggccgg tttccaccga 60
ttcgagcacc tcgtcggaaa gttcggccca gcgtggctcg gccttctgcg gcgtctctgt 120
catgatgtca actccctgaa ctctatcggg cttatactcg acc 163

<210> SEQ ID NO 65
<211> LENGTH: 156
<212> TYPE: DNA
<213> ORGANISM: Artificial Sequence
<220> FEATURE:
<223> OTHER INFORMATION: oligonucleotide probe

<400> SEQUENCE: 65
gtgatcaatg ccgtcacccg ctccggtgtc cggctcgcga tccgcagccc gatgggtgct 60
ccgtagtcct ggatgtagag cgcaaagcgc tgcaggccga gcttgtccac gaggccttcg 120
acgatctcgg tcagattgtc gaagctatag cggaac 156

<210> SEQ ID NO 66
<211> LENGTH: 156
<212> TYPE: DNA
<213> ORGANISM: Artificial Sequence
<220> FEATURE:
<223> OTHER INFORMATION: oligonucleotide probe

<400> SEQUENCE: 66
gagccaccag gtagtactcg tcggagagcg cggcgatgag attgcggaac atatgcgagc 60
tggtggggaa gccgtgcagc aggagcaaag ccgggtttcg cggattgccg gcctcccgga 120
agtacacctc caagccgttg atggacgtag tccggt 156

<210> SEQ ID NO 67
<211> LENGTH: 358
<212> TYPE: DNA
<213> ORGANISM: Artificial Sequence
<220> FEATURE:
<223> OTHER INFORMATION: oligonucleotide probe

<400> SEQUENCE: 67
ccggctcgcg atccgcagcc cgatgggtgc tccgtagtcc tggatgtaga gcgcaaagcg 60
ctgcaggccg agcttgtcca cgaggccttc gacgatctcg gtcagattgt cgaagctata 120
gcggaactcg tcgaccgacg gtgcggccga attgccgaag ccgatgtaat cgggagccac 180
caggtagtac tcgtcggaga gcgcggcgat gagattgcgg aacatatgcg agctggtggg 240
gaagccgtgc agcaggagca aagccgggtt tcgcggattg ccggcctccc ggaagtacac 300
ctccaagccg ttgatggacg tagtccggtg ccgggtgtcg aaggtagtca ttgcggtt 358

<210> SEQ ID NO 68
<211> LENGTH: 165
<212> TYPE: DNA
<213> ORGANISM: Artificial Sequence
<220> FEATURE:
<223> OTHER INFORMATION: oligonucleotide probe

<400> SEQUENCE: 68
gttggcttcc cggtccttgg cgtgggcgaa caagatgtcc cagaacggcg tgaaaccctc 60
caggtacgca ttgccgctct gggtgatcaa tgccgtcacc cgctccggtg tccggctcgc 120
gatccgcagc ccgatgggtg ctccgtagtc ctggatgtag agcgc 165

<210> SEQ ID NO 69
<211> LENGTH: 186
<212> TYPE: DNA
<213> ORGANISM: Artificial Sequence
<220> FEATURE:
<223> OTHER INFORMATION: oligonucleotide probe

<400> SEQUENCE: 69
gtgaaaccct ccaggtacgc attgccgctc tgggtgatca atgccgtcac ccgctccggt 60
gtccggctcg cgatccgcag cccgatgggt gctccgtagt cctggatgta gagcgcaaag 120
cgctgcaggc cgagcttgtc cacgaggcct tcgacgatct cggtcagatt gtcgaagcta 180
tagcgg 186

<210> SEQ ID NO 70
<211> LENGTH: 147
<212> TYPE: DNA
<213> ORGANISM: Artificial Sequence
<220> FEATURE:
<223> OTHER INFORMATION: oligonucleotide probe

<400> SEQUENCE: 70
acgatctcgg tcagattgtc gaagctatag cggaactcgt cgaccgacgg tgcggccgaa 60
ttgccgaagc cgatgtaatc gggagccacc aggtagtact cgtcggagag cgcggcgatg 120
agattgcgga acatatgcga gctggtg 147

<210> SEQ ID NO 71
<211> LENGTH: 139
<212> TYPE: DNA
<213> ORGANISM: Artificial Sequence
<220> FEATURE:
<223> OTHER INFORMATION: oligonucleotide probe

<400> SEQUENCE: 71
gagccaccag gtagtactcg tcggagagcg cggcgatgag attgcggaac atatgcgagc 60
tggtggggaa gccgtgcagc aggagcaaag ccgggtttcg cggattgccg gcctcccgga 120
agtacacctc caagccgtt 139

<210> SEQ ID NO 72
<211> LENGTH: 164
<212> TYPE: DNA
<213> ORGANISM: Artificial Sequence
<220> FEATURE:
<223> OTHER INFORMATION: oligonucleotide probe

<400> SEQUENCE: 72
tttcctttcg gtgatggtcg ggtgccggtc gggagaacga gcgttctcac ggctggttgt 60
agtctagaga acgatcgttc ttagcgcaag gagggaatgc catgaccgaa ggcgaggacc 120
gggataatgt gctcgccgca gccgataggt tgttcaatga ccgc 164

<210> SEQ ID NO 73
<211> LENGTH: 163
<212> TYPE: DNA
<213> ORGANISM: Artificial Sequence
<220> FEATURE:
<223> OTHER INFORMATION: oligonucleotide probe

<400> SEQUENCE: 73
cccggtccac tattacgaca ttccgctgcg tgggccgata ttcagaatcg accgcatggt 60
ccgccgcaac ctgcatcgca cggcaaccga tcaacggttc ctcttgggcg ccaacatggc 120
aatccggacc tcggcgtggc aggcggtacg tcatctcacg cag 163

<210> SEQ ID NO 74
<211> LENGTH: 158
<212> TYPE: DNA
<213> ORGANISM: Artificial Sequence
<220> FEATURE:
<223> OTHER INFORMATION: oligonucleotide probe

<400> SEQUENCE: 74
gagatcgcat acgaatccac gatggtggtg ggcgcgtctg gccgccgggt ggaatgctca 60
ccgctcgact tttttcgcta cgcgacgcgt tataccagga cgacaaaggc gcacggcgtc 120
aagagtcgtt cggcacgtat aacgattgcc gttctcat 158

<210> SEQ ID NO 75
<211> LENGTH: 387
<212> TYPE: DNA
<213> ORGANISM: Artificial Sequence
<220> FEATURE:
<223> OTHER INFORMATION: oligonucleotide probe

<400> SEQUENCE: 75
gggccgatat tcagaatcga ccgcatggtc cgccgcaacc tgcatcgcac ggcaaccgat 60
caacggttcc tcttgggcgc caacatggca atccggacct cggcgtggca ggcggtacgt 120
catctcacgc agctggatct ggaagaccga ctccacgaag acatcgatct tgcactgaca 180
ctgttcaaga ataatttcga gatcgcatac gaatccacga tggtggtggg cgcgtctggc 240
cgccgggtgg aatgctcacc gctcgacttt tttcgctacg cgacgcgtta taccaggacg 300
acaaaggcgc acggcgtcaa gagtcgttcg gcacgtataa cgattgccgt tctcatgctg 360
ggatatgtgc cggtccgaac actgcgg 387

<210> SEQ ID NO 76
<211> LENGTH: 185
<212> TYPE: DNA
<213> ORGANISM: Artificial Sequence
<220> FEATURE:
<223> OTHER INFORMATION: oligonucleotide probe

<400> SEQUENCE: 76
gaatgagcat ctgggtatcg cgccgacgcg taactgtggg ttcgaccacg cgcgcagtca 60
gatcatcggc cggatcgatg ccgattccgt tgttgacacg gattgggtcg agacgattcg 120
ccagtgtttt caagactccg ccatcgacgc ggtcaccggc ccggtccact attacgacat 180
tccgc 185

<210> SEQ ID NO 77
<211> LENGTH: 165
<212> TYPE: DNA
<213> ORGANISM: Artificial Sequence
<220> FEATURE:
<223> OTHER INFORMATION: oligonucleotide probe

<400> SEQUENCE: 77
gattgggtcg agacgattcg ccagtgtttt caagactccg ccatcgacgc ggtcaccggc 60
ccggtccact attacgacat tccgctgcgt gggccgatat tcagaatcga ccgcatggtc 120
cgccgcaacc tgcatcgcac ggcaaccgat caacggttcc tcttg 165

<210> SEQ ID NO 78
<211> LENGTH: 143
<212> TYPE: DNA
<213> ORGANISM: Artificial Sequence
<220> FEATURE:
<223> OTHER INFORMATION: oligonucleotide probe

<400> SEQUENCE: 78
gagatcgcat acgaatccac gatggtggtg ggcgcgtctg gccgccgggt ggaatgctca 60
ccgctcgact tttttcgcta cgcgacgcgt tataccagga cgacaaaggc gcacggcgtc 120
aagagtcgtt cggcacgtat aac 143

<210> SEQ ID NO 79
<211> LENGTH: 182
<212> TYPE: DNA
<213> ORGANISM: Artificial Sequence
<220> FEATURE:
<223> OTHER INFORMATION: oligonucleotide probe

<400> SEQUENCE: 79
cgttatacca ggacgacaaa ggcgcacggc gtcaagagtc gttcggcacg tataacgatt 60
gccgttctca tgctgggata tgtgccggtc cgaacactgc ggttctttta tgacgccgag 120
aacaatcggt tcacgcgcaa gcgctccggg acgggcggcg gaacgaaatc gaccgactac 180
tg 182

<210> SEQ ID NO 80
<211> LENGTH: 27

-continued

```
<212> TYPE: DNA
<213> ORGANISM: Artificial Sequence
<220> FEATURE:
<223> OTHER INFORMATION: oligonucleotide probe

<400> SEQUENCE: 80

actcaatgcc cttcgatccc ggcgaac                                         27


<210> SEQ ID NO 81
<211> LENGTH: 324
<212> TYPE: DNA
<213> ORGANISM: Mycobacterium tuberculosis

<400> SEQUENCE: 81

cgtactcgac ctgaaagacg ttatccacca tacggatagg ggatctcagt acacatcgat     60

ccggttcagc gagcggctcg ccgaggcagg catccaaccg tcggtcggag cggtcggaag    120

ctcctatgac aatgcactag ccgagacgat caacggccta tacaagaccg agctgatcaa    180

acccggcaag ccctggcggt ccatcgagga tgtcgagttg gccaccgcgc gctgggtcga    240

ctggttcaac catcgccgcc tctaccagta ctgcggcgac gtcccgccgg tcgaactcga    300

ggctgcctac tacgctcaac gcca                                           324
```